(12) United States Patent
Scholz et al.

(10) Patent No.: US 11,510,871 B2
(45) Date of Patent: *Nov. 29, 2022

(54) METHOD FOR PRODUCING LOW VISCOUS AND HIGHLY CONCENTRATED BIOPHARMACEUTICAL DRUG PRODUCTS IN LIQUID FORMULATION

(71) Applicant: Leukocare AG, Martinsried (DE)

(72) Inventors: Martin Scholz, Munich (DE); Kristina Kemter, Garching bei Munich (DE); Jens Altrichter, Kavelstorf (DE); Thomas Kriehuber, Garching bei Munich (DE)

(73) Assignee: Leukocare AG, Martinsried (DE)

( * ) Notice: Subject to any disclaimer, the term of this patent is extended or adjusted under 35 U.S.C. 154(b) by 436 days.

This patent is subject to a terminal disclaimer.

(21) Appl. No.: 16/332,716

(22) PCT Filed: Sep. 15, 2017

(86) PCT No.: PCT/EP2017/073373
§ 371 (c)(1),
(2) Date: Mar. 12, 2019

(87) PCT Pub. No.: WO2018/050873
PCT Pub. Date: Mar. 22, 2018

(65) Prior Publication Data
US 2019/0216734 A1   Jul. 18, 2019

(30) Foreign Application Priority Data
Sep. 16, 2016   (EP) .................................... 16189318

(51) Int. Cl.
| A61K 9/08 | (2006.01) |
| A61K 9/00 | (2006.01) |
| A61K 47/18 | (2017.01) |
| A61K 47/26 | (2006.01) |
| C07K 1/14 | (2006.01) |
| A61K 39/395 | (2006.01) |

(52) U.S. Cl.
CPC .............. *A61K 9/08* (2013.01); *A61K 9/0019* (2013.01); *A61K 39/39591* (2013.01); *A61K 47/183* (2013.01); *A61K 47/26* (2013.01); *C07K 1/14* (2013.01); *C12N 2500/32* (2013.01)

(58) Field of Classification Search
CPC ....................................................... A61K 9/08
USPC ........................................................ 530/412
See application file for complete search history.

(56) References Cited

U.S. PATENT DOCUMENTS

| 9,610,343 B2 | 4/2017 | Jin et al. |
| 2008/0071063 A1 | 3/2008 | Mian et al. |
| 2011/0081380 A1 | 4/2011 | Francon et al. |
| 2014/0127227 A1 | 5/2014 | Chang |
| 2014/0127260 A1 | 5/2014 | Chintala et al. |
| 2018/0339036 A1 | 11/2018 | Scholz et al. |
| 2022/0202717 A1 | 6/2022 | Kemter et al. |

FOREIGN PATENT DOCUMENTS

| EA | 201291355 A1 | 4/2013 |
| EA | 023446 B1 | 6/2016 |
| EP | 1854478 A1 | 11/2007 |
| JP | 2009-516519 A | 4/2009 |

(Continued)

OTHER PUBLICATIONS

European Search Report dated Feb. 24, 2017 in European application No. EP 16189346.6, 6 pages.
European Search Report dated Mar. 2, 2017 in European application No. 16189276.5, 13 pages.
International Search Report and Written Opinion dated Oct. 26, 2017 in International application No. PCT/EP2017/073368, 8 pages.
International Search Report and Written Opinion dated Nov. 12, 2017 in International application No. PCT/EP2017/073370, 8 pages.
International Search Report and Written Opinion dated Nov. 24, 2017 in International application No. PCT/EP2017/073374, 10 pages.

(Continued)

*Primary Examiner* — Sean E Aeder
(74) *Attorney, Agent, or Firm* — Lee & Hayes, P.C.

(57) ABSTRACT

The present invention relates to a method of producing low viscous and highly concentrated biopharmaceutical drug products comprising a biomolecule of interest, the method comprising: (a) a first phase of preparing a drug substance of the biomolecule of interest, said first phase comprising at least one processing step selected from (a1) harvesting, (a2) purification, (a3) re-buffering, and (a4) enrichment, wherein said at least one processing step in this first phase is carried out in the presence of a composition comprising at least three amino acids, wherein the combination of said at least three amino acids provides at least one positively charged functional group, at least one anti-oxidative functional group, at least one osmolytic function, and at least one buffering function, and (b) a second phase of further processing the drug substance prepared in (a) to obtain a low viscous and highly concentrated biopharmaceutical drug product, said second phase comprising at least one processing step selected from (b1) re-buffering, (b2) freezing, (b3) thawing, and (b4) filling; wherein said at least one processing step in this second phase is carried out in the presence of a composition comprising (i) at least three amino acids, wherein the combination of said at least three amino acids provides at least one positively charged functional group, at least one anti-oxidative functional group, at least one osmolytic function, and at least one buffering function; and (ii) one or more sugar(s); in an amino acid:sugar ratio between 10:1 to 1:100 (w/w). The present invention further relates to a low viscous and highly concentrated biopharmaceutical drug product obtained or obtainable by the method of the invention.

12 Claims, 28 Drawing Sheets

(56) References Cited

FOREIGN PATENT DOCUMENTS

Figure 1:
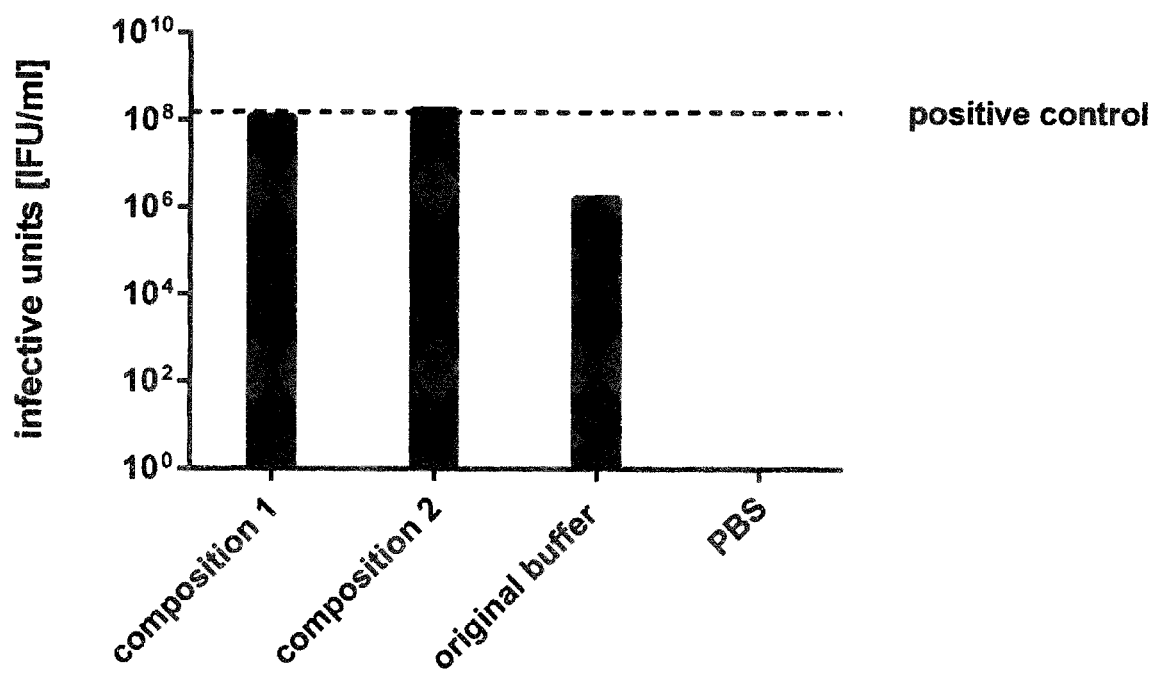

| | | |
|---|---|---|
| JP | 2014-522827 A | 9/2014 |
| JP | 2014-523243 A | 9/2014 |
| JP | 2015-525748 A | 9/2015 |
| JP | 5798356 B2 | 10/2015 |
| WO | WO2005066333 A1 | 7/2005 |
| WO | WO 2007/056847 A1 * | 5/2007 |
| WO | WO2007056847 A1 | 5/2007 |
| WO | WO2007104562 A1 | 9/2007 |
| WO | WO2013001034 | 1/2013 |
| WO | WO2013001044 | 1/2013 |
| WO | WO2013055958 A1 | 4/2013 |
| WO | WO2014004578 A1 | 1/2014 |
| WO | WO2015005928 A1 | 1/2015 |
| WO | WO2015040234 A1 | 3/2015 |
| WO | WO2015059284 A1 | 4/2015 |
| WO | WO2015140751 A1 | 9/2015 |
| WO | WO2016087457 A1 | 6/2016 |
| WO | WO2018050870 A1 | 3/2018 |

OTHER PUBLICATIONS

Kissmann et al., "H1N1 influenza virus-like particles: Physical degradation pathways and identification of stabilizers," Feb. 2011, Journal of Pharmaceutical Sciences, 100 (2): 634-645.

Lua et al., "Bioengineering virus-like particles as vaccines," Mar. 2014, Biotechnology and Bioengineering, 111(3):425-140.

Lynch et al., "Stability studies of HIV-1 Pr55gag virus-like particles made in insect cells after storage in various formulation media," Sep. 2012, Virology Journal, 9(1): 210. 5 pages.

Mohr et al., "Virus-like particle formulation optimization by miniaturized high-throughput screening," May 2013, Methods, 60(3): 248-256.

Croyle et. al., "Development of a Highly Efficient Purification Process for Recombinant Adenoviral Vectors for Oral Gene Delivery," 1998. Pharmaceutical Development and Technology, 3(3): 365-372.

Vazquez-Rey, et al., "Aggregates in Monoclonal Antibody Manufacturing Processes," Apr. 2011, Biotechnology and Bioengineering, 108(7): 1494-1508.

International Search Report and Written Opinion dated Nov. 23, 2017 in International application No. PCT/EP2017/073373, 12 pages.

Scherliess et al., "Induction of protective immunity against H1N1 influenza A(H1N1)pdm09 with spray-dried and electron-beam sterilised vaccines in non-human primates," Mar. 2014, Vaccines, 32(19): 2231-2240.

Chen, et al., "Development of a simple assay system for protein stabilization efficiency based on hemoglobin protection against denaturation and measuremnet of the cooperative effect of mixing protein stabilizers" Bioscience Biotechnology Biochemistry, vol. 80, Iss. 10, 2016, pp. 1874-1878.

Japanese Office action dated Jun. 23, 2021 in JP Application No. 2019-514710, a foreign corresponding application of U.S. Appl. No. 16/333,726, 8 pages.

Japanese Office action dated Jun. 24, 2021 in JP Application No. 2019-514711, a foreign corresponding application of U.S. Appl. No. 16/328,061, 10 pages.

Korean Office action dated Aug. 30, 2021 in KR Application No. 10-2019-7010722, a foreign corresponding application of U.S. Appl. No. 16/328,061, 13 pages.

Russian Office action dated Jul. 8, 2020 in RU Application No. 2019111152/04(021667), a foreign corresponding application of U.S. Appl. No. 16/328,061, 17 pages.

Ball, "Proteins Unravelled", Dec. 2009, Chemistry World, pp. 58-62.

European Office Action dated Apr. 14, 2022 in European U.S. Appl. No. 16/332,716, a foreign corresponding application of U.S. Appl. No. 16/332,716, 5 pages.

Hada, et al., "Evaluation of Antioxidants in Protein Formulation Against Oxidative Stress Using Various Biophysical Methods" Jan. 2016, Int. J. Biol.Macromol., 82: 192-200.

Japanese Office action dated Feb. 15, 2022 in JP Application No. 2019-514711, a foreign corresponding application of U.S. Appl. No. 16/328,061, 7 pages.

Liu et al., "Reversible Self-Association Increases the Viscocity of a Concentrated Monoclonal Antibody in Aqueous Solution," Sep. 2005, Journal of Pharmaceutical Sciences, 94(9): 1928-1940.

Reeg, et al., "Protein Oxidation in Aging: Does It Play a Role in Aging Progression,"Jul. 2015, Antioxidants & Redox Signaling, 23(3): 239-255.

* cited by examiner

A

B

A

B

C

D

A

B

C

A

B

A

B

A

B

A

B

METHOD FOR PRODUCING LOW VISCOUS AND HIGHLY CONCENTRATED BIOPHARMACEUTICAL DRUG PRODUCTS IN LIQUID FORMULATION

CROSS REFERENCE TO RELATED APPLICATIONS

This Application is a U.S. National Phase Application of International No. PCT/EP2017/073373, filed Sep. 15, 2017, which claims priority to European Application No. 16189318.5, filed Sep. 16, 2016, which are hereby incorporated by reference in their entirety.

The present invention relates to a method of producing low viscous and highly concentrated biopharmaceutical drug products comprising a biomolecule of interest, the method comprising: (a) a first phase of preparing a drug substance of the biomolecule of interest, said first phase comprising at least one processing step selected from (a1) harvesting, (a2) purification, (a3) re-buffering, and (a4) enrichment; wherein said at least one processing step in this first phase is carried out in the presence of a composition comprising at least three amino acids, wherein the combination of said at least three amino acids provides at least one positively charged functional group, at least one anti-oxidative functional group, at least one osmolytic function, and at least one buffering function, and (b) a second phase of further processing the drug substance prepared in (a) to obtain a low viscous and highly concentrated biopharmaceutical drug product, said second phase comprising at least one processing step selected from (b1) re-buffering, (b2) freezing, (b3) thawing, and (b4) filling; wherein said at least one processing step in this second phase is carried out in the presence of a composition comprising (i) at least three amino acids, wherein the combination of said at least three amino acids provides at least one positively charged functional group, at least one anti-oxidative functional group, at least one osmolytic function, and at least one buffering function; and (ii) one or more sugar(s); in an amino acid: sugar ratio between 10:1 to 1:100 (w/w). The present invention further relates to a low viscous and highly concentrated biopharmaceutical drug product obtained or obtainable by the method of the invention.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The field of highly concentrated biopharmaceutical drug products, as well as the field of methods for their production, is rapidly increasing. In general, after up-scaled production of the biomolecule of interest, the highly concentrated biopharmaceutical drug product is obtained by two major subsequent downscaling phases. In the early first phase, the so-called drug substance (or bulk substance) is manufactured. In a second late phase, said drug substance is further processed (downstreamed) into a highly concentrated biopharmaceutical drug product.

Two crucial aspects during the production of highly concentrated biopharmaceutical drug products are the stability and the viscosity of the biomolecules employed. Pharmaceutical proteins and peptides, as well as more complex biomolecule particles comprising different kinds of molecules such as nucleic acids, polypeptides, proteins, polysaccharides and in the case of enveloped viruses or virus like particles also phospholipids, are known to undergo physical and chemical stress during each processing step. These stresses can lead to unappreciated molecular changes, which in turn often result in functional loss and, in some cases, even severe safety issues. The stability and viscosity of the final highly concentrated biopharmaceutical drug products is further challenged by aging processes depending on the respective storage conditions.

The molecular changes that occur within such highly concentrated biopharmaceutical drug products during the entirety of the manufacturing process are cumulative. In other words, the combined changes of: the individual manufacturing steps to produce the initial drug substance, its storage and shipment, the subsequent development steps from the drug substance to the drug product, including fill and finish procedures, the following shipment and storage of the drug product, as well as the steps required for its final preparation for application—they all add up to a number of unwanted molecular changes within the highly concentrated drug product. The avoidance of such molecular changes is thus an important aim, not only at the stage of formulating the final drug product, but also at the earlier downscaling phase in the drug substance manufacturing.

The drug substance manufacturing process typically starts with the harvesting of the biomolecule of interest as the first step, e.g. either from the production cell line or, in the case of secreted biomolecules, from the growth medium. The biomolecule harvested from the cell culture or the medium containing the crude biomolecule bulk drug substance is then further purified and characterized. Generally, the drug substance containing solution undergoes processing steps such as ultracentrifugation or several chromatographic steps in standard buffers. These buffers are typically optimized to enable satisfactory density gradient purification or chromatographic purification, but they normally do not contain any stabilizing excipients that are specifically selected for the individual biomolecule. Due to these procedures, the biomolecule or drug substance is usually exposed to physical and chemical stress already at this early phase of biopharmaceutical manufacturing. In particular the purification steps are typically associated with immense physical and chemical stresses. Accordingly, there is a general need to elicit maximum stabilization as early as possible, preferably during harvesting and/or purification.

The following step of characterization of the harvested biomolecule can be carried out by one (or more) of several potential analytical methods. Important for the operability of these analytical methods is that the buffer in which the harvested biomolecule or drug substance is present does not contain components that might interfere with analytical procedures and might lead to misinterpretations regarding the molecular integrity and purity of the biomolecule or highly concentrated drug substance. Thus, it is important to avoid all excipients that are not required for further downscaling process steps during the manufacturing of the drug product, while at the same time achieving a maximum stability and minimum viscosity of the highly concentrated drug substance as early as possible during or after harvesting, purification and/or characterization.

Once the highly concentrated drug substance has been confirmed to fulfill the requirements of molecular integrity and purity, the purified and characterized low viscous and highly concentrated drug substance is then dispended in excipients that are intended to maintain product quality and integrity during the subsequent steps of processing of the low viscous and highly concentrated drug substance, such as filtration, filling, packaging, storage and transport.

Typically, the highly concentrated drug substance is stored as frozen material. The draw-back of freezing is that cold denaturation (Privalov P L. Crit. Rev. Biochem. Mol. Biol., 1990) and protein unfolding effects might occur during these freeze-thaw procedures. While bulk freeze-thaw offers numerous operational and product quality benefits, it can also prove detrimental to highly concentrated drug substance stability due to cryo-concentration mechanisms. Such mechanisms include pH changes (Pikal-Cleland K A et al., J. Pharm. Sci., 2002) and uncontrolled progressive enrichment of excipients and biomolecules, which can result in modifications in the biomolecule structure (Rathore N and Rajan R S. Biotechnol. Prog., 2008: Webb S D et. al, BioPharm, 2002; Lashmar U T et al. BioProcess Int, 2007; Glaser V. Gen. Eng. Biotechnol. News, 2005). In addition, frozen highly concentrated substances necessarily need to be thawed before they can be further processed. Thawing can cause additional stress and damage to the highly concentrated drug substance, for example at ice-liquid interfaces and during recrystallization. In many cases, additional mixing processes are included during the thawing procedure. In these cases the mixing parameters have to be carefully adjusted to avoid further biomolecule damage through shear stress, foaming, and/or generation of air bubbles leading to drug substance damage at the liquid-air interface etc. (Rathore N and Rajan R S. Biotechnol. Prog., 2008).

The above described effects of highly concentrated drug substance or drug product freeze-thaw on any particular product are specific for the respective biomolecule employed and, thus, may affect product quality for some highly concentrated drug substance preparations but not for others. Prior to large scale processing, it is therefore advisable to evaluate the impact of multiple freeze-thaw cycles on the highly concentrated product quality for each individual product of interest. This is typically conducted in scale-down experiments with standardized parameters to mimic large scale processes, and often includes further systematic selection steps to identify the most suitable stabilizing excipients.

Once the highly concentrated drug substance has been obtained, it is further processed into a highly concentrated drug product. These subsequent processing steps, also often referred to as "formulation steps", include for example a concentration of the selected excipients, adjustment of the pH, as well as adjustment of the conductivity and the biomolecule concentration (i.e. enrichment of the biopharmaceutical product) as desired (Scott C., BioProcess Int., 2006). During this stage of development, further processes can also include steps such as dilution steps or buffer exchange (re-buffering). For buffer exchange, ultrafiltration or diafiltration operations are typically conducted that are chosen to limit biomolecule-solute interactions and that are known to result in adsorption events on surfaces and subsequent loss of molecular integrity of the drug substance (Stoner M R et al., J Pharm. Sci., 2004). Thus, a further aim when re-buffering or performing buffer exchange e.g. employing dialysis should be to reduce or avoid the known loss of molecular integrity and adsorption of the highly concentrated drug substance during interaction of the liquid with the membrane.

In the case of proteins, additional processing steps, such as sterile filtration and drug product filling, often subject the biomolecules of the highly concentrated drug substance to high shear stress and adsorption on surfaces that can cause protein unfolding (Maa Y and Hsu C C. Biotechnol. Bioeng., 1997). Significant levels of protein aggregation and precipitation were reported for therapeutic antibodies due to shear in the presence of solid-liquid interfaces (Biddlecombe et al., Biotechnol. Prog., 2007). In addition, when filling processes are not carried out under nitrogen, they can be associated with oxidation and deamidation of the biomolecule (Sharma B., Biotechnol. Adv., 2007).

Physical stresses can also occur during the subsequent handling, such as filling, packaging and labeling, in particular when the labeling is carried out without appropriate temperature control or if the sample is subjected to mechanical stress during labeling, storage, transport and delivery/administration to the subject. In particular shear stress, thermal stress and limited photostability during storage and transportation is a serious logistic and economical problem, especially for delivery sites with cold chain issues. As such, high temperatures can subject biomolecules to thermal stress that results in thermal unfolding and aggregation of protein-based biomolecules. In addition, the presence of light in combination with dissolved oxygen can lead to the formation of peroxy radicals, which can lead to photo-degradation of the peptide backbone (Davies M J and Dean R T., Oxford University Press, 1997).

Finally, for applications of highly concentrated biopharmaceutical drug products in medicine, including human or animal health, the intended route of administration has to be taken into consideration when choosing the composition of the final highly concentrated biopharmaceutical drug product, including the selection of appropriate excipients. For example, the intravenous, transdermal, intracutaneous, subcutaneous or intramuscular administration of highly concentrated therapeutic antibodies requires appropriate conditions, such as sufficient syringeability, injectability, low osmolality and low viscosity, in order to enable easy and painless administration.

International application WO 2005/007185 aims at stabilizing protein pharmaceuticals without the addition of the often used stabilizer human serum albumin (HSA). Instead, the stabilizing solution comprises (i) a surface-active substance that is preferably a non-ionic detergent, i.e. a surfactant and (ii) a mixture of at least two amino acids, wherein the at least two amino acids are either glutamate and glutamine or aspartate and asparagine. The aim of this application lies primarily in the stabilization of low-concentrated pharmaceutical compound during storage, in particular during long term storage over more than six months at increased temperatures. However, specific stabilization during processing and manufacturing are not described.

International application WO 2010/151703 discloses a pharmaceutical composition for increasing the stability, reducing aggregation or reducing immunogenicity of a peptide or polypeptide, comprising at least one alkylglycoside. Compositions comprising amino acids or specific amino acid combinations for use in processing of pharmaceutical compositions are not described.

US patent application US 2014/0127227 describes protein formulations containing at least one amino acid to address stability and viscosity even for high concentrated formulations. The application focuses on the stability of formulations of commercially available biopharmaceutical products, whereas effects of excipients on biopharmaceuticals during early development phases and during drug substance preparations are not addressed.

International application WO 2013/001044 describes the advantage of amino acid based compositions for preventing the unfolding and enabling efficient refolding of even complex biomolecules, such as IgM antibodies, during drying and reconstitution. International application WO 2010/115835 describes the advantage of amino acid containing compositions for protection of biomolecules immobilized on material surfaces even during irradiation and terminal sterilization. Also in WO 2010/112576, the advantage of amino acid containing compositions for protection of biomolecules during irradiation and terminal sterilization are disclosed, here for biomolecules in a closed container. In international application WO 2013/001034, the advantage of amino acid containing compositions for protection of live viruses during storage and transport are described. Finally, in WO 2015/059284, the advantage of amino acid containing compositions for the protection of commercially available vaccines, e.g. against influenza, during thermal stress, spray drying, and terminal sterilization are described. However, stabilization during the various processing steps of production of an antibody, including early processing steps, and during final formulation into a drug product is not addressed in any of these applications.

In summary, most stabilization approaches available so far focus on one particular step in the production process, on improved storage conditions or on optimized formulations for the intended route of administration. So far, no consideration has been given to avoiding early molecular changes and increasing viscosity during highly concentrated biopharmaceutical drug substance and drug product manufacturing and avoiding the potential multiplication of these early instabilities and increasing viscosity during further processing. Moreover, none of these approaches has been developed by considering the overall preparation process, i.e. with the aim of providing improved protection throughout the majority or even all production, downstream processing and formulation steps, while at the same time minimizing the amount of different stabilization compositions required for these steps. Accordingly, there is still a need to improve the presently existing formulation design in order to improve highly concentrated biopharmaceutical drug product stability at low viscosity.

This need is addressed by the provision of the embodiments characterized in the claims.

Accordingly, the present invention relates to a method of producing a low viscous and highly concentrated biopharmaceutical drug products comprising a biomolecule of interest, the method comprising: (a) a first phase of preparing a drug substance of the biomolecule of interest, said first phase comprising at least one processing step selected from (a1) harvesting, (a2) purification, (a3) re-buffering, and (a4) enrichment; wherein said at least one processing step in this first phase is carried out in the presence of a composition comprising at least three amino acids, wherein the combination of said at least three amino acids provides at least one positively charged functional group, at least one anti-oxidative functional group, at least one osmolytic function, and at least one buffering function, and (b) a second phase of further processing the drug substance prepared in (a) to obtain a low viscous and highly concentrated biopharmaceutical drug product, said second phase comprising at least one processing step selected from (b1) re-buffering, (b2) freezing, (b3) thawing, and (b4) filling; wherein said at least one processing step in this second phase is carried out in the presence of a composition comprising (i) at least three amino acids, wherein the combination of said at least three amino acids provides at least one positively charged functional group, at least one anti-oxidative functional group, at least one osmolytic function, and at least one buffering function; and (ii) one or more sugar(s); in an amino acid: sugar ratio between 10:1 to 1:100 (w/w).

The term "biopharmaceutical drug product", as used herein, is well known and relates to a pharmaceutical drug product, wherein said drug product is based on one or more biomolecules (also referred to here as biomolecule-based pharmaceutical product). Encompassed by said term is any biomolecule-based pharmaceutical product manufactured in, extracted from, or semi-synthesized from biological sources or synthesized, e.g. chemically synthesized or via in vitro systems, such as e.g. in vitro translated proteins etc. The term "biopharmaceutical products" is also used interchangeably with the terms "biopharmaceuticals", "drug product", "biologic(al) medical products", "biological", or "biologics".

The low viscous and highly concentrated highly concentrated biopharmaceutical drug product comprises a biomolecule of interest. The term "a biomolecule", as used herein, relates to any molecule that is typically present in living organisms. Preferred biomolecules are large macromolecules such as proteins, carbohydrates, lipids, and nucleic acids, as well as small molecules such as primary metabolites, secondary metabolites, and natural products. It will be appreciated that the term "a biomolecule" is not limited to one type of biomolecule, but may also encompass more than one biomolecule, i.e. it also refers to "one or more biomolecule(s)".

The method of the present invention relates to the production of such a low viscous and highly concentrated biopharmaceutical drug product, wherein the production comprises two phases. In the first phase, the low viscous and highly concentrated drug substance of the biomolecule of interest is prepared and in the second phase, said drug substance is further processed to obtain the low viscous and highly concentrated biopharmaceutical drug product.

The term "drug substance" is used herein interchangeably with the terms "bulk substance" or "bulk drug substance". These terms are well known in the art and refer to any substance that is represented for use in a drug and that, when used in the manufacturing, processing, or packaging of a drug, becomes an active ingredient or a finished dosage form of the drug. According to the FDA definition, this term does not include intermediates used in the synthesis of such substances.

Said first phase of the production method of the present invention comprises at least one processing step selected from (a1) harvesting, (a2) purification, (a3) re-buffering, and (a4) enrichment.

The term "comprising", as used herein, denotes that further steps and/or components can be included in addition to the recited steps and/or components. However, this term also encompasses that the claimed subject-matter consists of exactly the recited steps and/or components.

The term "at least", as used herein, refers to the specifically recited amount or number but also to more than the specifically recited amount or number. For example, the term "at least one" encompasses also at least 2, at least 3, at least 4, at least 5, at least 6, at least 7, at least 8, at least 9, at least 10, such as at least 20, at least 30, at least 40, at least 50 and so on. Furthermore, this term also encompasses exactly 1, exactly 2, exactly 3, exactly 4, exactly 5, exactly 6, exactly 7, exactly 8, exactly 9, exactly 10, exactly 20, exactly 30, exactly 40, exactly 50 and so on. In the context of the recited processing steps, the term "at least one processing step selected from" encompasses that one, two, three, four or five of said processing steps are carried out, but also that all six processing steps are carried out. It will be appreciated that the order of listing these processing steps is not particularly limiting, although it is preferred that in those cases where more than one step is carried out, said steps are carried out in the recited order. It will further be appreciated that certain processing steps, such as e.g. re-buffering, may be carried out more than once in the process of preparing the bulk substance in said first phase of the method of the invention.

The term "harvesting", as used herein, relates to a process step of obtaining a biomolecule of interest from a source that produces same. Most commercially available therapeutic proteins such as recombinant human insulin, human growth hormone, erythropoietin (EPO), blood coagulation factors, monoclonal antibodies and interferons, are for example produced by large-scale fermentation using either microorganisms such as *Bacillus subtilis* and *Escherichia coli*, yeast and other fungi, or mammalian cells as sources. Prominent examples for mammalian cell cultures as important sources of therapeutic proteins are Chinese hamster ovary (CHO) cells and baby hamster kidney (BHK) cells. Said sources can either secrete the biomolecule into the culture medium, or may express the biomolecule intracellularly. In the latter case, the harvesting procedure is typically more complex, as there is the additional requirement to disrupt the cells in order to harvest the protein. Furthermore, biomolecules can also be harvested from sources such as animal tissue, body fluids and plants.

Typical methods employed in the process of harvesting include centrifugation, filtration and microfiltration, as well as chromatography. These methods are well known in the art.

The term "purification", as used herein, relates to techniques used to isolate a biomolecule of interest. Purification is typically carried in an early phase of highly concentrated biopharmaceutical manufacturing in order to recover a highly purified drug substance for further processing, i.e. a product devoid or substantially devoid of any other substances than the biomolecule(s) of interest. Methods and steps typically performed in order to purify a biomolecule can include e.g. concentration of the biomolecule and/or clarification to remove foreign (host cell) proteins, for example via centrifugation, precipitation, filtration/ultracentrifugation or chromatographic methods such as ion exchange chromatography, affinity chromatography, hydrophobic interaction chromatography, and size-exclusion chromatography; as well as further polishing steps, e.g. for removing degradation products, product derivatives such as oxidized, deamidated, or degraded forms of product, and contaminants such as pyrogenic substances, for example via size-exclusion chromatography.

The term "re-buffering", as used herein, relates to methods for the modification of an existing formulation to obtain an adapted or optimized environment for the drug substance or the final drug product. One possible way of performing re-buffering is by diluting an existing formulation by adding e.g. water or buffers. Alternatively, an existing formulation can be modified by the addition of specific excipients, such as e.g. the excipients described herein below. A particularly preferred method of carrying out re-buffering is via dialysis. Dialysis is a well-known method in the art wherein semipermeable dialysis membranes are used to enable diffusion of small molecule solutes across the membrane, whereby the components of the liquids are exchanged and the biomolecules are retained in the dialysis cassette dependent on the molecular weight and the applied Molecular Weight Cut Off of the dialysis membrane.

The term "enrichment", as used herein, relates to the increase of concentration(s) of the respective molecule(s) (e.g. the biomolecule, the bulk substance or the biopharmaceutical drug substance or drug product, depending on the stage of manufacturing). Preferably, the concentration is increased to levels that correspond to the final concentration and dosage at which the respective, enriched product is to be used.

This first phase of the production method of the present invention is carried out in the presence of a specific composition, namely a composition comprising at least three amino acids, wherein the combination of said at least three amino acids provides at least one positively charged functional group, at least one anti-oxidative functional group, at least one osmolytic function, and at least one buffering function. This composition is also referred to herein as the "first phase composition" or the "early phase composition".

Said composition is characterized by the presence of at least three amino acids. These three amino acids are chosen such that they provide the recited four functional groups. It will be appreciated that the term "at least three amino acids" refers to three different amino acids.

The term "amino acid", as used herein, is well known in the art. Amino acids are the essential building blocks of proteins. In accordance with the present invention, the term "amino acid" refers to free amino acids which are not bound to each other to form oligo- or polymers such as dipeptides, tripeptides, oligopeptides or proteins (also referred to herein as polypeptides). They can be classified into the characteristic groups of excipients with non-polar, aliphatic; polar, uncharged; positively and/or negatively charged and/or aromatic R groups (Nelson D. L. & Cox M. M., "Lehninger Biochemie" (2005), pp. 122-127).

The amino acids in accordance with the present invention can be selected from naturally occurring amino acids as well as artificial amino acids or derivatives of these naturally occurring or artificial amino acids. Naturally occurring amino acids are e.g. the 20 proteinogenic amino acids, glycine, proline, arginine, alanine, asparagine, aspartic acid, glutamic acid, glutamine, cysteine, phenylalanine, lysine, leucine, isoleucine, histidine, methionine, serine, valine, tyrosine, threonine and tryptophan. Other naturally occurring amino acids are e. g. carnitine, creatine, creatinine, guanidinoacetic acid, ornithine, hydroxyproline, homocysteine, citrulline, hydroxylysine or beta-alanine. Artificial amino acids are amino acids that have a different side chain length and/or side chain structure and/or have the amine group at a site different from the alpha-C-atom. Derivates of amino acids include, without being limiting, n-acetyl-tryptophan, phosphonoserine, phosphonothreonine, phosphonotyrosine, melanin, argininosuccinic acid and salts thereof and DOPA. In connection with the present invention, all the terms also include the salts of the respective amino acids.

Amino acids that provide a positively charged functional group, i.e. via their corresponding side chain, are well known in the art and include, for example, lysine, arginine, histidine, and non-proteinogenic amino acids, such as for example, ornithine.

The term "amino acids that provide an osmolytic function", as used herein, relates to amino acids with that provide an osmolytic property. Such amino acids are also well known in the art and include, for example, glycine, alanine, and glutamic acid, as well as derivatives of proteinogenic and non-proteinogenic amino acids, respectively, such as for example, betaine, carnitine, creatine, creatinine, and ß-alanine.

The term "amino acids that provide an anti-oxidative functional group", as used herein, relates to amino acids that provide an anti-oxidative property via (one of) their side chain(s). Such amino acids are also well known in the art and include, for example, methionine, cysteine, histidine, tryptophan, phenylalanine, and tyrosine, as well as derivatives of proteinogenic and non-proteinogenic amino acids such as for example N-acetyl-tryptophan, N-acetyl-histidine, or carnosine.

The term "amino acids that provide a buffering function" relates to amino acids that provide a buffering capacity via one or more of their functional groups. Such amino acids are also well known in the art and include, for example, glycine, arginine, and histidine.

It will be appreciated that one amino acid may also combine several of said functional groups and/or functions, such as e.g. two, three or even all four functional groups and functions, respectively. Also envisaged herein is that the amino acids may overlap in providing such functional groups, i.e. an amino acid providing an anti-oxidative functional group may also provide a buffering function, e.g. histidine.

In certain embodiments, i.e. where the composition consists of exactly three amino acids, it is required that all four functional groups and functions, respectively are provided by said three amino acids. In other words, at least one of the amino acids provides two (or more) of the functional groups and functions, respectively. For example, glycine provides an osmolytic function as well as a buffering function, while histidine provides an anti-oxidative functional group as well as a buffering function.

In a preferred embodiment, this first phase composition consists of amino acids only, i.e. it is free of any other excipients such as e.g. sugars (including sugar alcohols), chelating agents, and anti-oxidative agents other than amino acids, surfactants, stabilizing proteins or peptides. Even more preferably, the first phase composition consists of exactly three amino acids providing the four recited functional groups and functions, respectively.

Preferred amounts of the at least three amino acids to be comprised in the first phase composition according to the invention are between 5 mg/ml and 100 mg/ml, more preferably between 10 mg/ml and 75 mg/ml, even more preferably between 15 mg/ml and 50 mg/ml and most preferably the amount is about 20 mg/ml. It will be appreciated that these preferred amounts refer to the sum of all amino acids present in the solution.

The term "about", as used herein, encompasses the explicitly recited values as well as small deviations therefrom. In other words, an amount of amino acids of "about 20 mg/ml" includes, but does not have to be exactly the recited amount of 20 mg/ml but may differ by several mg/ml, thus including for example 21 mg/ml or 19 mg/ml.

The skilled person is aware that such values are relative values that do not require a complete accuracy as long as the values approximately correspond to the recited values. Accordingly, a deviation from the recited value of for example 15%, more preferably of 10%, and most preferably of 5% is encompassed by the term "about". These deviations of 15%, more preferably of 10% and most preferably of 5% hold true for all embodiments pertaining to this invention wherein the term "about" is used.

The method of the present invention requires that the recited processing step(s) in the first phase is/are carried out "in the presence" of this first phase composition. In other words, the bulk drug substance is brought into contact with the first phase composition. This can for example be achieved if the biomolecule of interest is harvested directly into the first phase composition; by exchanging an existing solvent with the first phase composition; or by adding the at least three amino acids to an existing solvent, for example during the first purification column in the case of antibodies or during ultracentrifugation in the case of viral vectors.

The bulk drug substance obtained in this first phase is then further subjected to a second phase of further processing steps, in order to formulate the bulk drug substance into the biopharmaceutical drug product. In this second phase, at least one processing step selected from (b1) re-buffering, (b2) freezing, (b3) thawing, and (b4) filling is carried out.

The definitions and preferred embodiments provided herein above with regard to the first phase apply mutatis mutandis, unless defined otherwise. For example, the terms "comprising", "at least", "re-buffering", "dialysis", "amino acids", "in the presence of" etc. are as defined above.

The term "freezing", as used herein, relates to the process of transferring a sample into a solid, frozen state. Freezing is typically employed to prepare samples for storage, as the risk of e.g. contamination is decreased in this state.

The term "thawing", as used herein, relates to the process of transferring a sample from the solid, frozen state into a non-frozen state. In most cases, the thawed sample will be present in a liquid phase, but in those cases where a dry product was frozen, the thawed product will be returned into a dry, non-frozen state which can be subsequently reconstituted for further processsing. Once thawed, the product is available for further developmental or manufacturing processes, such as e.g. filling.

The term "filling", as used herein, relates to the process of transferring liquid or dried products into (a) special container(s) for either further processing or—as the final product—for transport, storage and/or administration.

This second phase of the production method of the present invention is again carried out in the presence of a specific composition, in this case a composition comprising at least three amino acids and one or more sugar(s). This composition is also referred to herein as the "second phase composition".

Said composition is characterized by the presence of at least three amino acids, wherein the functional groups and functions necessarily present are as defined for the first phase composition. However, the actual choice of amino acids is not limited to the same amino acids as in the first phase composition; instead, some or all of the amino acids may be different from the amino acids of the first phase composition. Also encompassed herein is that the at least three amino acids of the second phase composition are identical to the at least three amino acids of the first phase composition.

In addition, one or more sugar(s) is/are present in the second phase composition.

The term "sugar", as used herein, refers to any types of sugars, i.e. the monosaccharide, disaccharide or oligosaccharide forms of carbohydrates as well as sugar alcohols. Examples of suitable sugars include, without being limiting, trehalose, saccharose, mannitol, and sorbitol.

Preferred amounts of sugars to be comprised in the solution according to the invention are between 5 and 200 mg/ml, more preferably between 10 and 100 mg/ml, even more preferably between 15 and 80 mg/ml, and most preferably, the amount is about 30 mg/ml. Where a mixture of different types of sugars is employed, these preferred amounts refer to the sum of all sugars in the solution.

In accordance with the present invention, the ratio between said amino acids and sugar(s) present in the second phase composition is between 10:1 and 1:100. This ratio refers to the concentration of the amino acids and the sugar(s), which is typically presented in mg/ml. Preferably, the ratio is between 5:1 to 1:50 (w/w), more preferably between 2.5:1 (w/w) and 1:25 (w/w), and most preferably between 1:1 and 1:2 (w/w).

In accordance with the present invention, an improved method for the production of low viscous and highly concentrated biopharmaceutical drug products has been developed. This method was developed with a focus on providing simple but efficient protection throughout the entire production process, combined with a reduced need for repeated, step-dependent changes in the supporting composition. To this end, a simple amino acid composition is employed in the early phase of the method. Surprisingly, this amino acids composition was found to be sufficient to stabilize the bulk drug substance immediately after harvesting and during the initial purification steps. Moreover, it was found that stabilizing the drug substance already at these early stages results in improved product quality and stability throughout the entire manufacturing process, storage and administration.

The method provides the additional advantage that the stabilizing composition in the early phase of the method during the production of the low viscous and highly concentrated bulk drug substance solely requires the presence of a small number of amino acids, i.e. three amino acids (or optionally more) which do not disturb during the typically required analytical procedures during drug substance development.

These findings are particular surprising, as previous work such as e.g. WO 2013/001044, WO 2010/115835, WO 2010/112576, WO 2013/001034 or WO 2015/059284 had shown that various combinations of amino acids—with or without further stabilizing excipients—provide protective effects on the three dimensional structure of the particular biomolecules under different stress conditions. These stress conditions were, for example, the drying and/or re-constituting of biomolecules, during storage at high temperatures as well as during the sterilization of biomolecules. However, whereas these compositions work well under these stress conditions, it was surprisingly found herein that not all of these compositions provide the same superior effects as the "early phase composition" according to the invention when employed already in the early phase of highly concentrated bulk substance preparation, for example directly upon harvesting from cell culture systems, for example after the first ultracentrifugation step.

As shown in e.g. example 2 below, the early addition of the "early phase" stabilizing composition can have a strong impact on the stability of the highly concentrated biopharmaceutical drug product during its entire preparation procedure. Thus, the early application of the stabilizing composition according to the invention was found to have a pronounced stabilizing effect on the particular biomolecule during the entire production process.

These findings are further substantiated in e.g. examples 3 and 5, which show the stabilizing efficacy of several compositions according to the invention against exposure of stresses usually involved in processing steps during the production process, such as e.g. re-buffering using dialysis or the concentration of a final low viscous and highly concentrated therapeutic antibody formulation. Highly concentrated therapeutic antibody formulations (example 3) were found to show decreased formation of aggregates when prepared in various compositions according to the invention.

Moreover, as shown in example 5, increasing the concentration of the commercially available liquid trastuzumab formulation to a concentration of 200 mg/ml in order to prepare highly concentrated liquid therapeutic antibody formulations resulted in an unwanted increase in the formation of aggregates. In contrast, the concentration of this therapeutic antibody subsequent to an additional re-buffering step in the compositions according to the present invention was sufficient to avoid this increase in aggregate formation. In examples 6, 7, and 8 further data is shown confirming the stabilizing efficacy of the compositions according to this invention during biopharmaceutical manufacturing and processing steps. The examples show that the compositions according to the invention were superior over the original supplier liquid formulation when the monoclonal antibody trastuzumab was stressed during rebuffering and subsequent concentration steps and stirring as a model for mechanical stress.

The above mentioned examples as models for re-buffering, dialysis and concentration during different production steps of the drug substance show that the stabilizing efficacy of the inventive compositions during this early phase does not particularly depend on the concentration ratios between amino acids and sugars. Surprisingly, in the later downscaling processing phase, the concentration ratios of amino acids to sugar (or sugar mixtures) and/or the concentration ratios of amino acids to drug substance, elicit strong drug product stabilizing efficacy e.g. during liquid storage, liquid storage at elevated temperatures (see e.g. examples 3 to 5), and on the viscosity, particularly in the case of highly concentrated antibody formulations (see e.g. examples 3 and 5).

The simplicity of the stabilizing amino acid composition in the early phase of the method has the further advantage that it can be easily adjusted to the requirements of the drug substance during the further processing steps to obtain the respective drug product. Modifications of the initial simple stabilizing formulation by means of e.g. adding other excipients, such as sugars and/or sugar mixtures enable the easy adjustment to the final formulation by avoiding or limiting additional re-buffering steps. Thus, less handling and fewer stressful processing steps are required throughout the entire production and formulation process, thereby reducing the stress applied and increasing the stability of the highly concentrated biopharmaceutical drug product, but also reducing work and cost associated with highly concentrated biopharmaceutical drug substance and drug product manufacturing.

In addition, the use of the compositions described herein during the production process(es) as claimed leads to an osmolality of the final highly concentrated biopharmaceutical drug product that is below 450 mOsmol/kg. High osmolality has been reported by several investigators to be associated with pain and side effects at the injection site. Thus, it is generally accepted that the osmolality of a parenterally applied solution should be below 450 mOsmol/kg, preferably close to the physiological range of 275 to 320 mOsmol/kg. The drug product obtained by the method of the present invention fulfills this requirement for low viscous and highly concentrated pharmaceutical drug products for administration to humans and animals.

In summary, the present inventors surprisingly found that employing the early phase composition of the present invention, which is based on a very simple amino acid composition, provides an ideal starting point for the subsequent processing steps required in low viscous and highly concentrated biopharmaceutical drug substance and drug product preparation. Using this early phase composition as a basis, a modular and development phase-specific formulation approach is possible that solely requires minimal adjustments of the compositions while at the same time achieving well balanced stabilization effects. The thus balanced formulations may be specifically tailored according to the specific requirements of the subsequent steps, such as the different storage and/or administration purposes for a particular low viscous and highly concentrated biopharmaceutical drug product.

The preferred compositions which are used during the early phase of drug substance production according to the present invention comprise the amino acids arginine, glycine, tryptophan, and/or histidine. The late phase composition also comprises arginine, glycine, tryptophan and/or histidine whereas the amino acids are in combination with a sugar or sugar mixture such as trehalose and saccharose, and optionally chelating agent and/or antioxidants.

In a preferred embodiment of the method of the invention, the low viscous and highly concentrated biopharmaceutical drug product obtained in (b) is further processed for storage and/or administration as a liquid formulation.

"Storage", in accordance with the present invention, means that the highly concentrated drug substance or drug product which is not immediately used for subsequent processing steps or administration to a subject is kept under defined conditions. Accordingly, the term "storage", as used herein, is not particularly limited and encompasses for example storage of the drug substance or drug product at the manufacturing site, at a research lab, at a medical institute or practice prior to use, the transport/shipment of the drug substance or drug product but also preparatory steps, such as e.g. aliquoting of the highly concentrated biopharmaceutical product.

The conditions for storage depend on the type of drug substance or drug product, as well as on the intended route of administration if the product is for administration. For example, sterility and stability of the drug product ought to be considered and controlled. Many drug substances have to be kept cold and/or in the dark to prevent temperature or UV-light mediated degradation processes, respectively. In addition, drug products that are to be administered as liquid formulations are preferably kept as a liquid until use, in order to avoid having to carry out an additional reconstitution step prior to application.

The highly concentrated biopharmaceutical drug product can be processed for storage and/or administration by any suitable processing step. Non-limiting examples of such processing steps include e.g. aseptic filling, i.e. filling wherein the formulation is transferred into pre-prepared sterile containers, such that the low viscous and highly concentrated biopharmaceutical drug product is suitable for later administration procedures. In case of a liquid formulation, the concentration of the low viscous and highly concentrated biopharmaceutical drug product, e.g. upon filling, is preferably chosen such that it corresponds to the final concentration required for administration. Moreover, it is particularly preferred that the formulation is chosen such that it stabilizes the product and, thus, avoids or minimizes the loss of molecular integrity and function during filling, storage, and administration.

In case that the biopharmaceutical drug product is present as a frozen product, said frozen product has to be thawed before filling. The resulting liquid has to be aliquoted in portions into the final dosage. It has to be considered at this stage that freeze and thaw may lead to a loss of molecular integrity and functionality, so that the final dosage might have to be adjusted accordingly.

In accordance with this preferred embodiment of the method of the invention, the low viscous and highly concentrated biopharmaceutical drug substance or drug product is processed into a liquid formulation. Said liquid formulation can be stored and/or provided for administration in any suitable vial or container or carrier, such as e.g. experimental or freezer tubes, syringes, dispensers, etc.

Typically, the storage of biopharmaceutical drug products is carried out under defined conditions. Such defined conditions include for example specific temperature profiles, humidity and other storage conditions, as for example prescribed by the "good storage practice" guidelines of the US Food and Drug Administration (FDA) and in the guidelines of the International Council for Harmonization of Technical Requirements for Pharmaceuticals for Human Use (ICH). However, problems can arise during transport/shipment of the biopharmaceutical drug product but also during administration, where it might not always be possible to observe such stringent conditions. For example, the cold-chain can become interrupted on transport, in particular into third-world countries, the samples might become exposed to light or they may be exposed to mechanical stresses due to agitation. This is of particular importance with regard to liquid formulations, which are more susceptible to damage due to such adverse conditions than dried formulations.

The stability and viscosity of highly concentrated biopharmaceutical drug products during storage depends in part on the observation of the above described storage conditions, but is also influenced by the presence of appropriate stabilizing excipients, as well as the nature and concentration of the biopharmaceutical drug product itself. Thus, by providing the low viscous and highly concentrated biopharmaceutical drug product in an appropriate liquid formulation can protect the highly concentrated biopharmaceutical drug product from adverse conditions, thereby enhancing its stability and maintaining low viscosity.

Accordingly, in a preferred embodiment of the method of the invention, the liquid formulation is for the storage and/or administration of the low viscous and highly concentrated biopharmaceutical drug product at a concentration ranging from 100 to 500 mg/ml, wherein the formulation is characterized in that it comprises (i) at least three amino acids, wherein the combination of said at least three amino acids provides at least one positively charged functional group, at least one antioxidative functional group, at least one osmolytic function, and at least one buffering function, and (ii) one or more sugar(s); and wherein the ratio between the amino acids and the sugar is adjusted to between 4:1 and 1:1 (w/w).

This preferred embodiment relates to the storage of a biopharmaceutical drug product in liquid form at a high concentration and low viscosity. As defined herein above, such high concentrations are concentrations of the biopharmaceutical drug product that are between 100 and 500 mg/ml. In accordance with this embodiment, the liquid formulation is a formulation that has a viscosity of less than 25 mPa*s.

In order to provide an improved stability and low viscosity of such high concentration liquid formulations, the formulation is adjusted such that it comprises at least three amino acids and one or more sugar(s). The definitions and preferred embodiments for the "at least three amino acids" and the "sugar(s)" are as provided herein above with regard to the method of the invention.

Again, the actual choice of amino acids is not limited to the same amino acids as in the compositions defined herein above; instead, some or all of the amino acids may be different from the amino acids of the above defined compositions. Also encompassed herein is that the at least three amino acids of this preferred embodiment are identical to the at least three amino acids of one of the above defined compositions. The same applies with regard to the sugar(s).

Importantly, the ratio between the amino acids and the sugar is to be adjusted to between 4:1 to 1:1 (w/w), including e.g. 3:1 (w/w) and 2:1 (w/w). Most preferably, the ratio is 1:1 (w/w). Methods for adjusting the ratio are known in the art, as discussed above. Preferably, the adjustment is carried out by adjusting the weight to weight ratios between the amino acids and the sugar. Based on the knowledge of the amounts of excipients already present in the solution and the known molecular weight(s) thereof, it can be calculated how much additional excipient needs to be added to obtain the recited ratio used in the dilutions.

Also envisaged in accordance with this preferred embodiment of the method of the invention is that additional excipients may be comprised in the liquid formulation. Such additional excipients are preferably selected from chelating agents, additional anti-oxidative agents and surfactants.

The term "chelating agents", as used herein, relates to excipients that trap metal ions in formulations to avoid e.g. metal ion-catalyzed oxidative reactions within a formulation. Non-limiting examples of chelating agents include desferal, diethyltriaminepentaactic acid (DTPA), ethylenediaminetetraacetic acid (EDTA), or deferoxamine (DFO). Whereas such chelating agents are commonly used in chelation therapy to detoxify poisonous metal agents such as mercury [Hg], arsenic [As], and lead [Pb] by converting them to a chemically inert form that can be excreted without further interaction with the body, it will be understood that the chelating agents are used in accordance with the present invention in low concentrations, e.g. between 0.3 and 0.5 mg/ml, that will not elicit a therapeutic effect, but rather stabilize the biopharmaceutical products during e.g. storage.

The term "additional anti-oxidative agents", as used herein, relates to methionine, cysteine, glutathion, tryptophan, histidine, ascorbic acid and any derivatives of the herein listed agents, without being limiting.

The term "surfactants", as used herein, relates to surface-active agents. This term also includes wetting agents, emulsifying agents and suspending agents, depending on their properties and use. Surface-active agents are substances which, at low concentrations, adsorb onto the surfaces or interfaces of a system and alter the surface or interfacial free energy and the surface or interfacial tension. Because they are soluble in both organic solvents and water, they are called "amphiphilic". Preferred surfactants in accordance with the present invention include, without being limiting, polysorbate 20 (Tween 20) and polysorbate 80 (Tween 80).

As shown in Examples 3 to 5 below, it was surprisingly found that combining the biopharmaceutical drug product, e.g. a highly concentrated therapeutic antibody formulation obtained by the method of the invention, with the recited at least three amino acids and sugar at a ratio of amino acids to sugar of between 4:1 to 1:1 (w/w) results in less aggregation during processing of the therapeutic antibody, particularly during re-buffering by dialyisis and/or concentration, compared to the original supplier formulation. Moreover, this formulation reduced aggregation and also fragmentation during subsequent liquid storage at elevated temperature. Examples 6 and 7 further confirm this finding. For example, when compared to the preferred formulation outlined in the patent U.S. Pat. No. 9,364,542 B2 we underlined superior stabilization efficacy of our formulations according to the present invention as well as in comparison with the original liquid supplier Moreover, quantitative statistical analyses of the liquid storage time kinetics during storage revealed that the stabilizing effects due to the compositions according to this invention were statistically significant.

Most importantly, such liquid formulations of highly concentrated biopharmaceutical product were surprisingly found in Examples 3 and 5 to have particularly low viscosities, a factor that is of great importance for e.g. the syringeability of the final product for administration. In particular, Example 3 showed a highly concentrated therapeutic antibody formulation corresponding to the present invention and containing the respective antibody in concentrations of 120 mg/ml with viscosities remarkably smaller than 4 mPa*s compared the measured viscosity in the original supplier formulation (approximately 5 mPa*s. Furthermore, in Example 5 the highly concentrated therapeutic antibody formulations corresponding to the present invention and containing the antibody in concentrations of 200 and 220 mg/ml revealed viscosities significantly smaller than 20 mPa*s.

Overall, in all embodiments, viscosity was found to be lower than in the original supplier formulations. These values are therefore lower as in corresponding prior art formulations.

Accordingly, in particularly preferred embodiments of this embodiment of storage of a biopharmaceutical drug product in liquid form at a high concentration, the viscosities of the highly concentrated biopharmaceutical drug products are below 20 mPa*s. It is even more preferred that where the concentration of the highly concentrated biopharmaceutical drug product is >200 mg/ml, the viscosity is <20 mPa*s; where the concentration of the highly concentrated biopharmaceutical drug product is between 100 mg/ml and 120 mg/ml, the viscosity is <4; where the concentrations of the highly concentrated biopharmaceutical drug product is between 120 mg/ml and 150 mg/ml, the viscosity is <8 mPa*s; and where the concentration of the highly concentrated biopharmaceutical drug product is between 150 mg/ml and 220 mg/ml, the viscosity is <20 mPa*s.

In an even more preferred embodiment of this method of the invention, the liquid formulation is further adjusted such that the ratio between the biomolecule of interest and the at least three amino acids of (i) is between 3.5:1 (w/w) to 1:2 (w/w). Adjustment of the ratio is preferably done as a weight to weight ratio. The details provided herein above with regard to adjusting the ratio between biomolecule of interest and sugar(s) apply mutatis mutandis to this embodiment regarding the additional adjustment of ratio between biomolecule of interest and the at least three amino acids.

In a preferred embodiment, the ratio between amino acids and sugar is between 10:1 and 1:100. Moreover, the preferred ratio between biomolecules and excipients is between 1:1 and 1:500. These ratios are also preferred in the other embodiments.

In a preferred embodiment of this method of invention, the liquid formulation for highly concentrated drug substances do not comprise proline. Example 6 substantiated that the stabilizing efficacy according to the invention was superior over formulations containing proline according to U.S. Pat. No. 9,364,542 B2. This was confirmed by limited chemical degradation as analyzed by means of CEX-HPLC.

Preferably, the composition in step (a) contains between 0.5 mg/ml and 10 mg/ml tryptophan and between 0.5 mg/ml and 30 mg/ml histidine.

As is shown in Examples 2 to 5 the solutions in a balanced weight:weight ratio between tryptophan and histidine resulted in increased stability of the drug substance and in combination with sugar in increased stability of the drug substance.

In another preferred embodiment of the method of the present invention, the biomolecule of interest is selected from the group consisting of proteins and peptides, as well as mixtures thereof.

Thus, in accordance with a more preferred embodiment of the method of the invention the biomolecule of interest is an antibody.

The term "peptide", as used herein, describes a group of molecules consisting of up to 30 amino acids, whereas "proteins" consist of more than 30 amino acids. Peptides and proteins may further form dimers, trimers and higher oligomers, i.e. consisting of more than one molecule which may be identical or non-identical. The corresponding higher order structures are, consequently, termed homo- or heterodimers, homo- or heterotrimers etc. The terms "peptide" and "protein" (wherein "protein" is interchangeably used with "polypeptide") also refer to naturally modified peptides/proteins wherein the modification is effected e.g. by glycosylation, acetylation, phosphorylation and the like. Such modifications are well-known in the art. Furthermore, peptidomimetics of such peptides and proteins where amino acid(s) and/or peptide bond(s) have been replaced by functional analogues are also encompassed herein. Such functional analogues include all known amino acids other than the 20 gene-encoded amino acids, such as selenocysteine. Specific, preferred, examples of suitable proteins or peptides are detailed herein below.

Preferred examples of proteins and peptides are antibodies and hormones.

An antibody in accordance with the present invention can be, for example, a polyclonal or monoclonal antibody. The term "antibody", as used herein, also includes embodiments such as chimeric (human constant domain, non-human variable domain), single chain and humanized (human antibody with the exception of non-human CDRs) antibodies, as well as antibody fragments, like, inter alia, Fab, Fab', Fd, F(ab')2, Fv or scFv fragments or nanobodies, i.e. single monomeric variable antibody domains; see, for example, Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999.

Techniques for the production of antibodies are well known in the art and have been described, e.g. in Harlow and Lane (1988) and (1999), loc. cit.

In accordance with an even more preferred embodiment of the method of the invention the antibody is a therapeutic antibody.

The term "therapeutic antibody" as used herein, describes monoclonal antibodies (mAb) to bind monospecifically to certain cells or proteins, e.g. in order to stimulate the immune system and/or to attack cells of a patient for therapeutic purposes.

Non-limiting examples of preferred antibodies and in particular therapeutic antibodies include Infliximab, Bevacizumab, Ranibizumab, Cetuximab, Ranibizumab, Palivizumab, Abagovomab, Abciximab, Actoxumab, Adalimumab, Afelimomab, Afutuzumab, Alacizumab, Alacizumab pegol, ALD518, Alemtuzumab, Alirocumab, Alemtuzumab, Altumomab, Amatuximab, Anatumomab mafenatox, Anrukinzumab, Apolizumab, Arcitumomab, Aselizumab, Altinumab, Atlizumab, Atorolimiumab, tocilizumab, Bapineuzumab, Basiliximab, Bavituximab, Bectumomab, Belimumab, Benralizumab, Bertilimumab, Besilesomab, Bevacizumab, Bezlotoxumab, Biciromab, Bivatuzumab, Bivatuzumab mertansine, Blinatumomab, Blosozumab, Brentuximab vedotin, Briakinumab, Brodalumab, Canakinumab, Cantuzumab mertansine, Cantuzumab mertansine, Caplacizumab, Capromab pendetide, Carlumab, Catumaxomab, CC49, Cedelizumab, Certolizumab pegol, Cetuximab, Citatuzumab bogatox, Cixutumumab, Clazakizumab, Clenoliximab, Clivatuzumab tetraxetan, Conatumumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Ecromeximab, Eculizumab, Edobacomab, Edrecolomab, Efalizumab, Efungumab, Elotuzumab, Elsilimomab, Enavatuzumab, Enlimomab pegol, Enokizumab, Enokizumab, Enoticumab, Enoticumab, Ensituximab, Epitumomab cituxetan, Epratuzumab, Erlizumab, Ertumaxomab, Etaracizumab, Etrolizumab, Exbivirumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fuiranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lebrikizumab, Lemalesomab, Lerdelimumab, Lexatumumab, Libivirumab, Ligelizumab, Lintuzumab, Lirilumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pintumomab, Placulumab, Ponezumab, Priliximab, Pritumumab, PRO140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Tefibazumab, Telimomab aritox, Tenatumomab, Teneliximab, Teplizumab, Teprotumumab, TGN1412, Tremelimumab, Ticilimumab, Tildrakizumab, Tigatuzumab, TNX-650, Tocilizumab, Toralizumab, Tositumomab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vapaliximab, Vateliziumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

In accordance with another even more preferred embodiment of the method of the invention the antibody is a diagnostic antibody.

The term "diagnostic antibody", as it is used herein, describes antibodies that are conjugated e.g. with a radio-label, fluorescent label, or color-forming enzyme and are used as a "probe" to biologic target structures for diagnostic purposes. Possible applications include pregnancy tests, immunoblotting, ELISA and immunohistochemical staining without being limiting.

In accordance with a further even more preferred embodiment of the method of the invention the antibody is an antibody for experimental purposes.

The term "antibody for experimental purposes", as it is used herein, describes antibodies that are not suitable for therapeutic or diagnostic purposes, but can be used for targeting biological structures e.g. in cell cultures or on histological preparations in research.

The term "hormones", as used herein, is well known in the art and relates to a group of therapeutic biomolecules used for the treatment of metabolism disorders. Non-limiting examples include teriparatide or estrogen. Teriparatide is a recombinant form of the growth hormone parathyroid hormone that is commonly used for the treatment of impaired bone metabolism such as osteoporosis. Estrogen is commonly used for the therapy of menopausal disorders and is given in conjunction with progesterone to reduce the risk for uterine cancer.

In a more preferred embodiment of the method of the present invention, the biomolecule of interest is an antigen, such as e.g. an antigen for use as vaccines.

As used herein, the term "antigens" refers to molecules capable of inducing an immune response in a host organism. Typically, antigens are proteins and polysaccharides. However, when combined with proteins and polysaccharides, also lipids or nucleic acids can be antigenic. Antigens are often derived from parts of bacteria, viruses, and other microorganisms, such as e.g. their coats, capsules, cell walls, flagella, fimbrae, or toxins. Antigens can also be non-microbial, such as e.g. self-antigens or exogenous (non-self) antigens such as pollen, egg white, or proteins from transplanted tissues/organs or on the surface of transfused blood cells. In accordance with the present invention, the term "antigens" includes, without being limiting, (i) antigens represented by one particular molecular type of antigen, such as e.g. one particular protein; (ii) antigen mixtures of different molecular types of antigen, such as e.g. a mixture of different proteins or a mixture of proteins with polysaccharides; as well as (iii) antigen preparations comprising further components, such as e.g. in split-virus antigens, which are preparations wherein a virus has been disrupted by e.g. a detergent, or another method, without further removal of other viral components.

Preferably, the antigens are for use as vaccines. Suitable antigens for vaccine preparation are well known in the art and the considerations for choosing an antigen for vaccine production commonly applied in the art apply mutatis mutandis with regard to choosing a suitable antigen for use as a vaccine in accordance with the present invention. Accordingly, antigens already available in the art, as well as novel antigens, may be employed.

Particularly preferred examples of antigens are subunit antigens or viral vectors, including e.g. virus like particles and life viruses.

Hence, in accordance with a more preferred embodiment of the method of the invention the biomolecule of interest is a viral vector.

"Viral vectors" are complex supramolecular ensembles of macromolecules which are prone to a variety of chemical and physical degradation pathways upon manufacturing, storage and distribution. The term "viral vector", in accordance with the present invention, relates to a carrier, i.e. a "vector" that is derived from a virus. "Viral vectors" in accordance with the present invention include vectors derived from naturally occurring or modified viruses, as well as virus like particles (VLPs). When viruses are the starting material for the development of a vector, certain requirements such as safety and specificity, need to be fulfilled in order to ensure their suitability for clinical use in animals or in human patients. One important aspect is the avoidance of uncontrolled replication of the viral vector. This is usually achieved by the deletion of a part of the viral genome critical for viral replication. Such a virus can infect target cells without subsequent production of new virions. Moreover, the viral vector should have no effect or only a minimal effect on the physiology of the target cell and rearrangement of the viral vector genome should not occur. Such viral vectors derived from naturally occurring or modified viruses are well known in the art and non-limiting examples of commonly employed viral vectors include as e.g. Modified Vaccinia Ankara (MVA) virus or Adenovirus. Also vectors derived from virus like particles are well known in the art and have been described, e.g. in Tegerstedt et al. (Tegerstedt et al. (2005), Murine polyomavirus virus-like particles (VLPs) as vectors for gene and immune therapy and vaccines against viral infections and cancer. Anticancer Res. 25(4):2601-8.). One major advantage of VLPs is that they are not associated with any risk of reassembly as is possible when live attenuated viruses are used as viral vectors and, as such, they represent "replication-deficient viral vectors" in accordance with the present invention. VLP production has the additional advantage that it can be started earlier than production of traditional vaccines once the genetic sequence of a particular virus strain of interest has become available.

VLPs contain repetitive high density displays of viral surface proteins which present conformational viral epitopes that can elicit strong T cell and B cell immune responses. VLPs have already been used to develop FDA approved vaccines for Hepatitis B and human papillomavirus and, moreover, VLPs have been used to develop a pre-clinical vaccine against chikungunya virus. Evidence further suggests that VLP vaccines against influenza virus might be superior in protection against flu viruses over other vaccines. In early clinical trials, VLP vaccines for influenza appeared to provide complete protection against both the Influenza A virus subtype H5N1 and the 1918 flu.

In a further preferred embodiment of the method of the invention, the method further comprises adding an adjuvant to the biopharmaceutical drug product.

The term "adjuvant", as used herein, relates to one or more compounds that enhance the recipient's immune response to a vaccine. Adjuvants are often added to promote an earlier, more potent response, and/or more persistent immune response to the vaccine, which often allows for a lower vaccine dosage. Non-limiting examples of adjuvants include e.g. aluminium hydroxide and aluminium phosphate, the organic compound Squalene but also compounds such as e.g. ligands of the Toll-like receptors, QS21, aluminium hydroxide derivates, oil immersions, Lipid A and it's derivates (e.g. monophosphoryl lipid A (MPL), CpG motives, poly I:C dsRNA, Muramyldipeptid (MDP), Freund's Complete Adjuvant (FCA, for non-human use only), Freund's incomplete Adjuvant (FIA, for non-human use only) or MF59C. Such adjuvants are well known in the art.

In another preferred embodiment of the method of the invention, the final highly concentrated biopharmaceutical formulation is further adjusted for intramuscular, subcutaneous, intradermal, transdermal, application. For these administration routes, osmolality, viscosity, injectability, and syringeability have to be considered. For example, low numbers of excipients are preferred to limit osmolality and viscosity in order e.g. to reduce pain and adverse events at the injection site.

As discussed herein above, the use of the compositions described herein during the production process(es) as claimed leads to an osmolality of the final low viscous and highly concentrated biopharmaceutical drug product that is below 450 mOsmol/kg. High osmolality has been reported by several investigators to be associated with pain and side effects at the injection site. Thus, it is generally accepted that the osmolality of a parenterally applied solution should be below 450 mOsmol/kg, preferably close to the physiological range of 275 to 320 mOsmol/kg. The drug product obtained by the method of the present invention fulfills this requirement for pharmaceutical drug products for administration to humans and animals.

The present invention further relates to a low viscous and highly concentrated biopharmaceutical drug product obtained or obtainable by the method of the invention.

In a preferred embodiment of the low viscous and highly concentrated biopharmaceutical drug product of the invention, said product is for use in intramuscular, subcutaneous, intradermal, transdermal, application. In another preferred embodiment of the low viscous and highly concentrated biopharmaceutical drug product of the invention, said product is for research, therapeutic and/or prophylactic purposes. More preferably, the drug product is for use in vaccination.

The vaccines formulated in accordance with this invention elicit thermal stability and therefore, can undergo prolonged storage and transport even in situations where the cold-chain is not guaranteed. Moreover, the higher stability of the drug products may reduce or avoid adjuvants which are known by the person skilled in the art to be essential for sufficient vaccination effects.

Unless otherwise defined, all technical and scientific terms used herein have the same meaning as commonly understood by one of ordinary skill in the art to which this invention belongs. In case of conflict, the patent specification, including definitions, will prevail.

Regarding the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The above considerations apply mutatis mutandis to all appended claims. To give a non-limiting example, the combination of claims 10, 6 and 1 is clearly and unambiguously envisaged in view of the claim structure. The same applies for example to the combination of claims 10, 2 and 1, etc.

The figures show:

FIG. 1: In vitro infectivity of highly concentrated adenoviral vectors after freeze drying in different formulations as a model for stability under thermal stress. Adenoviral vector preparations were formulated by dilution and subsequently freeze-dried in composition 1 and 2. After reconstitution of the freeze-dried vectors an in vitro infectivity assay in HEK 293 cells was carried out using an antibody based colorimetric detection of the adenoviral Hexon protein to indicate a successful amplification of the adenovirus in the infected cells. A complete retention of the infective titers of the adenoviral vector preparations formulated in composition 1 and 2 was observed (infective units per ml as compared to positive control; depicted as dashed line). In contrast, freeze drying of the adenoviral vectors diluted in the original supplier formulation led to a remarkable loss of the infective titers and freeze drying of the adenoviral vectors diluted in PBS resulted in a complete loss of the corresponding infective titers.

Figure 2:
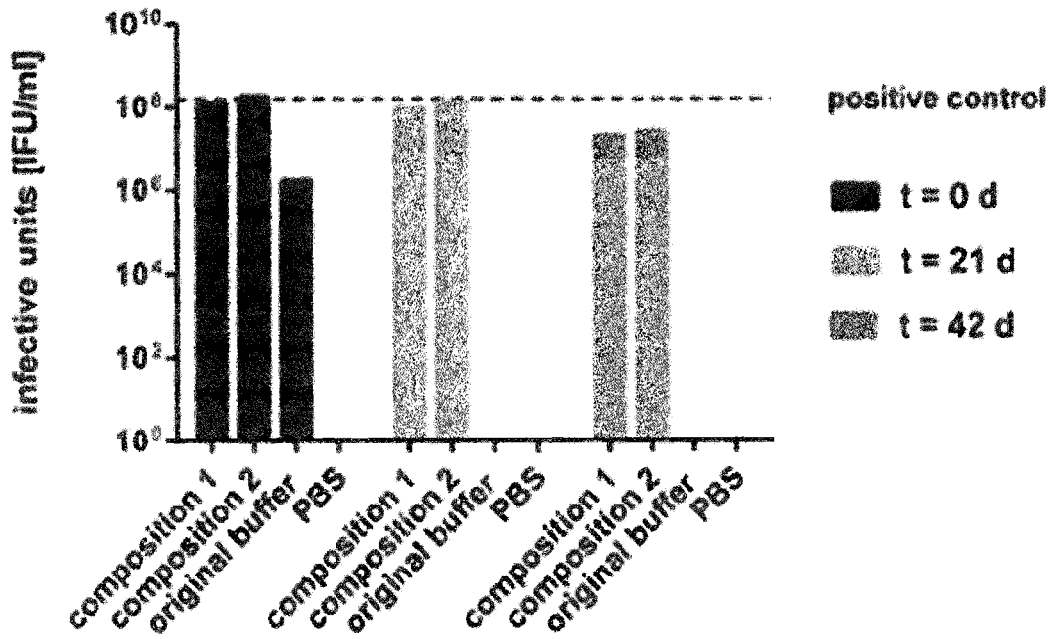
Figure 2:
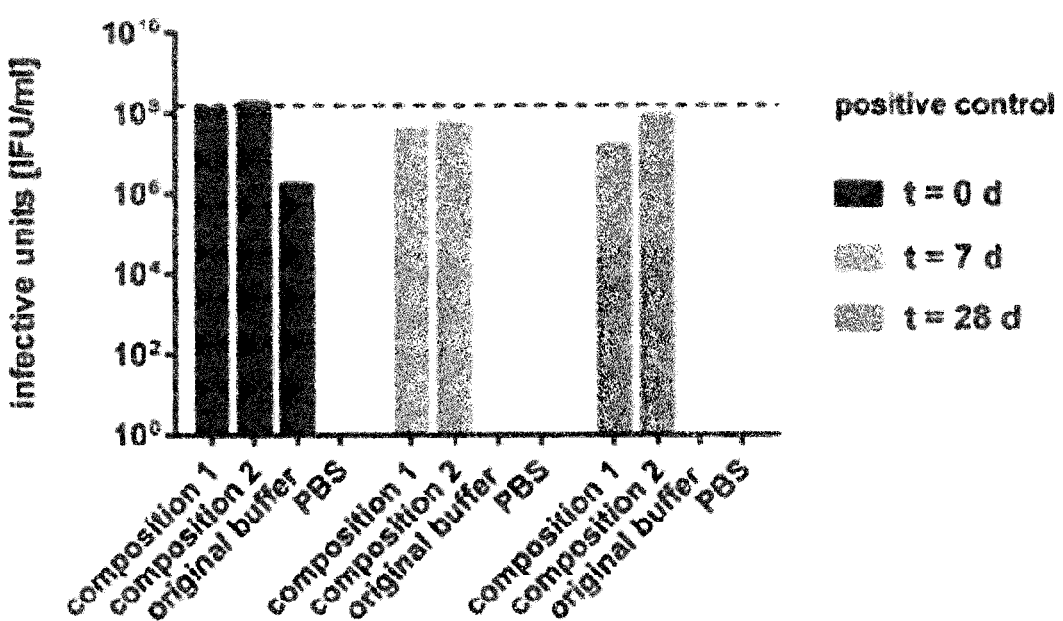

FIG. 2: In vitro infectivity of highly concentrated adenoviral vectors after freeze drying in different formulations and subsequent storage of the dried formulations at elevated temperatures as a model for stability under thermal stress. t=0 d (black bars on the left) shows the in vitro infectivity directly after freeze drying and reconstitution before storage. The dashed line shows the corresponding infective titer of the untreated positive control. (A) In vitro infectivity of the adenoviral vector compositions after re-buffering by dilution in composition 1 and 2 and subsequent storage of the freeze-dried formulations for 21 days (set of bars in the middle) and 42 days (set of bars on the right) at 25° C. and at 60% residual humidity, as compared to the original supplier buffer and PBS. (B) In vitro infectivity of the adenoviral vector compositions after re-buffering by dilution in composition 1 and 2 and subsequent storage of the freeze-dried formulations for 7 days (set of bars in the middle) and 28 days (set of bars on the right) at 40° C. and at 75% residual humidity, as compared to the original supplier buffer and PBS. Complete retention of the adenoviral infectivity was observed in the samples prepared in the compositions 1 and 2, whereas storage in either the original supplier buffer or in PBS led to the complete loss of adenoviral infectivity.

Figure 3:
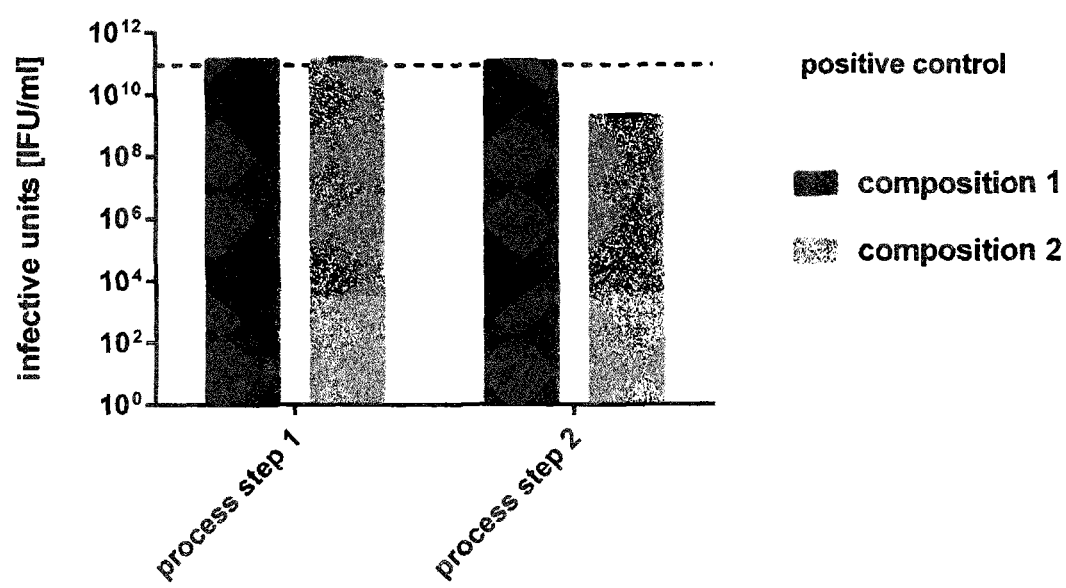

FIG. 3: In vitro infectivity of highly concentrated adenoviral vector preparations after formulation in stabilizing compositions 1 and 2 prepared during either process step 1 or process step 2 as a stability model during processing. Adenoviral preparations were re-buffered by dialysis in composition 1 and 2, respectively either directly after the purification step by CsCl density ultracentrifugation (process step 1), or later in the preparation process (process step 2). In process step 1, a complete retention of the infective titer after dialysis in both compositions was observed compared to the positive control (depicted as dashed line). In contrast, dialysis during process step 2 led to a remarkable loss of infective titers of nearly two log levels when carried out in composition 2, whereas dialysis in composition 1 led to the complete retention of the infective titer, similar to the results obtained for process step 1.

Figure 4:
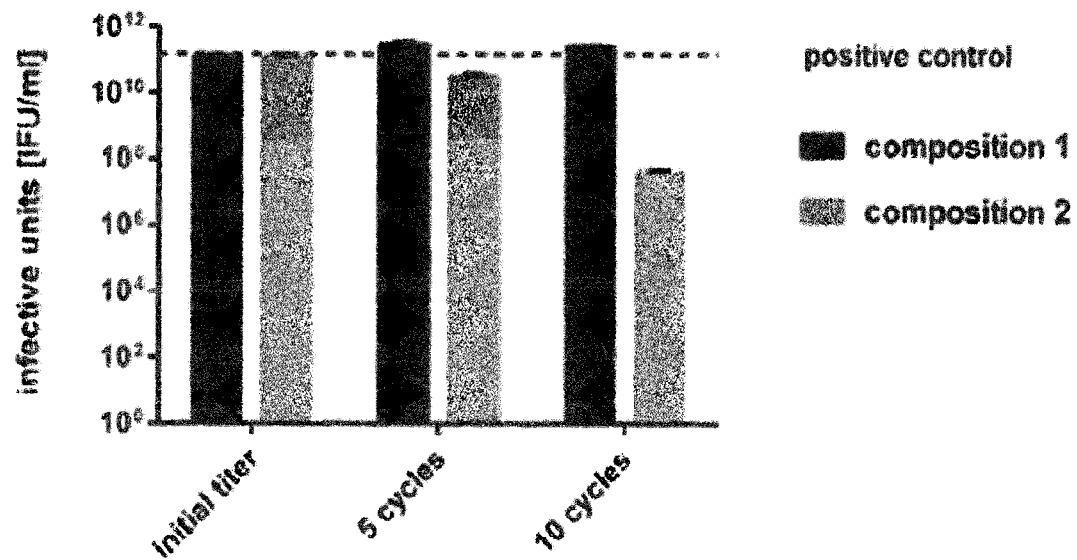
Figure 4:
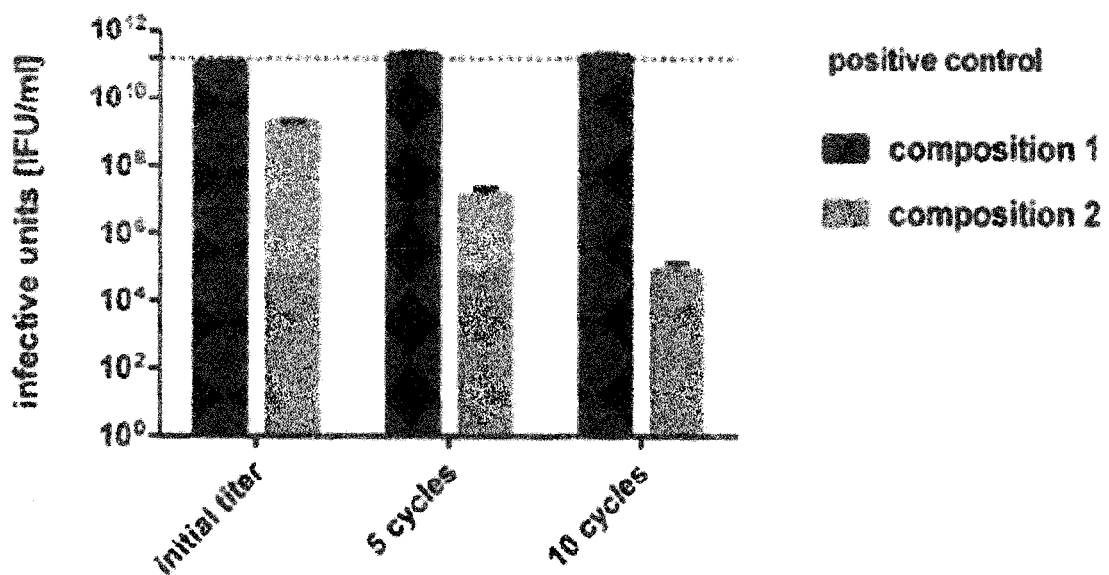

FIG. 4: In vitro infectivity of the highly concentrated adenoviral vector preparations after repeatedly applied freeze and thaw cycles as a stability model during thermal stress and processing. (A) Re-buffering of the adenoviral vector preparations by dialysis during preparation in process step 1. (B) Re-buffering of the adenoviral vector preparations by dialysis during preparation in process step 2. In both preparation procedures (process step 1 and 2), re-buffering in composition 1 led to the complete retention of the infectivity directly after dialysis (initial titer) and after application of 5 and 10 freeze and thaw cycles (A) and (B) compared to the positive control depicted as dashed line. Re-buffering in composition 2 during an earlier step of the preparation process (process step 1) led also to complete retention of the infectivity directly after dialysis (initial titer; A, left set of bars) and minor loss of the infective titer after application of repeated freeze and thaw cycles (A). In contrast, re-buffering in composition 2 during preparation in process step 2 led to a remarkable reduction in the infective titer already directly after the dialysis (B; left set of bars). Further application of repeated freeze and thaw cycles resulted in a further, significant decrease of the infective titer (B; middle and right set of bars).

Figure 5:
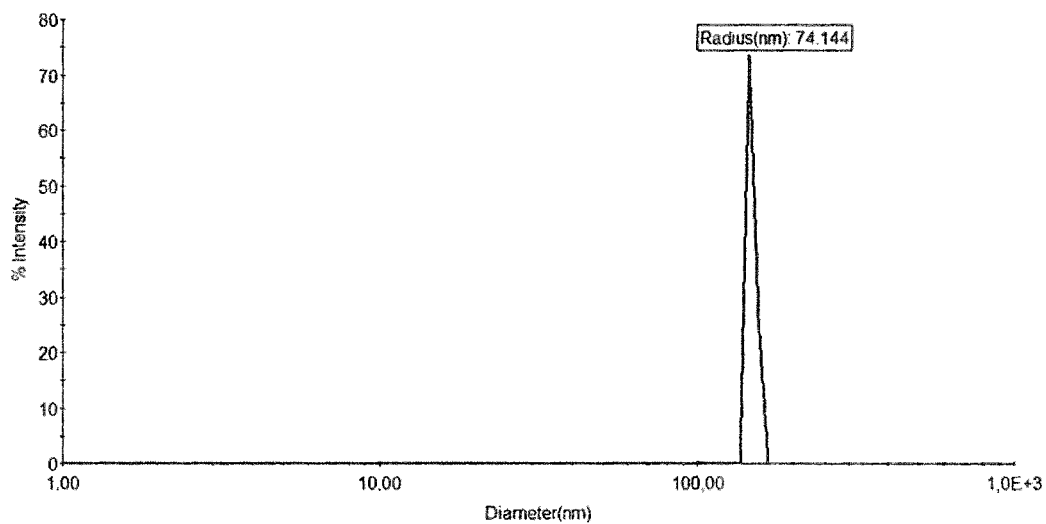
Figure 5:
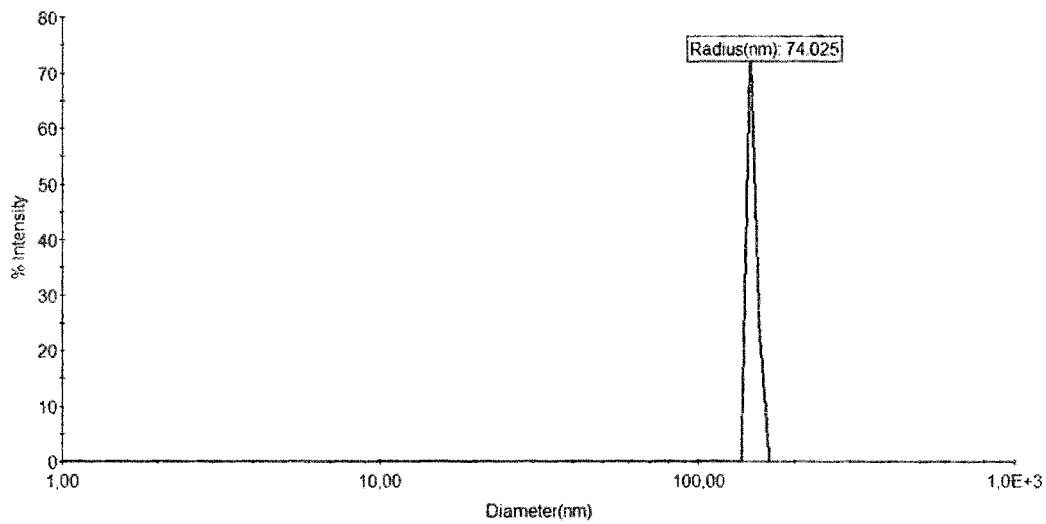
Figure 5:
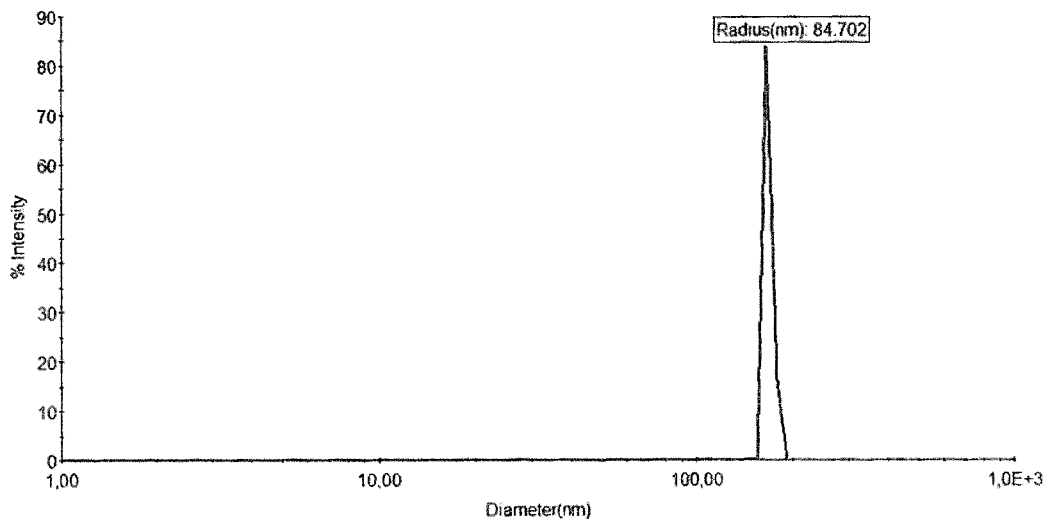
Figure 5:
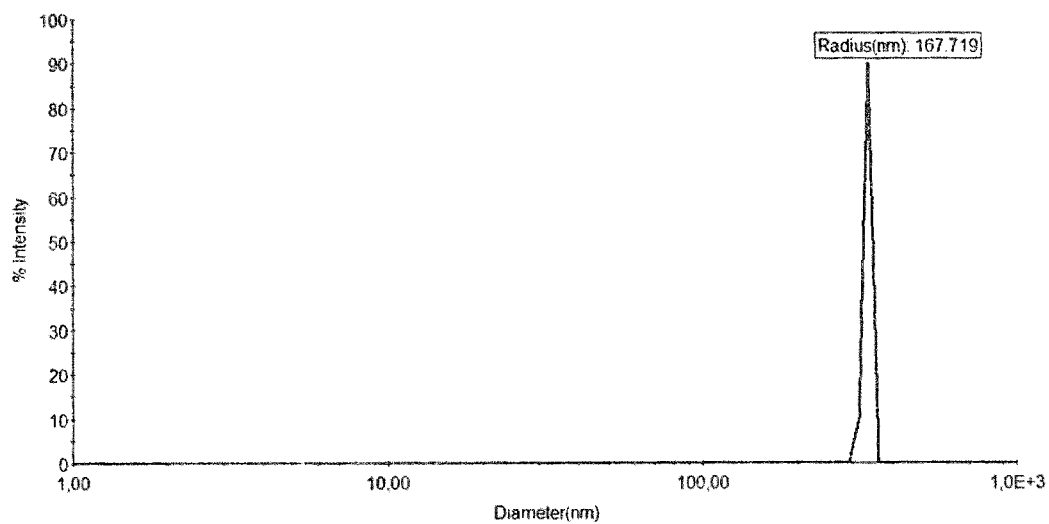

FIG. 5: DLS-Determination of the hydrodynamic radii of the highly concentrated adenoviral particles in the corresponding adenoviral vector preparations after formulation in stabilizing compositions 1 and 2 during either process step 1 or process step 2 as a model for aggregation and polydispersity. Re-buffering of the adenoviral vector particle preparations in composition 1 using dialysis either in process step 1 or 2 resulted in the retention of the hydrodynamic radii of the particles (A) and (C). Re-buffering of the adenoviral particles in composition 2 during preparation in process step 1 led to the complete retention of the hydrodynamic radius of the adenoviral vector (B). In contrast, re-buffering of the adenoviral particles in composition 2 during preparation in process step 2 led to an increase in the hydrodynamic radius of the particles and the associated formation of large aggregates (D).

Figure 6:
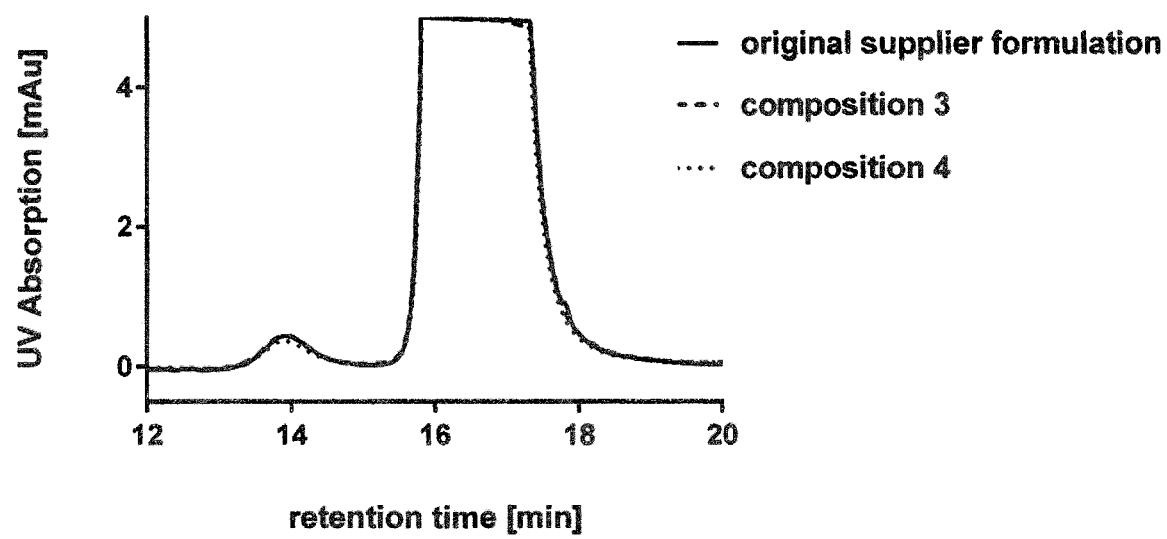

FIG. 6: SE-HPLC profiles of highly concentrated trastuzumab formulations after re-buffering as a stability model for aggregation during processing. The SE-HPLC profiles of untreated samples of liquid preparations of trastuzumab (Herceptin®; trastuzumab—120 mg/ml) directly from the original container were analyzed compared to samples after re-buffering of the liquid original trastuzumab formulation in compositions 3 and 4 showed comparable peak profiles. The main peak at an elution time of approx. 16.5 min corresponds to the structural intact monomer molecules of the antibody, the small peak eluting earlier at an elution time of 14 min corresponds to aggregates in particular to dimers. Traces of fragments eluted at an elution time of 20 min. The resulting SE-HPLC profiles of the antibody in composition 3 and 4 are completely comparable to the corresponding chromatograms of the antibody in the untreated original supplier formulation.

Figure 7:
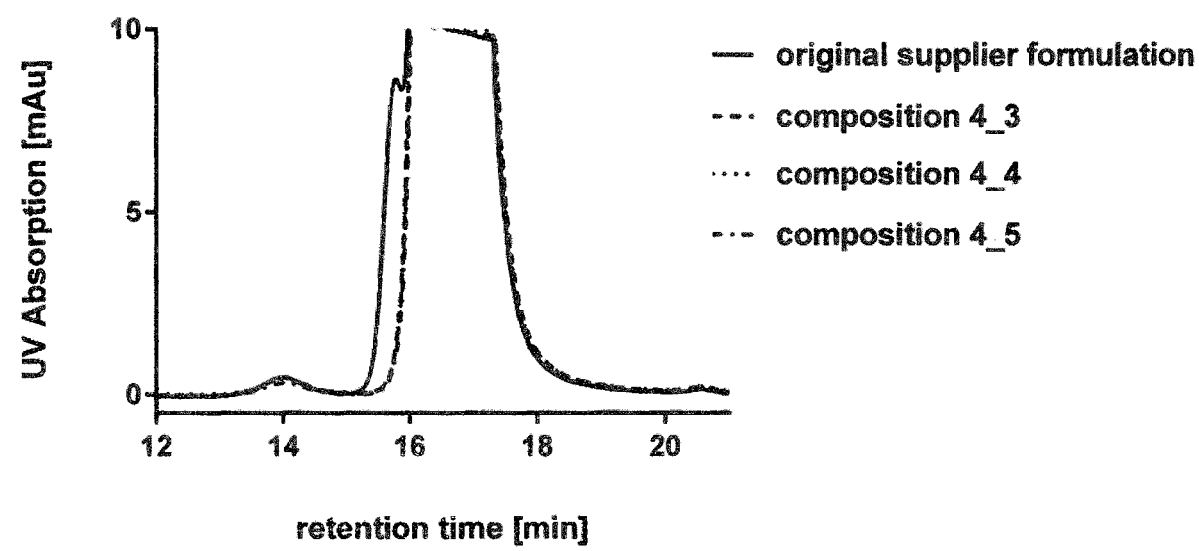

FIG. 7: SE-HPLC profiles of highly concentrated trastuzumab formulations after re-buffering and/or concentration as a stability model for aggregation during processing. Concentration of the liquid, commercially available trastuzumab formulation (Herceptin®; trastuzumab—120 mg/ml) to a concentration of 200 mg/ml resulted in a remarkable increase in the aggregate formation compared to the untreated starting material, as evident from the pronounced shoulder eluting at an elution time of 15 min before the elution of the main peak at 16.5 min. In contrast, re-buffering of the liquid trastuzumab formulation in either of the three compositions according to the invention (composition 4_3, 4_4 or 4_5) and subsequent concentration to 200 mg/ml resulted in the complete retention of the SEC profile of the untreated original liquid trastuzumab formulation (FIG. 8) and a clear baseline separation between the peak at 13 min according to dimers of the antibody and the monomer peak at 16 min elution time. Traces of fragments eluted at an elution time of 20 min.

Figure 8:
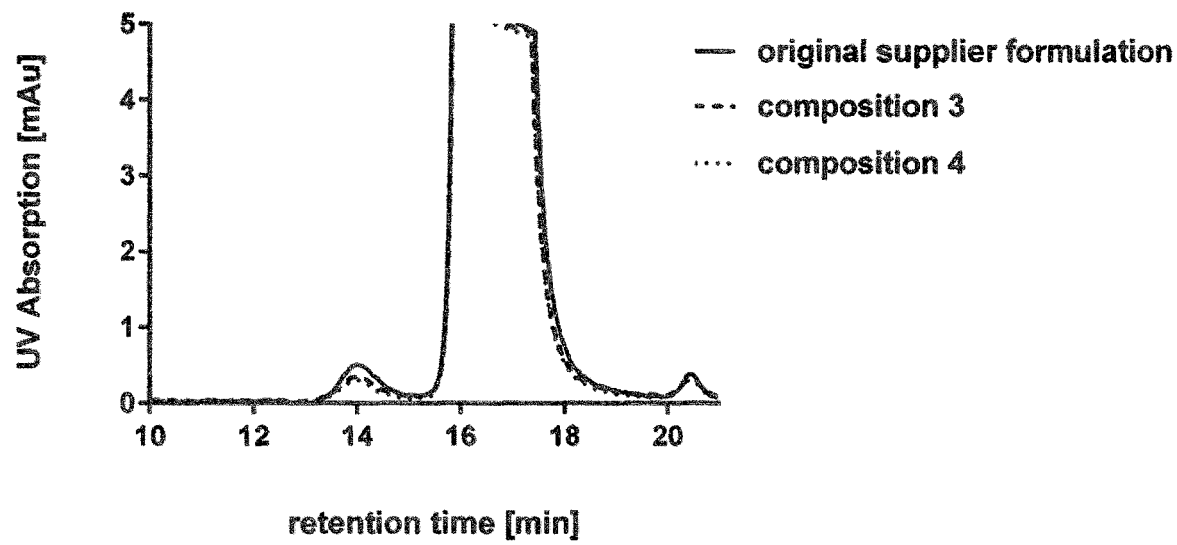
Figure 8:
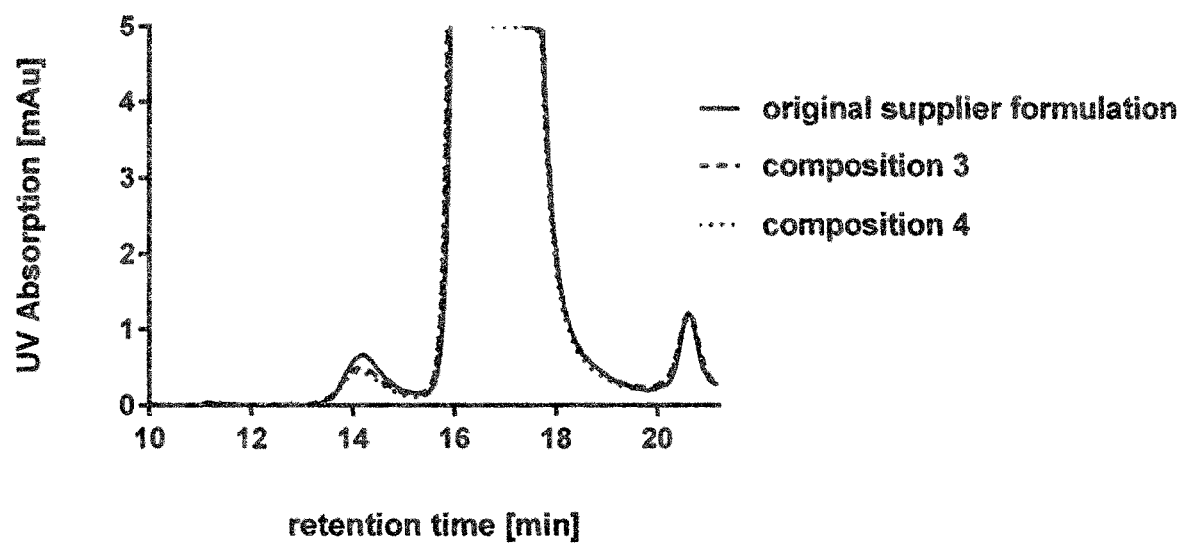
Figure 8:
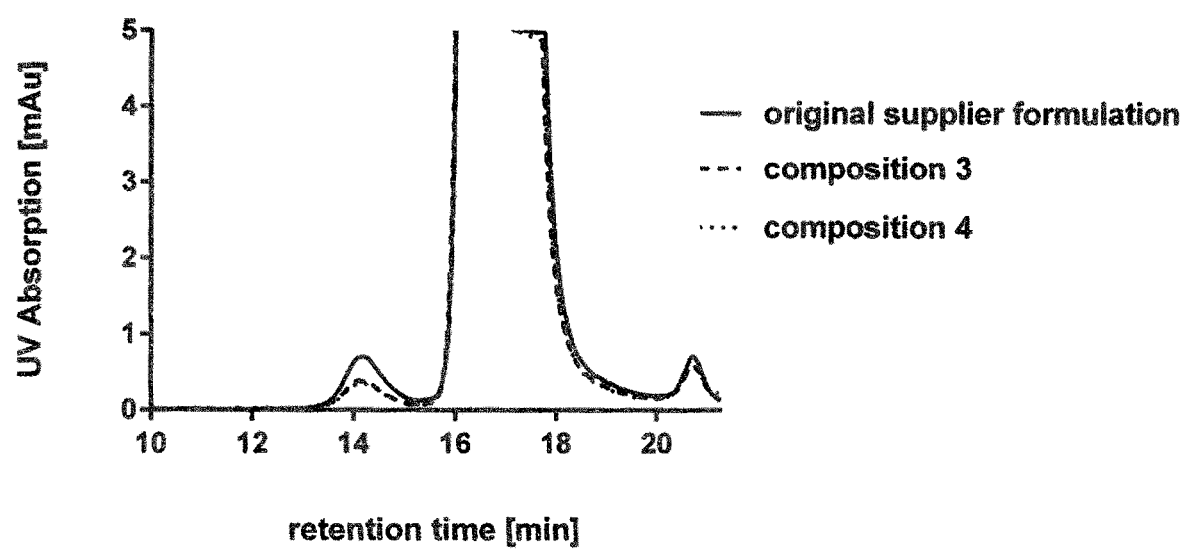

FIG. 8: SE-HPLC profiles of highly concentrated trastuzumab formulations at time point t=0 and after liquid storage at elevated temperatures at indicated analytic time points as a stability model for aggregation during storage and thermal stress. Liquid storage of highly concentrated trastuzumab—120 mg/ml for 1.5 days at 40° C. (A), for 12 days at 40° C. (B), or for 21 days at 30° C. (C) after re-buffering using dialysis in the stabilizing compositions 3 and 4 compared to the parallel liquid storage of the untreated original supplier formulation (Herceptin®; trastuzumab—120 mg/ml). Storage in the compositions according to the invention reduced the aggregation propensity of the antibody (elution of aggregates at 14 min) and, in the case of composition 4, a slightly reduction of the fragmentation (elution of fragments at 21 min) was additionally observed.

Figure 9:
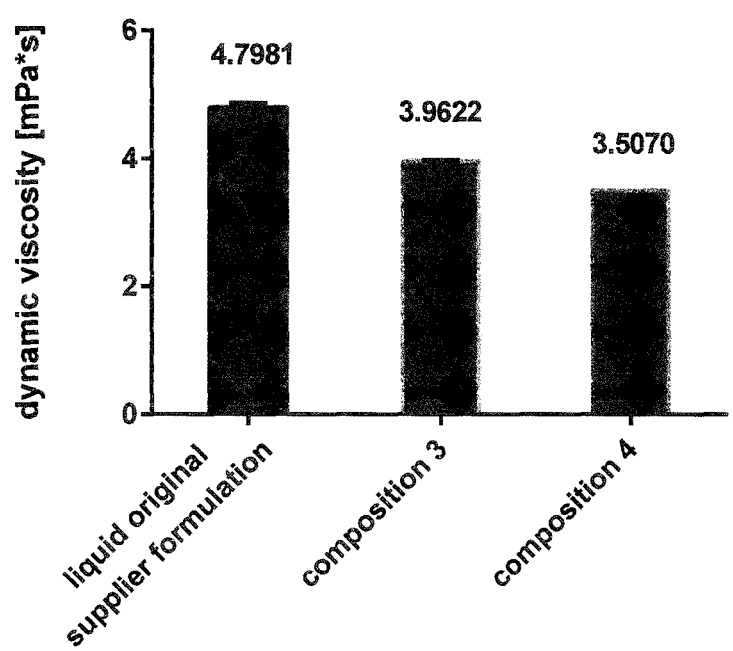

FIG. 9: Dynamic viscosities of highly concentrated trastuzumab formulations after re-buffering in composition 3 and 4 using dialysis compared to the untreated liquid original trastuzumab (Herceptin®; 120 mg/ml) formulation as a model for evaluating viscosity during processing. Re-buffering of the liquid original trastuzumab formulation (Herceptin®; trastuzumab—120 mg/ml) in compositions 3 and 4 (trastuzumab—120 mg/ml) resulted in remarkably reduced viscosities compared to the measured viscosity of the highly concentrated trastuzumab in the untreated, original liquid supplier formulation particularly in the composition 4, also in composition 3 but to a minor extent.

Figure 10:
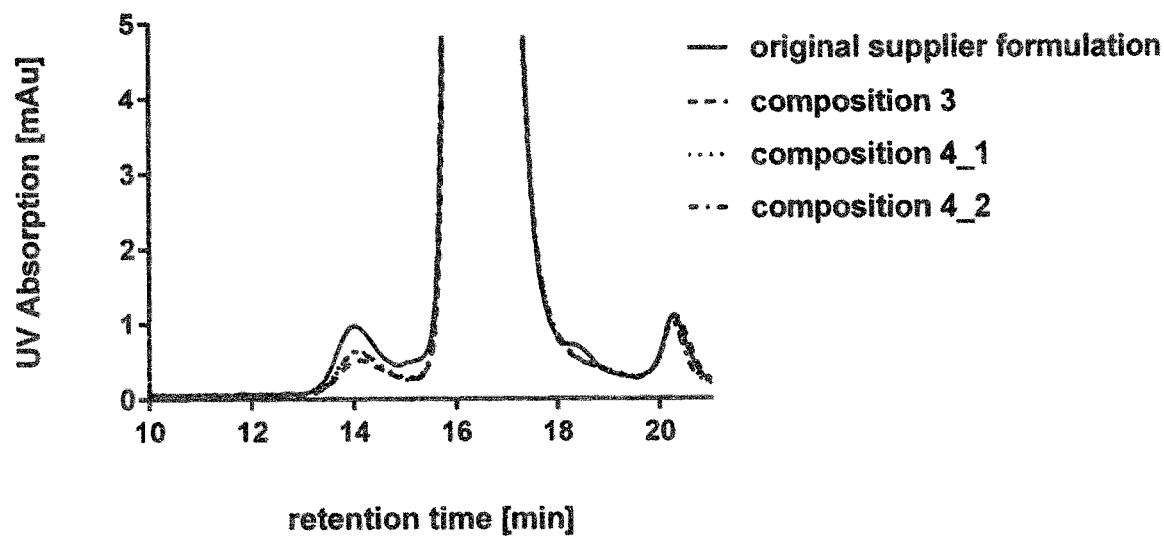
Figure 10:
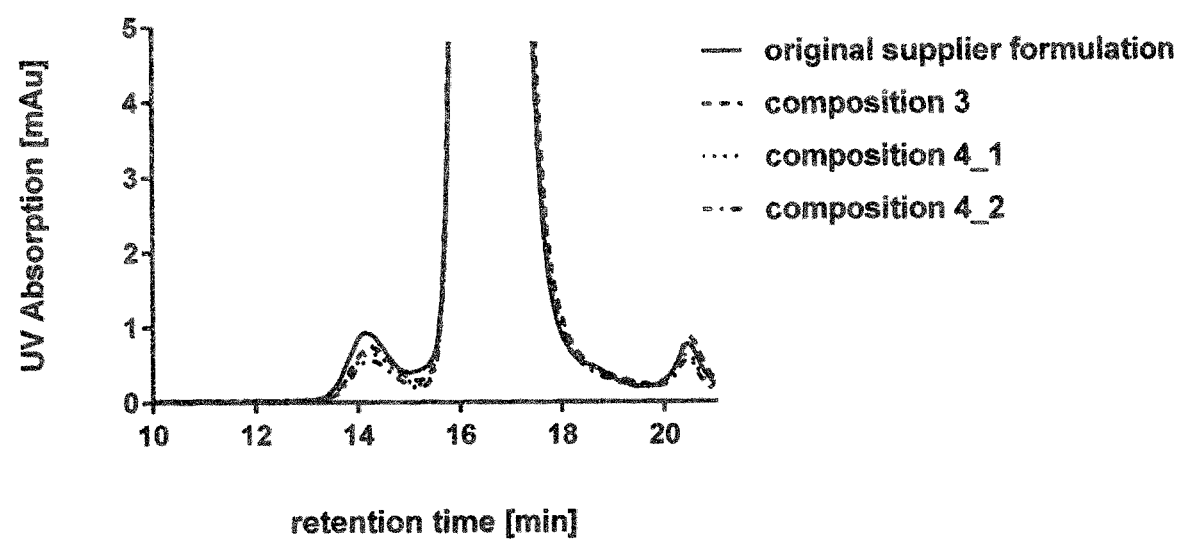

FIG. 10: SE-HPLC profiles of highly concentrated trastuzumab formulations after liquid storage as a stability model for aggregation during processing and thermal stress. Freeze-dried preparations of trastuzumab (Herceptin®) were reconstituted, re-buffered via dialysis In the composition of the original liquid supplier formulation and in compositions 3, 4_1 and 4_2, respectively and subsequently concentrated to trastuzumab—135 mg/ml in the original liquid supplier formulations, to trastuzumab—145 mg/ml in composition 3, to trastuzumab—150 mg/ml in composition 4_1 and to trastuzumab—151 mg/ml in composition 4_2. (A) SE-HPLC profiles of the trastuzumab formulations after liquid storage for 8 days at 40° C. and (B) after liquid storage for one month at 30° C. Liquid storage of trastuzumab for the indicated time periods at 30° C. and 40° C. in the original liquid supplier formulation resulted in the increased formation of aggregates eluting at 14 min with the formation of a shoulder between the aggregate peak and the monomer peak at 16 min and the formation of fragments with the shoulder between the monomer peak and the slightly increased fragment peak eluting at 20 min. In contrast, the respective storage of the antibody for 8 days at 40° C. and one month at 30° C. in compositions 3, 4_1 and 4_2 resulted in decreased aggregation with a clear baseline separation between the aggregate peak and the monomer peak and a reduced fragmentation.

Figure 11:
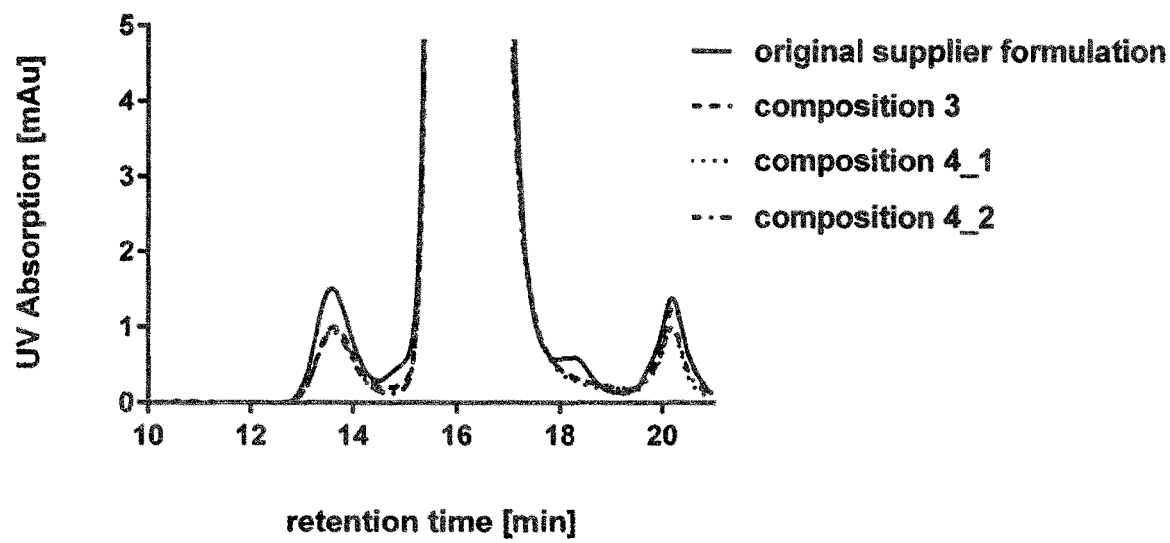
Figure 11:
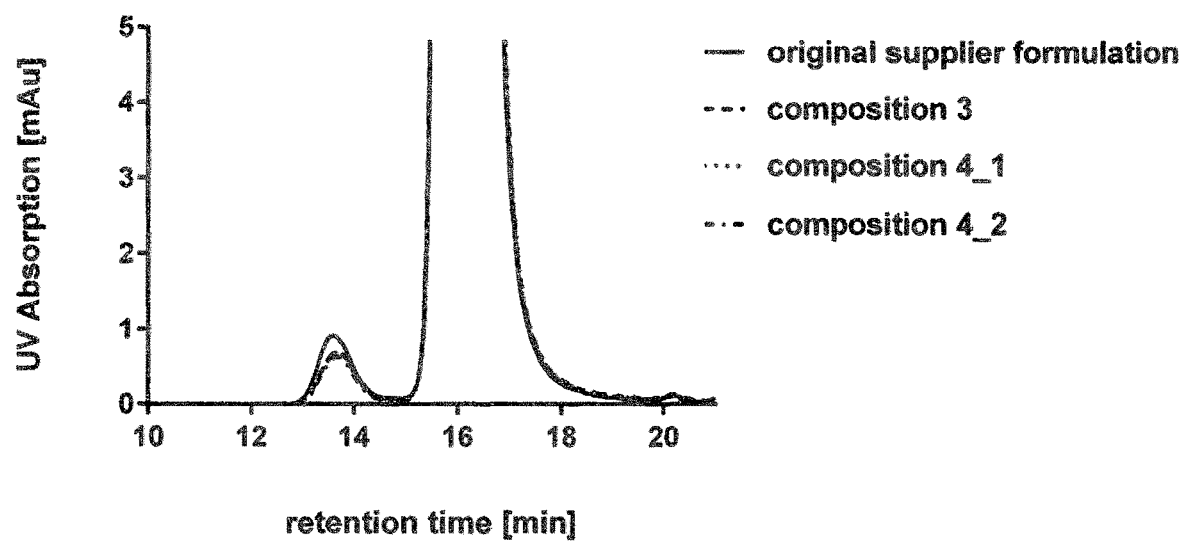

FIG. 11: SE-HPLC profiles of highly concentrated trastuzumab formulations after liquid storage as a stability model for aggregation during processing and storage. Freeze-dried preparations of trastuzumab (Herceptin®) were reconstituted, re-buffered via dialysis In the composition of the original liquid supplier formulation and in compositions 3, 4_1 and 4_2, respectively and subsequently concentrated to trastuzumab—135 mg/ml in the original liquid supplier formulations, to trastuzumab—145 mg/ml in composition 3, to trastuzumab—150 mg/ml in composition 4_1 and to trastuzumab—151 mg/ml in composition 4_2. (A) SE-HPLC profiles of the trastuzumab formulations after liquid storage for six months at 25° C. and (B) after liquid storage for six months at 2-8° C. Liquid storage of the antibody In the original liquid supplier formulation for the indicated time periods at 2-8° C. and 25° C. led to the increased formation of aggregates eluting at 14 min as dimers and as a shoulder between the dimer peak and the monomer peak at 16 min and to the increased formation of fragments eluting as a shoulder between the monomer peak at 17 min and 20 min particularly in the case of 25° C. compared to the liquid storage of the antibody in composition 3, 4_1 and 4:_2. The SE-HPLC profiles of the antibody formulated in compositions 3, 4_1 and 4_2 showed a clear baseline separation between the aggregated peaks and the monomer peaks. In the case of the liquid storage for six months at 2-8° C. the fragmentation was only a minor event in all formulations.

Figure 12:
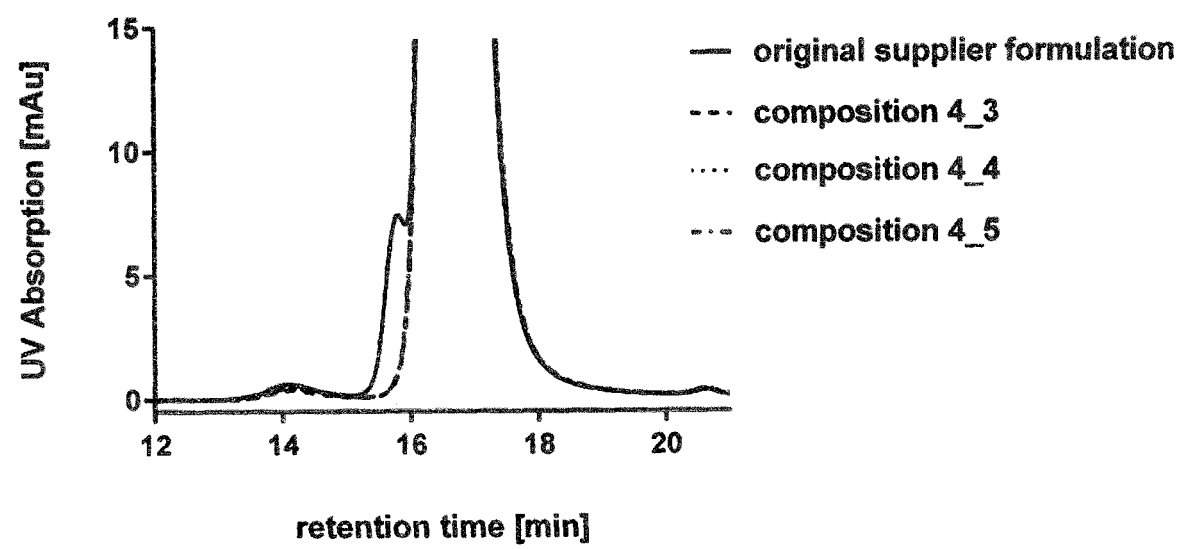
Figure 12:
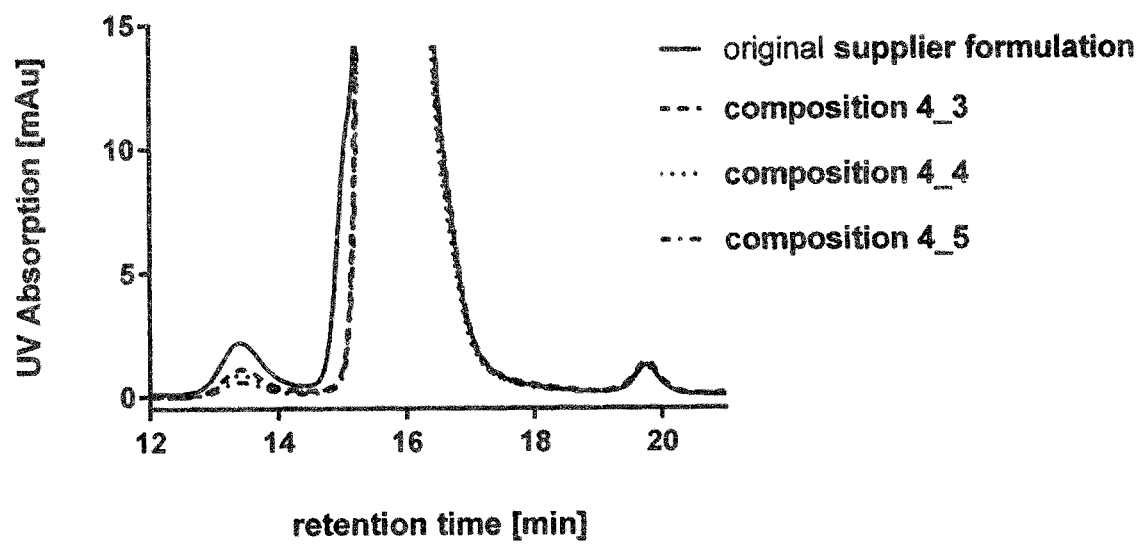

FIG. 12: SE-HPLC profiles of highly concentrated trastuzumab formulations after liquid storage at 40° C. as a stability model for aggregation during processing and storage. Concentration of the liquid, commercially available liquid trastuzumab formulation (Herceptin®; trastuzumab—120 mg/ml) to a concentration of 200 mg/ml and re-buffering of the liquid trastuzumab formulation (Herceptin®; trastuzumab—120 mg/ml) in either of the three compositions according to the invention (composition 4_3, 4_4 or 4_5) and subsequent concentration to 200 mg/ml. (A) SE-HPLC profiles after liquid storage for 3 days at 40° C. and (B) after liquid storage for 14 days at 40° C. The fragmentation was only a minor event during storage of the antibody in such high concentrations. In the compositions according to the invention the propensity for aggregation was strongly reduced compared to the original supplier formulation and a clear baseline separation between the aggregate peak eluting at 14 min and the monomer peak eluting at 16 min was further observed.

Figure 13:
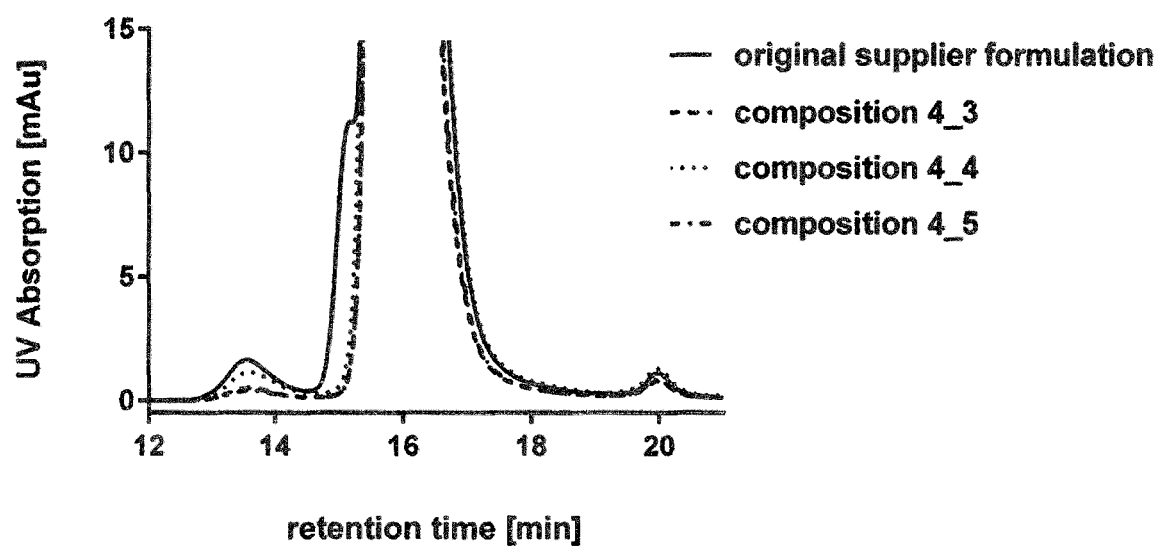
Figure 13:
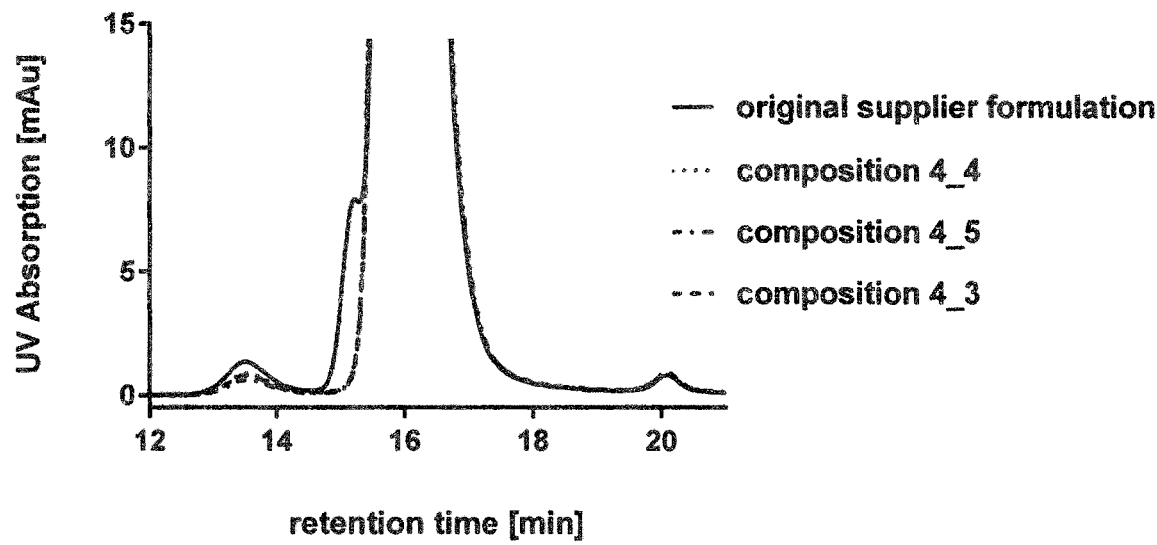

FIG. 13: SE-HPLC profiles of highly concentrated trastuzumab formulations after liquid storage at elevated temperatures as a stability model for aggregation during processing and storage. Concentration of the liquid, commercially available liquid trastuzumab formulation (Herceptin®; trastuzumab—120 mg/ml) to a concentration of 200 mg/ml and re-buffering of the liquid trastuzumab formulation (Herceptin®; trastuzumab—120 mg/ml) in either of the three compositions according to the invention (composition 4_3, 4_4 or 4_5) and subsequent concentration to 200 mg/ml. (A) SE-HPLC profiles after liquid storage for 42 days at 30° C. and (B) after liquid storage for 3 months at 25° C. The fragmentation was only a minor event during storage of the antibody in such high concentrations. In the compositions according to the invention the propensity for aggregation was strongly reduced compared to the original supplier formulation and a clear baseline separation between the aggregate peak eluting at 14 min and the monomer peak eluting at 16 min was further observed.

Figure 14:
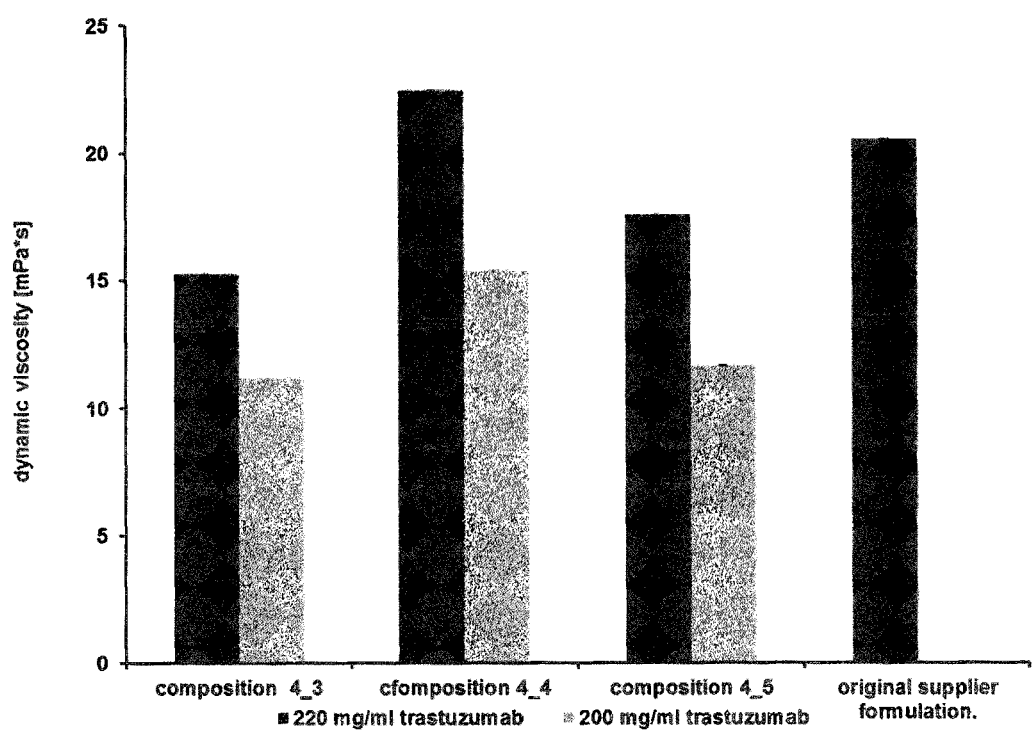

FIG. 14: Dynamic viscosities of the highly concentrated trastuzumab formulations as a model for evaluation of viscosity during processing. Concentration of the liquid original supplier trastuzumab formulation (Herceptin®; trastuzumab—120 mg/ml) to 220 mg/ml, re-buffering of the liquid original supplier trastuzumab formulation (Herceptin®; trastuzumab—120 mg/ml) via dialysis and subsequent concentration to 220 and 200 mg/ml in the compositions 4_3, 4_4 and 4_5. The dynamic viscosities of the highly concentrated trastuzumab formulations were measured in two different concentrations, 200 mg/ml (white bars) and 220 mg/ml (gray bars); for the original supplier formulation only the viscosity of the antibody formulation with a concentration of 220 mg/ml was measured. The dynamic viscosities of the antibody formulations corresponding to compositions 4_3 and 4_4 at an antibody concentration of 220 mg/ml were remarkably reduced compared to the dynamic viscosities in the original supplier formulation at the same concentration. In composition 4_4 the measured dynamic viscosity is slightly increased. A similar trend was shown in the evaluated dynamic viscosities of the samples with an antibody concentration of 200 mg/ml.

Figure 15:
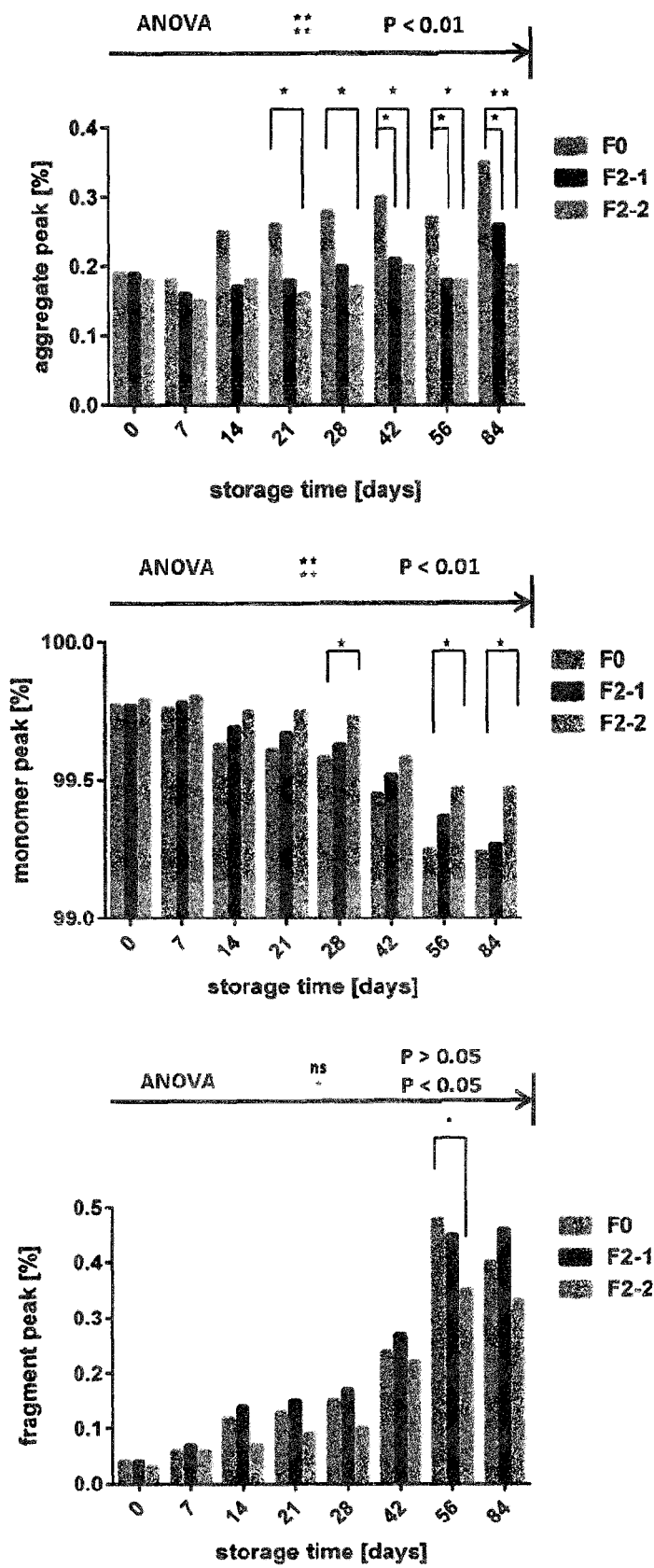
Figure 15:
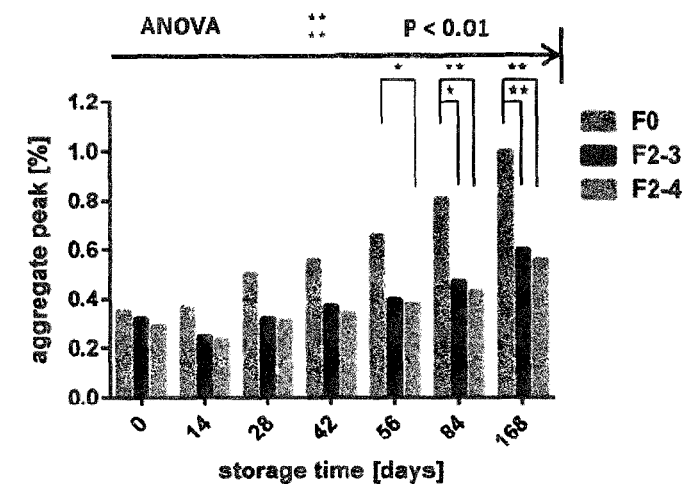
Figure 15:
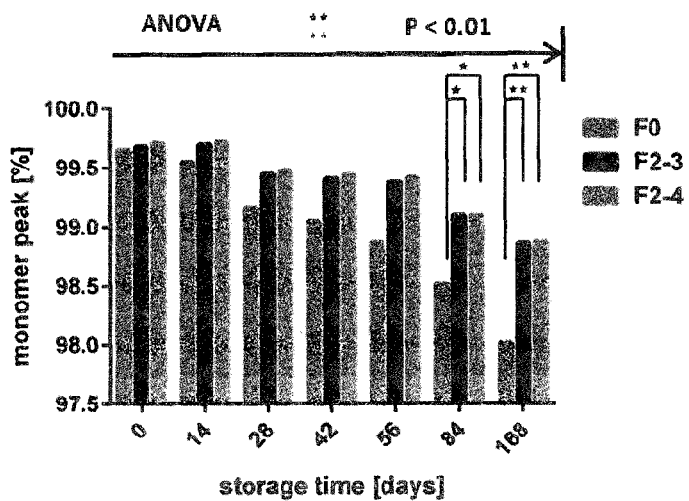
Figure 15:
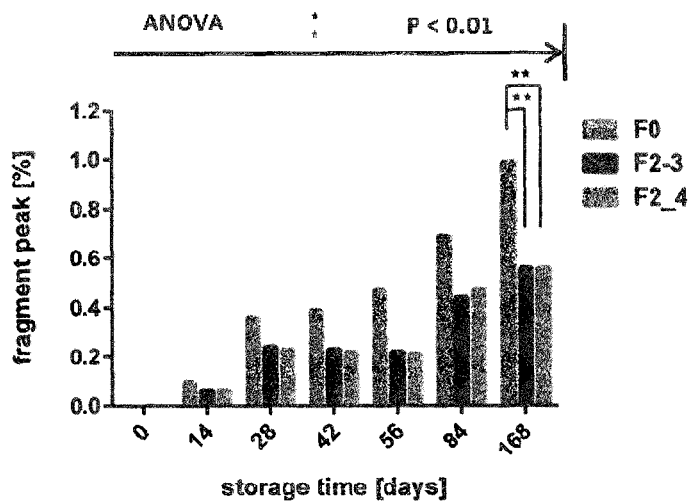
Figure 15:
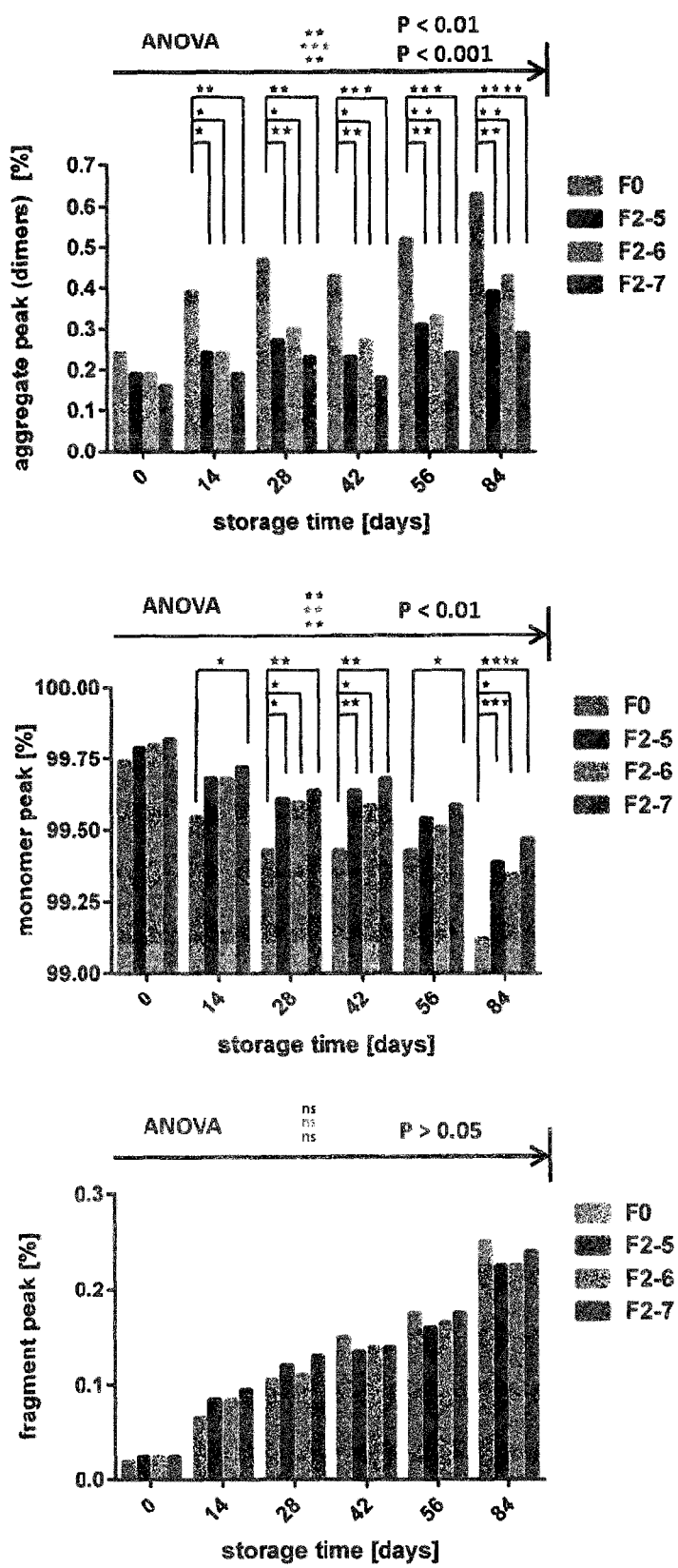

FIG. 15. SE-HPLC analysis of highly concentrated trastuzumab during liquid storage. Relative AUC of aggregate peaks (top), monomer peaks (middle) and fragment peaks (bottom) obtained by SE-HPLC are depicted. (A) Relative AUC of SE-HPLC peaks of 120 mg/mL trastuzumab during liquid storage for 3 months at 30° C. in F2-1 and F2-2 compared to the original formulation. (B) Relative AUC of SE-HPLC peaks of 150 mg/mL trastuzumab during liquid storage for 6 months at 25° C. in F2-3 and F2-4 compared to the original formulation. (C) Relative AUC of SE-HPLC peaks of 200 mg/mL trastuzumab during liquid storage for 3 months at 25° C. in F2-5, F2-6 and F2-7 compared to the original liquid formulation. Original: (120 mg/mL) F0 formulation (F0).

Figure 16:
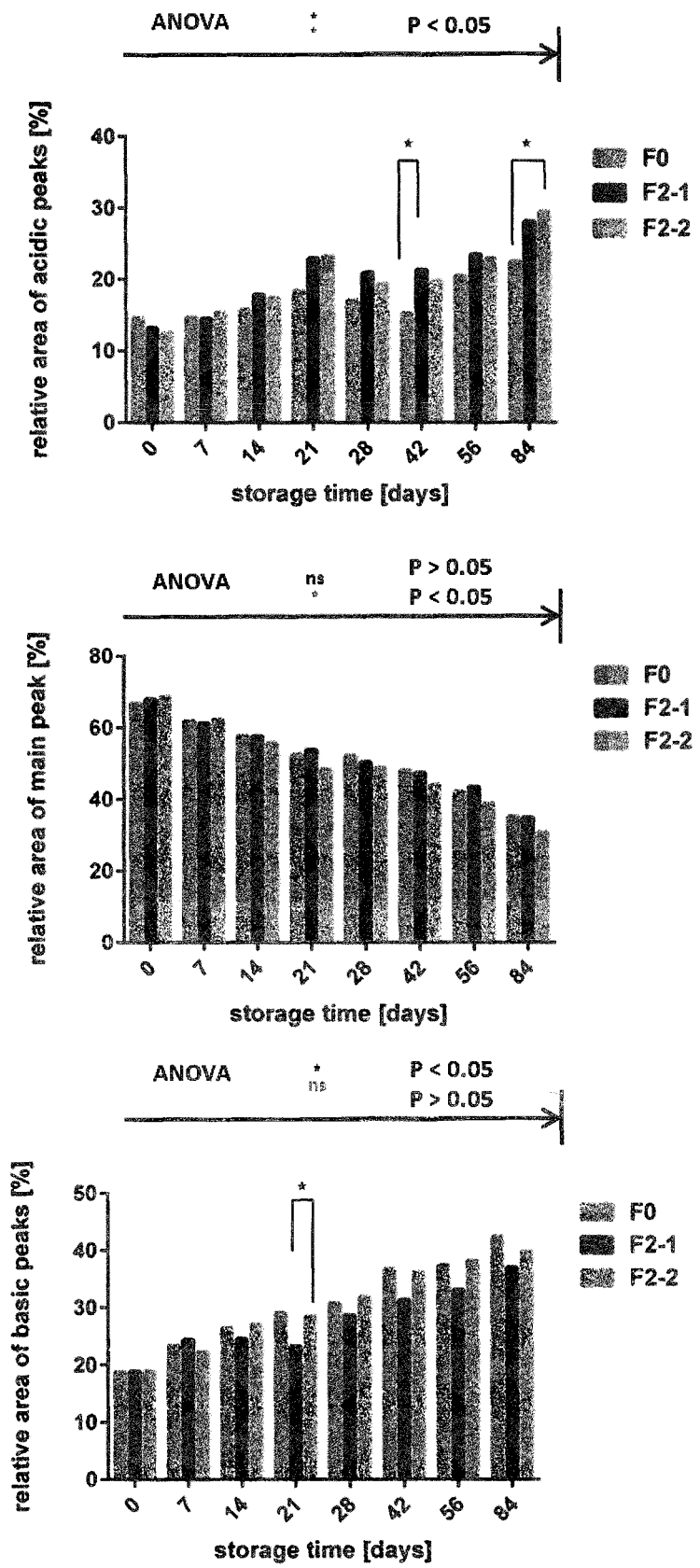
Figure 16:
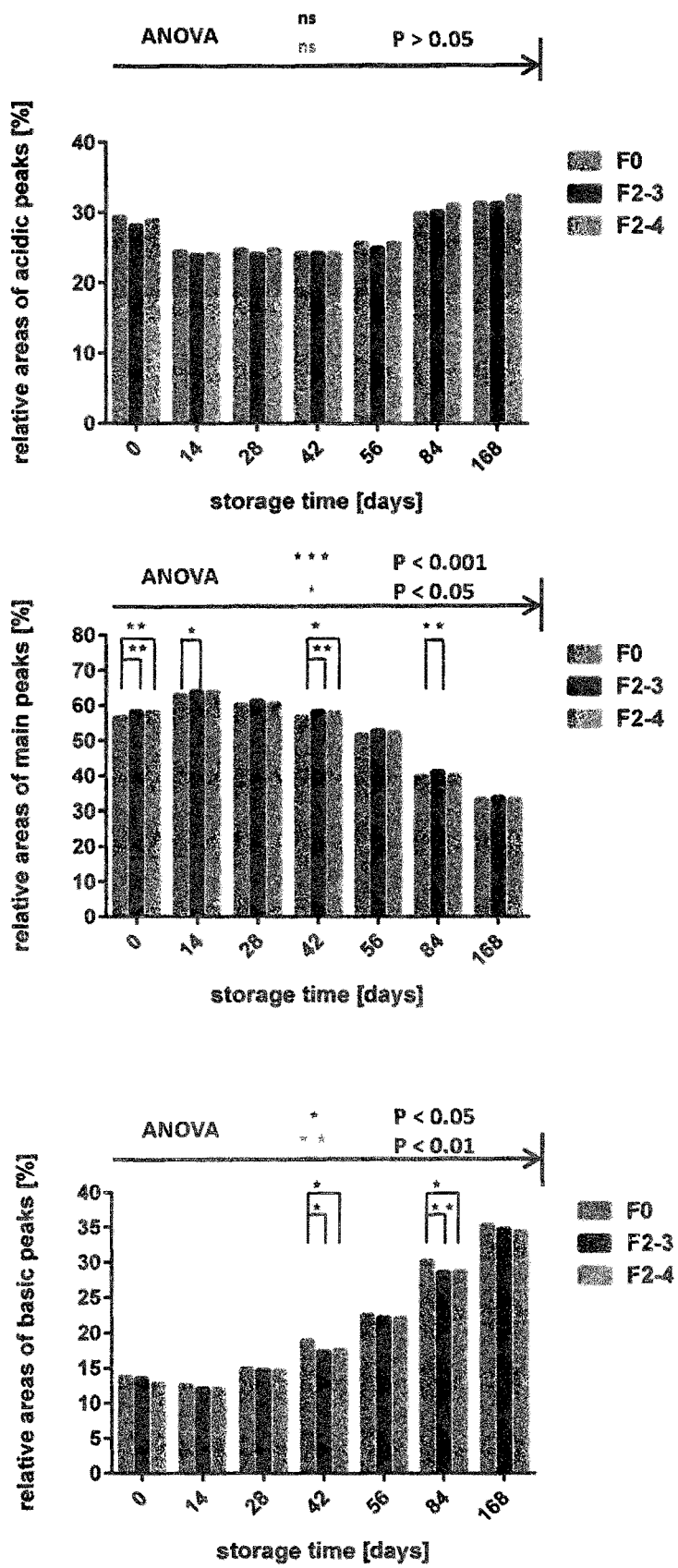
Figure 16:
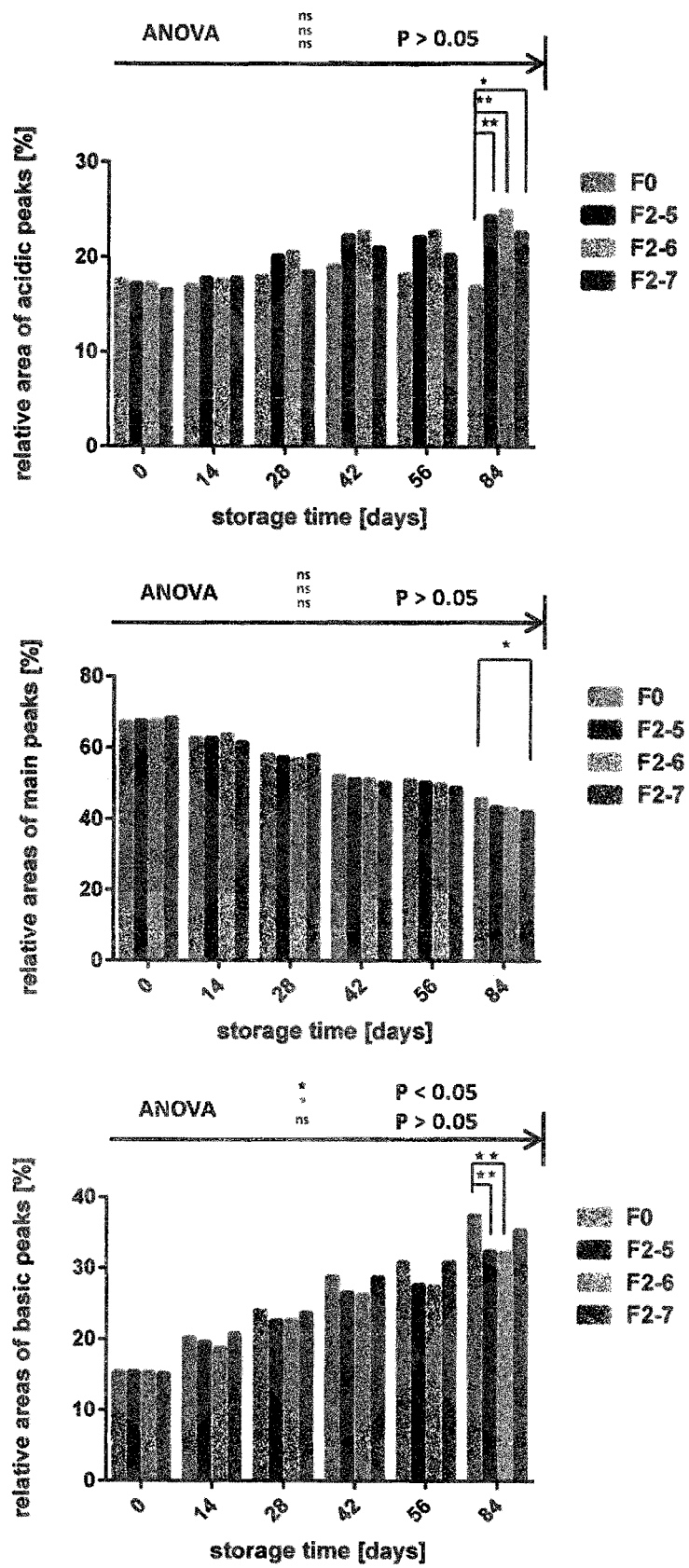

FIG. 16. Cationic exchange chromatography (CEX-HPLC) analysis of trastuzumab during liquid storage. (A) Relative AUC of CEX-HPLC peaks of 120 mg/mL trastuzumab during liquid storage for 3 months at 30° C. in F2-1 and F2-2 compared to the original formulation. (B) Relative AUC of CEX-HPLC peaks of 150 mg/mL trastuzumab during liquid storage for 6 months at 25° C. in F2-3 and F2-4 compared to the original formulation. (C) Relative AUC of CEX-HPLC peaks of 200 mg/mL trastuzumab during liquid storage for 3 months at 25° C. in F2-5, F2-6 and F2-7 compared to the original liquid formulation. Original: (120 mg/mL) F0 formulation (F0). (A-C) acidic species (top), main peak species (middle) and basic species (bottom).

Figure 17:
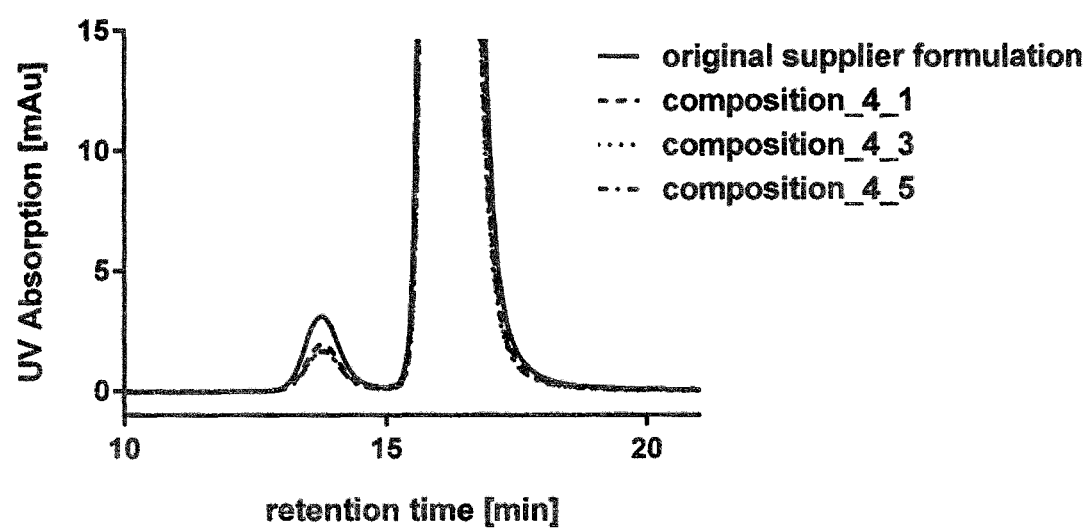

FIG. 17: SE-HPLC profiles of highly concentrated trastuzumab formulations after re-buffering and subsequent concentration to antibody concentrations up to 200 mg/ml as a model for drug substance to drug product processing. Freeze-dried preparations of trastuzumab (Herceptin®) were reconstituted, re-buffered via dialysis In the composition of the original liquid supplier formulation and in compositions 4_1, 4_3 and 4_5, respectively and subsequently concentrated to trastuzumab concentrations of up to 200 mg/ml. Concentration of the antibody in the original liquid supplier formulation resulted in an increased formation of aggregates eluting at a retention time of 14 min compared to the concentration of the antibody formulated in compositions 4_1, 4_3 and 4_5.

Figure 18:
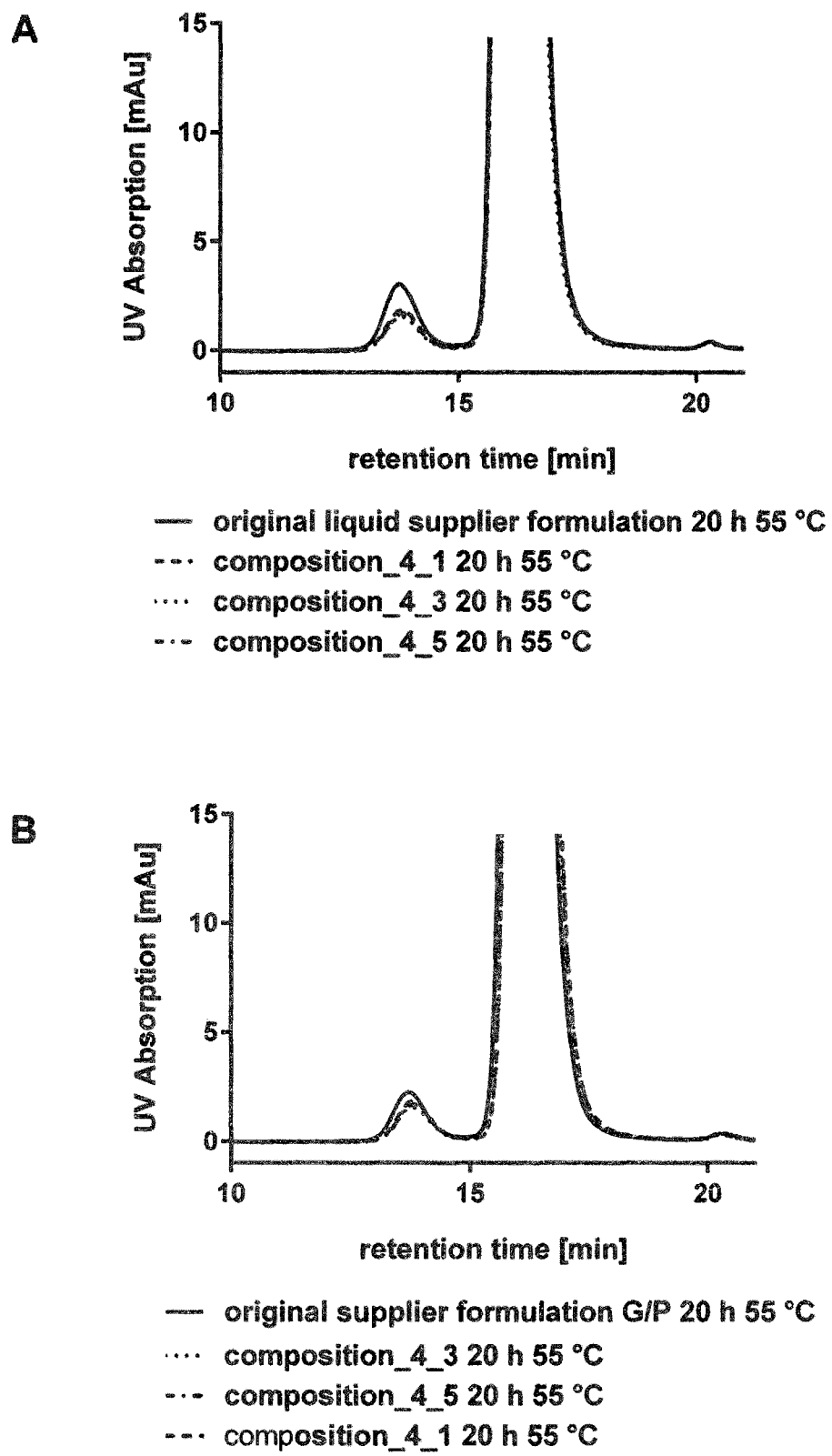
Figure 18:
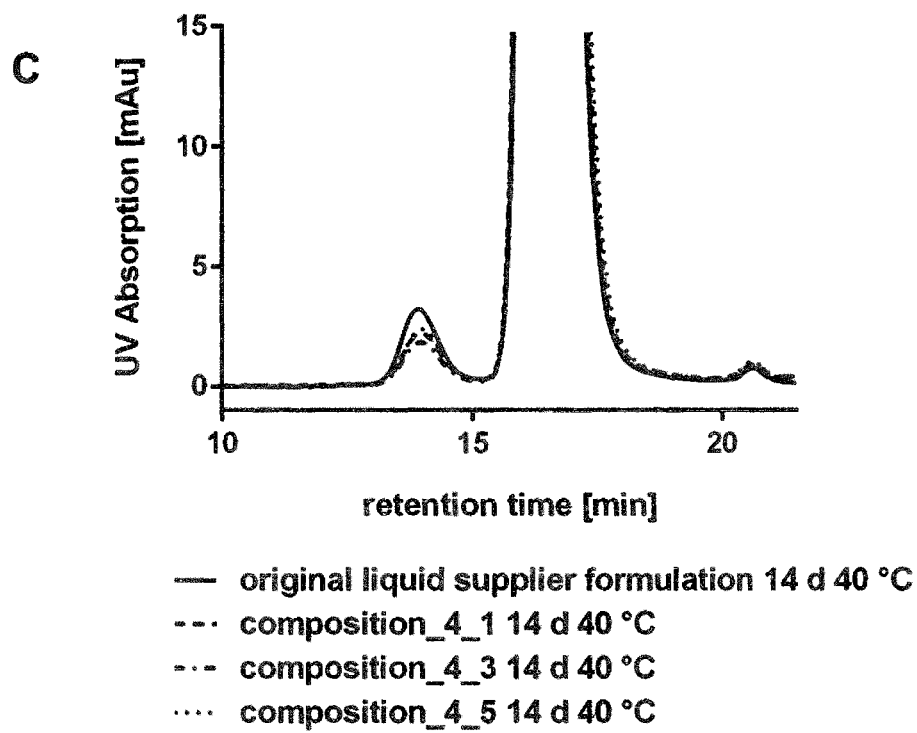
Figure 18:
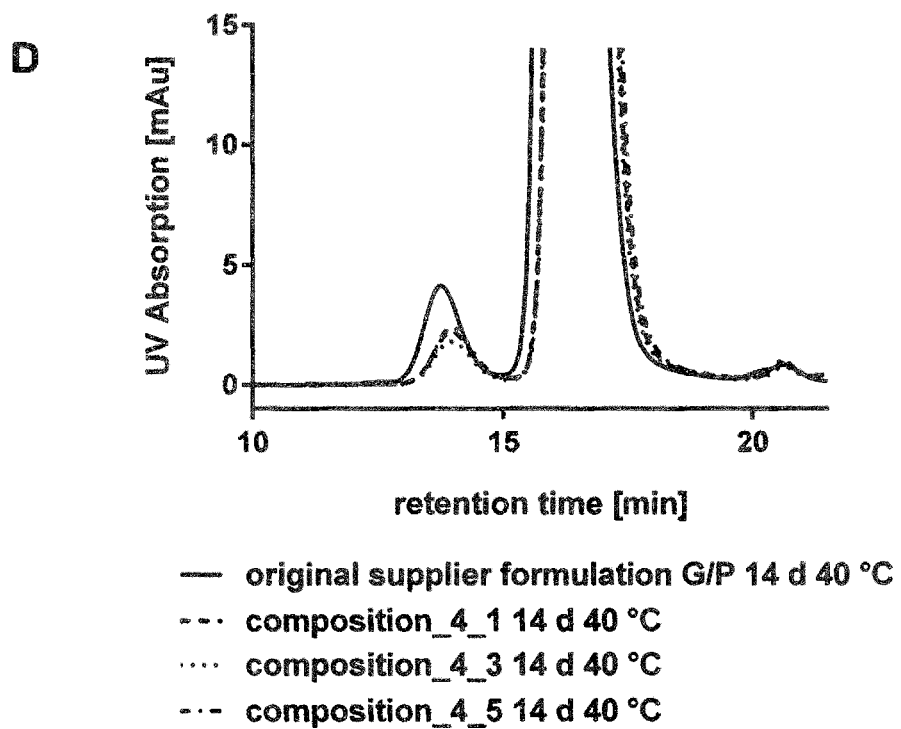
Figure 18:
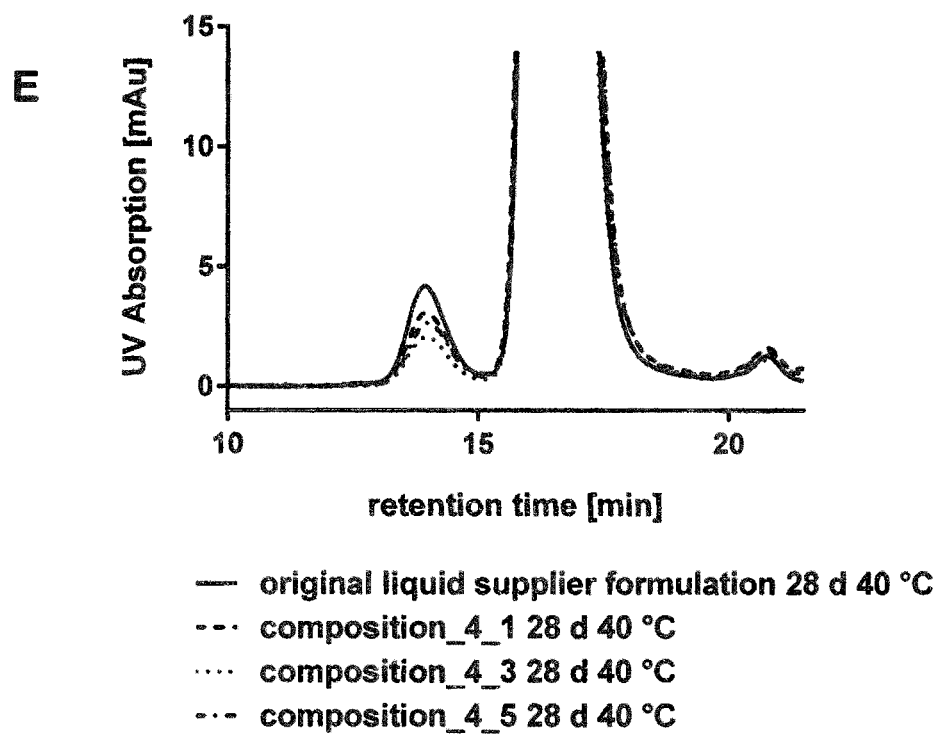
Figure 18:
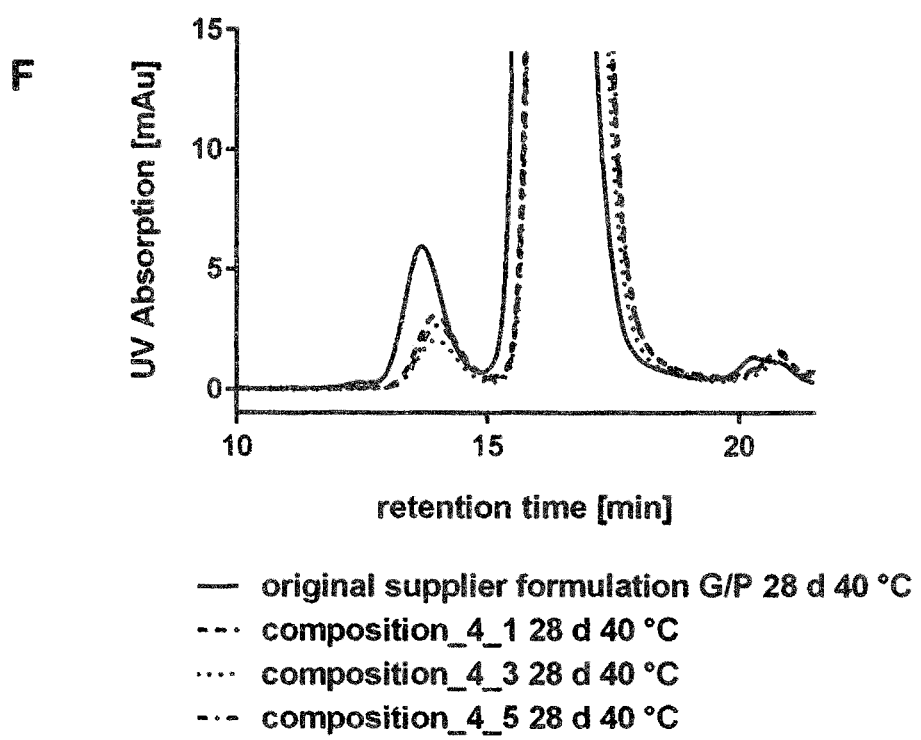

FIG. 18: SE-HPLC profiles of highly concentrated trastuzumab formulations after liquid storage as a model for drug product stability. Freeze-dried preparations of trastuzumab (Herceptin®) were reconstituted, re-buffered via dialysis In the composition of the original liquid supplier formulation and in the original supplier formulation of the freeze-dried product wherein this formulation additionally contained the amino acids glycine and proline in the concentrations described in U.S. Pat. No. 9,364,542 B2 (Example 16). For comparison the reconstituted trastuzumab (Herceptin®) was additionally re-buffered via dialysis in the compositions 4_1, 4_3 and 4_5 respectively. All formulations were subsequently concentrated to trastuzumab concentrations of 200 mg/ml (A) and (B) SE-HPLC profiles of trastuzumab after liquid storage for 24 h at 55° C. formulated in compositions 4_1, 4_3 and 4_5 compared to the original liquid supplier formulation (A) and compared to the original supplier formulations with glycine and proline (B), respectively. (C) and (D) SE-HPLC profiles of trastuzumab after liquid storage for 14 days at 40° C. formulated in compositions 4_1, 4_3 and 4_5 compared to the original liquid supplier formulation (C) and compared to the original supplier formulations with glycine and proline (D), respectively. (E) and (F) SE-HPLC profiles of trastuzumab after liquid storage for 28 days at 40° C. formulated in compositions 4_1, 4_3 and 4_5 compared to the original liquid supplier formulation (E) and compared to the original supplier formulations with glycine and proline (F), respectively. The depicted SE-HPLC chromatograms after liquid storage for different times at elevated temperatures showed that compositions 4_1, 4_3 and 4_4 effectively prevented the formation of aggregates compared in particular to the original formulations of the freeze-dried product with the additives glycine and proline according to the said US patent.

Figure 19:
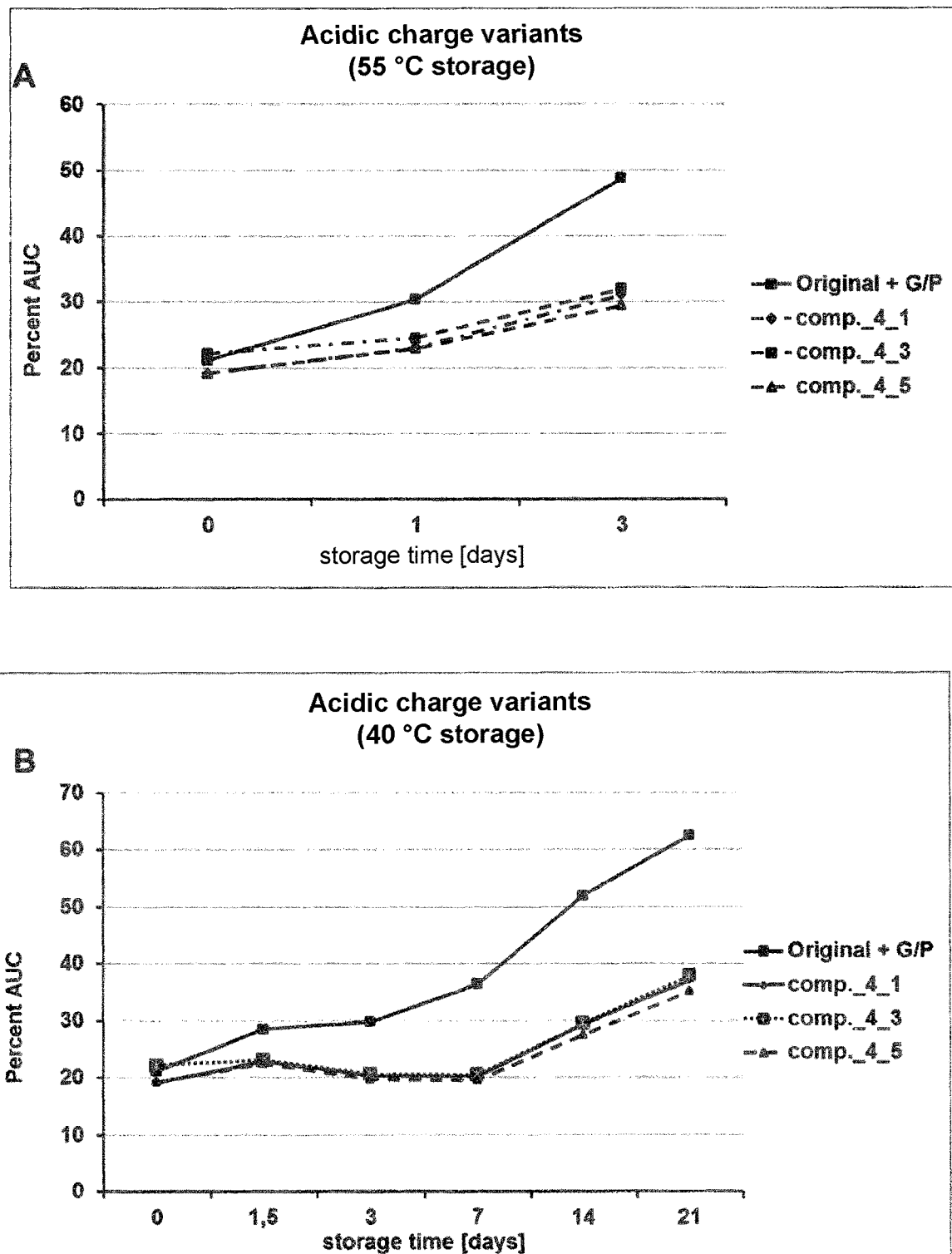
Figure 19:
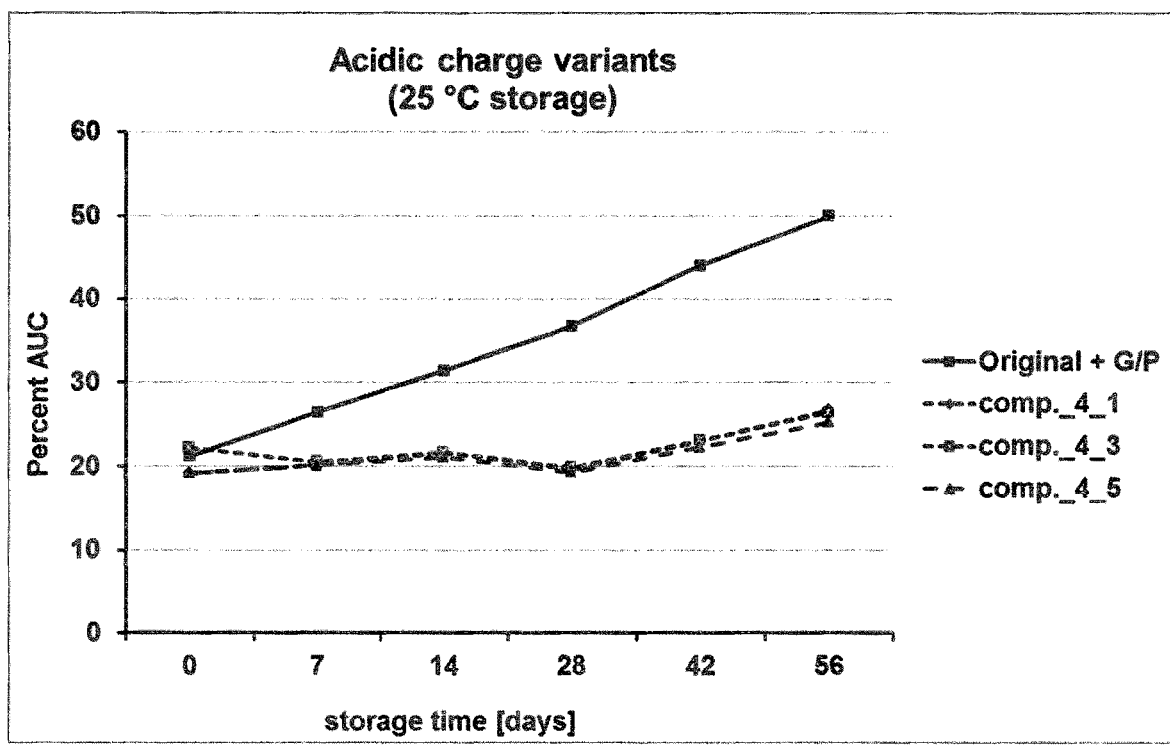

FIG. 19: CEX-HPLC analysis of highly concentrated trastuzumab formulations after liquid as a model for drug product stability. Freeze-dried preparations of trastuzumab (Herceptin®) were reconstituted, re-buffered via dialysis In the composition of the original liquid supplier formulation and in the original supplier formulation of the freeze-dried product wherein this formulation additionally contained the amino acids glycine and proline in the concentrations described in U.S. Pat. No. 9,364,542 B2 (Example 16). For comparison the reconstituted trastuzumab (Herceptin®) was additionally re-buffered via dialysis in the compositions 4_1, 4_3 and 4_5 respectively. All formulations were subsequently concentrated to trastuzumab concentrations of 200 mg/ml. Course of increasing relative percent areas of the peaks corresponding to the formation of acidic charge variants (A) at indicated analytic time points during liquid storage at 55° C., (B) at indicated analytic time points during liquid storage at 40° C. and (C) at indicated analytic time points during liquid storage at 25° C. The depicted course of the formation of acidic charge variants of the antibody molecule further underline the stabilizing efficacy of compositions 4_1, 4_3 and 4_5 against chemical changes in the antibody molecule. In particular, stabilization against the formation of acidic charge variants suggests a higher stabilizing efficacy of the compositions 4_1, 4_3 and 4_5 against deamidation known as the main chemical change in the trastuzumab molecule and the resulting main contribution to the amount of the formation of acidic charge variants during liquid storage at elevated temperatures. In contrast, the original supplier formulation of the freeze-dried product with the amino acids glycine and proline as additives according to the US patent example showed a remarkable higher tendency for the formation of acidic charge variants during the course of liquid storage at elevated temperatures at high antibody concentrations.

The examples illustrate the invention.

EXAMPLE 1

The in vitro study of the functional and structural integrity of freeze dried and subsequently stored highly concentrated adenoviral vectors, as a predictive model for liquid storage-associated loss of molecular integrity, showed that compositions based on amino acids and sugar, stabilize viral vectors.

1.1 Materials and Methods

Composition 1 and 2 contained the 7 amino acids alanine, arginine, glycine, glutamic acid, lysine, histidine and tryptophan in a concentration corresponding to the sum of the amino acids of 40 g/l. But in composition 1, a 5 fold increase of the tryptophan concentration and a 1.667 fold increase of the histidine and glutamic acid concentration under reduction of the concentrations of the other amino acids arginine, glycine, lysine and the retention of the alanine concentration compared to composition 2 resulted in the same concentration according to the sum of amino acids of 40 g/l. Further, an additional surfactant polysorbate 80 in a concentration of 0.05 g/l was added to composition 1 in contrast to composition 2. Both compositions contained trehalose as the corresponding sugar in an amino acid to trehalose ratio of 1:2. The pH value was adjusted in all compositions to 7.

An adenoviral stock solution stored at −80° C. with a concentration of $7.5*10^{10}$ IFU/ml in the original supplier formulation (Firma Sirion; Martinsried/Munich; Germany) was employed.

1.1.1 Sample Preparation and Freeze Drying

The adenoviral vector stock solution was re-buffered by dilution of the stock solution to a concentration of $1*10^8$ IFU/ml with either composition 1 or composition 2. For comparison the stock solution was diluted with either the original supplier formulation or with PBS to the same concentrations.

In order to prepare the samples for freeze drying, the different adenoviral formulations were aliquoted in volumes of 500 µl in 2R freeze drying vials (Schott AG; Mainz; Germany) and subsequently freeze-dried using the following drying parameters:

| Protocol Step | Target T (° C.) | Slope (h) | Hold (h) | Pressure (mbar) |
|---|---|---|---|---|
| Introduction | 20 | 0 | 0 | 1000 |
| Freezing | −50 | 2:00 | 2:00 | 1000 |
| Sublimation | −50 | 0:01 | 0:30 | 0.045 |
|  | −35 | 3:00 | 30:00 | 0.045 |
| Secondary Drying | 20 | 3:00 | 7:00 | 0.009 |

After freeze drying, the samples were visually inspected and one part of the samples was stored for a short time at 2-8° C. until analysis of the initial infective titer at the time point t=0.

The other part of the samples was stored according to the guidelines of the International Council for Harmonization (ICH) for 21 or 42 days at 25° C. under environmental conditions of 60% residual humidity, or for 7 or 28 days at 40° C. under environmental conditions of 75% residual humidity.

1.1.2 Determination of the Infective Titers for Adenoviral Vectors in Cell Culture In order to analyze the infective titer of the adenoviral vector formulations, an antibody based virus titration experiment in HEK 293 cell culture using the detection of the adenoviral Hexon protein after successful amplification of the adenovirus in the infected cells was applied. $2.5*10^5$ HEK 293 (CCS) cells (Firma Sirion; Martinsried/Munich; Germany) were seeded per well of a 24-well micro titer plate in a volume of 500 µl. The adenoviral vector formulations were reconstituted either directly after freeze drying or at the indicated time points upon storage at 25° C. and at 40° C. As a positive control an aliquot of the adenoviral stock solution stored at −80° C. with a concentration of $7.5*10^{10}$ IFU/ml in the original supplier formulation (Firma Sirion; Martinsried/Munich; Germany) was used. Subsequently, serial dilutions of the adenoviral samples were prepared and 50 µl of the resulting dilutions per well were used for infection of the cells. The plates were incubated for 42 hours at 37° C. After infection, cells were fixed with methanol, incubated with the primary anti-Hexon protein antibody (Santa Cruz Biotechnology, Inc.; Dallas; Texas: USA), subsequently incubated with an horse radish peroxidase (HRP)-conjugated secondary anti-mouse antibody (Cell Signaling Technology; Danvers; Massachusetts; USA) specific for the primary antibody and an HRP enzymatic reaction with diaminobenzidine (Carl Roth GmbH and Co. KG; Grafrath; Germany) was carried out, wherein a brown colouring indicates infected cells. The number of infected cells was quantified by counting the brown coloured cells under the microscope, wherein each infected cell is counted as one infectious viral particle.

1.2 Results

The in vitro infectivity assay revealed that a formulation of adenoviral vector preparations in the stabilizing compositions 1 and 2 early in the production process of a freeze dried biopharmaceutical product resulted in infective titers that correspond to those of the positive control depicted as dashed line in FIG. 1. Thus, a complete retention of infective titers was observed after freeze drying. In contrast, when the adenoviral vectors re-buffered in the original supplier formulation were freeze-dried, a remarkable loss of the infective titers was observed and freeze drying in PBS even resulted in a complete loss of the corresponding infective titers (FIG. 1).

These differences were even more striking after storage of the freeze-dried preparations. A complete loss of function of the viral vectors freeze-dried in the original supplier formulation (FIG. 2) was observed, similar to the results obtained in PBS. In contrast, even after storage at 25° C. or even at 40° C., the freeze-dried adenoviral vector compositions that were formulated in the stabilizing compositions 1 and 2 early during the production process retained almost the same viral activity as the positive control, i.e. the adenoviral vector prior to being freeze-dried (depicted as dashed line in the diagram of FIG. 2).

EXAMPLE 2

The in vitro study of the functional and structural integrity of different adenoviral vector preparations after freeze and thaw stress as a predictive model for stress-associated loss of molecular integrity during processing showed that compositions based on amino acids and sugar, stabilize viral vectors even during freeze and thaw cycles 2.1 Materials and Methods 2.1.1 Sample Preparation and Further Processing High titers of adenoviral vector stocks of the adenoviral type 5 vectors containing the coding DNA for the eGFP protein $5*10^8$ HEK293 cells were transduced with adenoviral particles. 48 h after transduction, the cells were harvested and the release of viral particles was performed via Na-Deoxycholat and DNase I treatment. Viral particles were purified by CsCl gradient ultracentrifugation usually followed by buffer exchange in the original supplier formulation on PD10 columns and subsequent determination of the infective titer. The resulting high titer adenoviral stocks were subsequently aliquoted and stored at −80° C.

Sample preparation—process step 1: Adenoviral vector formulations were prepared by re-buffering of the adenoviral vector preparations immediately after CsCl gradient ultracentrifugation. The obtained adenoviral vector band was harvested and dialysed at 2-8° C. in either composition 1 or 2 (as described in 1.1). The resulting formulations were aliquoted and stored at −80° C.

Sample preparation—process step 2: Frozen (−80° C.) adenoviral stock solutions ($7.5*10^{10}$ IFU/ml; Sirion, Martinsried/Munich, Germany) were thawed (room temperature; RT) in the original supplier buffer and subsequently dialysed at 2-8° C. in compositions 1 and 2.

2.1.2 Repeated Freeze and Thaw Cycles with Adenoviral Samples from Process Step 1 and Step 2 Preparations In order to analyze the stability of the adenoviral vector preparations during subsequent stress conditions, 50 µl of the adenoviral vectors, formulated in composition 1 or 2 were subjected to repeated freeze (−80° C.) and thaw (RT) cycles. The in vitro infectivity (described in 1.1.2) was determined at the initial time point t=0 and after 5 and 10 freeze thaw cycles by virus titration in HEK 293 cell cultures (described in 1.1.2). In parallel, the hydrodynamic radii of the adenoviral particles were measured by DLS.

2.1.3 Dynamic Light Scattering (DLS) Measurement

DLS was carried out on samples taken before freeze drying directly after re-buffering compared to an untreated positive control corresponding to an aliquot of the adenoviral stock solution stored at −80° C. as well as on samples after reconstitution of the adenoviral vector formulations. In the latter case, DLS was carried out either immediately after freeze drying (t=0) or at the relevant time points upon storage at 25° C. (21 days, 42 days) and at 40° C. (7 days, 28 days).

To this end, 5 µl of the samples were pipetted into a special DLS cuvette and analysed in a DynaPro Nanostar DLS instrument (Wyatt Technology Europe GmbH; Dernbach; Germany). For each experimental formulation, a blank measurement was performed under the same conditions. The DLS measurements were performed with acquisition times between 20 and 40 seconds in 10 or 20 cycles. The resulting correlation curves were analysed using the DynaPro DLS software.

2.2 Results

The in vitro infectivity assay revealed that composition 1 fully retained the infective titers of both adenoviral vector preparations from process step 1 and step 2 (FIG. 3) compared to the positive control (dashed line in FIG. 3). Re-buffering of the adenoviral vector preparations immediately after the ultracentrifugation step (process step 1) in composition 2 also fully retained the infectivity of the adenoviral vector preparation. Interestingly, composition 2 used after process step 2, resulted in a loss of approximately two log levels of the initial titer (FIG. 3).

Upon additional freeze and thaw cycles (five and ten), composition 1 retained the full infective titer, regardless of the production process step and time point of re-buffering (FIGS. 4 A and B). In contrast, composition 2 resulted in remarkably different effects when prepared in the two different process steps 1 and 2. The infective titers of composition 2 samples obtained according to process step 2 significantly further decreased after five and even stronger after ten freeze and thaw cycles (FIG. 4 B). When the adenoviral vectors were formulated at the earlier process step 1 in composition 2, only a minor titer loss was observed after five freeze and thaw cycles. Ten freeze and thaw cycles resulted in a stronger decrease but to a minor extent compared to the preparation in process step 2 (FIG. 4 A).

In parallel to the determination of the infective titers before and after repeated freeze and thaw cycles, the hydrodynamic radii of the corresponding adenoviral particles were analyzed using Dynamic Light Scattering (DLS) (FIG. 5). Re-buffering of the adenoviral vector preparation directly after the purification step using ultracentrifugation (preparation step 1) resulted in the complete retention of the hydrodynamic radii of the viral particles in both compositions (FIGS. 5 A and B) confirming the complete retention of the corresponding in vitro infectivity (FIG. 3). In the case of composition 1, after re-buffering the adenoviral vector preparation according to process step 2 a slight increase of the hydrodynamic particle radii was observed (FIG. 5 C) which is in accordance with the infectivity results shown in FIG. 3. In contrast, re-buffering of the adenoviral vector preparation in composition 2 corresponding to processing step 2 resulted in a remarkable increase of the hydrodynamic radius of the adenoviral particles (FIG. 5 D) accompanied by the formation of higher order aggregates that may explain the loss of function in the in vitro infectivity tests (FIG. 3).

In summary and conclusion, composition 1 generally exhibited excellent stabilizing efficacy for the adenoviral vector particles during both applied early production steps. In contrast, although composition 2 showed stabilizing efficacy when used directly after ultracentrifugation, reduced stabilizing efficacy was observed when used later in the production process as compared to composition 1.

The DLS data correlate with the in vitro infectivity data. This leads to the conclusion that the use of specifically tailored stabilizing compositions based on amino acids early in the production process of viral vector compositions is important for the stability during further processing steps in biopharmaceutical manufacturing.

EXAMPLE 3

The analysis of the molecular integrity and viscosity of highly concentrated therapeutic antibody formulations during processing and liquid storage showed that specific amino acid and sugar compositions reduced the propensity for aggregation and particularly fragmentation of antibodies in a model for drug substance to drug product processing.

3.1 Materials and Methods

Compositions 3 and 4 contained the 4 basic amino acids arginine, glycine, tryptophan and histidine in a concentration according to the sum of the amino acids to 50 g/l. In the case of composition 3 the amino acid composition was in combination with 80 g/l trehalose and in the case of composition 4 in combination with 32.2 g/l trehalose. As additional compounds the compositions 3 and 4 contained 1.5 g/l methionine and 0.4 g/l polysorbat 20. Composition 4 contained two additional compounds, a chelating agent EDTA and an antioxidant ascorbic acid. The resulting sum of excipients was 131.5 g/l in the case of composition 3 and 85 g/l in the case of composition 4. The ratio of the sum of basic amino acids to trehalose was in composition 3 1:1.55 (w/w) with trehalose in excess whereas in composition 4 the ratio of the basic amino acids to trehalose was 1.6:1 (w/w) with the amino acids in excess. The ratio of the antibody to the sum of excipients was 1:0.9 (w/w) in composition 3 and 1:1.4 (w/w) in composition 4. The pH value was adjusted to 5.5.

As a model protein, the commercially available liquid therapeutic highly concentrated antibody Herceptin® (Roche; Basel; Switzerland) containing trastuzumab in a concentration of 120 mg/ml in the original supplier formulation (79.45 g/l trehalose; 3.13 g/l histidine buffer 20 mM; 1.49 g/l methionine; 0.4 g/l polysorbat 20; 0.024 g/l rHuPh20 (recombinant human hyaluronidase), pH 5.5) was used.

3.1.1 Sample Preparation

The samples of the untreated antibody formulation in the original liquid supplier formulation were directly aliquoted in sterile HPLC vials from the original container for storage at 25° C., 30° C. and 40° C. Another part of the original liquid supplier formulation of trastuzumab at an antibody concentration of 120 mg/ml was re-buffered using dialysis at 2-8° C. into the compositions according to the invention. The resulting formulations were sterile filtrated, aliquoted in sterile HPLC vials and stored at 25° C., 30° C. and 40° C. The aggregation and fragmentation before storage, directly after sample preparation, and at indicated time points during storage were analyzed using SEC.

3.1.2 Size Exclusion Chromatography (SEC)

3.1.2 Size Exclusion Chromatography (SEC)

Protein aggregation and fragmentation were quantified by SEC. Analytics were performed on an UHPLC system UltiMate3000 (Thermo Scientific; Darmstadt; Germany) equipped with a UV-280 nm detector and a TSK-gel G3000SW$_{XL}$ 7.8×300 mm column (Tosoh Bioscience, Tokyo, Japan) at 30° C. and with a flow rate of 0.5 ml/min. Prior to the SEC analysis, the samples containing 25 mg/ml antibody or higher concentrations according to the other examples were diluted to reach a concentration of 2.5 mg/ml IgG using the SEC running buffer PBS and aliquoted into special HPLC vials. The injection volume was 25 μl. The running buffer for SEC was Dulbecco's PBS pH 7.1 (PAA Laboratories, Pasching, Austria). Molecular weight standards (BSA, Thermo Scientific; Waltham, Mass., USA) and a placebo buffer were run in each sequence. Quantification of aggregation and fragmentation in % was determined by comparing the area under the curves of the monomer peaks, the sum of the high molecular weight species and the sum of the low molecular weight species using the Chromeleon 7 Chromatography Data Software (Thermo Scientific, Germany).

3.1.3 Viscosimetry

After sample preparation according to paragraph 5.1.1 the viscosities of the highly concentrated antibody formulations based on amino acid compositions 3 and 4 compared to the viscosity of the untreated liquid original supplier formulation were determined using a falling ball viscosimeter (Anton Paar GmbH; Ostfildern-Schamhausen; Germany). After determination of the density of a highly concentrated protein sample (120 mg/ml) and the calibration of the capillary with water at 20° C. using the falling angle of 70°, the ball was introduced into the capillary and approximately 500 μl of the antibody formulations were carefully filled into the capillary. The filled capillary was inserted into the capillary block of the instrument and samples were measured as ten separate assays at 20° C. and a falling angle of 70°.

3.2 Results

Sample Preparation

The SEC profile of the untreated liquid trastuzumab formulation from the original container showed only a small aggregate peak with 0.19%, a monomer peak with 99.77% and 0.04% fragments. After re-buffering of this formulation in the amino acid based compositions 3 and 4 according to paragraph 3.1 comparable SEC profiles were analyzed, suggesting a stabilizing effect of the amino acid based formulations on the antibody during the process of re-buffering (FIG. 6) that was more pronounced during the subsequent storage at elevated temperatures (FIG. 8 and next paragraph).

Liquid Storage

Already after 1.5 days storage at 40° C. in the original untreated liquid supplier formulation, an increase in aggregate formation was determined (0.22%) and a slight increase in fragmentation was found (0.09%). The monomer peak was slightly decreased to 99.69%. In contrast, the storage for 1.5 days at 40° C. of the antibody in two different amino acid based compositions 3 and 4 according to paragraph 3.1 revealed a decreased propensity of the antibody for aggregation and to a minor extent for fragmentation (FIG. 8 A). In composition 3, an excess of trehalose over the amino acids with an amino acid to trehalose ratio of 1:1.55 (w/w) led to an aggregate content after storage for 1.5 days at 40° C. of about 0.16% and 0.06% fragments. Storage for 1.5 days at 40° C. in composition 4 containing an amino acid to trehalose ratio of 1.6:1 with amino acids in excess led to the formation of 0.16% aggregates and 0.05% fragments. After storage for 12 days at 40° C. in the original liquid supplier formulation the aggregates and fragments further increased (0.26% aggregates and 0.27% fragments). In composition 3, the aggregates increased after storage of 12 days at 40° C. only to 0.20% and the fragments to 0.29%. In composition 4, the aggregate content was only 0.18% and the fragment content increased only to 0.20% (FIG. 8 B). After storage of 21 days at 30° C. the aggregate content in the original supplier formulation also increased to 0.26% and the fragmentation was 0.13%. Storage for 21 days at 30° C. in composition 3 as well as in composition 4 revealed a decreased aggregation propensity of the antibody (0.18% in composition 3 and 0.16% in composition 4). The increase in the fragmentation of the antibody in composition 3 (0.15%) was comparable to the original formulation and in composition 4, the fragment content was decreased to 0.09% (FIG. 8 C). Data after longer periods of storage at 40° C. confirmed these observations. After storage for 42 days at 40° C. in the original formulation aggregation increased to 0.53% and fragmentation to 0.8%. In contrast, in composition 3 and composition 4 the content of aggregates after this storage period was 0.37% and 0.36%. Moreover, fragmentation was only 0.72% and 0.66%, respectively.

These results suggest that the amino acid based formulations have a stronger stabilizing efficacy than the original formulation during storage at 40° C. and 30° C. against both the formation of aggregates and particularly in composition 4 the formation of fragments. The results further indicate that particularly composition 4, with amino acids in the excess over trehalose showed better stabilization against aggregation and fragmentation compared to composition 3. This observation was confirmed after storage of 3 months at 30° C. In the original formulation the aggregate content was 0.35% whereas in composition 3 the aggregate content was 0.26% and in composition 4 the aggregate content was 0.20%. The fragmentation in the original formulation was 0.40%, in composition 3, 0.46% and in composition 4 only 0.33%. Quantitative statistical analysis of the course of liquid storage of highly concentrated antibody formulations (120 mg/mL) at accelerated aging conditions for 3 months at 30° C. further substantiated the above findings. Accelerated aging (FIG. 15) in the original liquid formulation demonstrated a significantly ($p<0.01$) higher degree of aggregation compared to composition 3 and composition 4 (FIG. 15A), in line with formulation viscosities (see below and FIG. 15). In contrast, fragment formation during storage was similar between the original formulation and composition 3, but remarkably reduced ($p<0.05$) in composition 4 (FIG. 15A). The associated decrease of the monomer peak was limited in composition 3 ($p<0.01$) and was even less ($p<0.01$) in composition 4 (FIG. 15A).

The stabilizing efficacy of composition 4 with a ratio of amino acids to trehalose of 1.6:1 (w/w) was confirmed by the following examples.

In addition, analysis of the chemical degradation pattern upon the course of liquid storage of highly concentrated antibody formulations (120 mg/mL) at accelerated aging conditions for 3 months at 30° C. in composition 3 and 4 compared to the original formulation using CEX-HPLC further highlighted the advantageous effect of an adjustment of the base amino acid compositions e.g. by addition of sugar in an appropriate ratio and one or more antioxidant. As with higher concentrated (120 mg/mL) trastuzumab, composition 3 led to a reduction in basic species (FIG. 16; $p<0.05$). Therefore, the balancing of the amino acid:sugar ratio enabled the limitation of basic chemical degradation products during liquid storage of highly concentrated trastuzumab.

This data further substantiate the claimed invention that the adjustment of the applied basic amino acid composition comprised of the at least three amino acids arginine, glycine, histidine and/or tryptophan used during the early drug substance processing steps according to the requirements of the specific biomolecule (e.g. final concentration and viscosity of the drug product) stabilizes the biomolecule during further processing such as filling, freeze drying, storage of the dried or the liquid product.

Viscosity Measurements

The measured dynamic viscosities in the highly concentrated antibody formulations based on amino acids were found to be remarkably reduced compared to the corresponding viscosity of the untreated liquid original supplier formulation. The dynamic viscosity in composition 3 was 4 mPa*s and in composition 4 was 3.5 mPa*s. In contrast, the dynamic viscosity in the highly concentrated liquid original supplier formulation was 4.8 mPa*s (FIG. 9).

Composition 4 and the original supplier formulation contained the antibody in an approximately comparable antibody to excipient ratio of 1.4:1. (w/w) But, in composition 4 the adjustment of the amino acid to trehalose ratio and concomitant of the corresponding antibody to excipient ratio resulted in an impact on both the stabilizing efficacy during liquid storage at elevated temperatures and in a remarkable decrease of the viscosity of the formulation compared to the original formulation. Already the adjustment of the amino acid to trehalose ratio in composition 3 and the resulting antibody to excipient ratio resulted in an increased stabilizing efficacy and in a decrease in the formulation viscosity compared to the original formulation but to a minor extent in comparison to the further adjustments resulted in the effects of composition 4.

Thus, these data further substantiate the finding that the combination of amino acids with trehalose in a balanced ratio and the simultaneous adjustment of the ratio antibody to the sum of excipients have a strong impact on the stabilizing efficacy of the formulation concerning aggregation and particularly of fragmentation of the antibody during liquid storage at elevated temperatures. Moreover, beside the above mentioned stabilizing efficacy the adjustment of the compositions in this manner results in a significant decreased formulation viscosity of highly concentrated therapeutic antibody formulations.

EXAMPLE 4

The analysis of the molecular integrity of highly concentrated therapeutic antibody formulations during processing and liquid storage showed that specific amino acid and sugar compositions as well as amino acid to sugar ratios (w/w) reduced the propensity for aggregation and particularly fragmentation of antibodies in a model for drug product stability.

4.1 Materials and Methods

Composition 3 and 4_1 are similar formulations applied in Example 5 according to paragraph 5.1. But in the case of composition 4_1 the pH adjustment to pH 5.5 was performed using HCl instead of citric acid. Both compositions contained the similar ratios of the sum of amino acids to trehalose according to paragraph 5.1 in Example 5. Composition 4_2 was also a variant of composition 4 according to paragraph 5.1 of Example 5. Composition 4_2 contained the 4 basic amino acids arginine, glycine, tryptophan and histidine under addition of an additional amino acid alanine. In composition 4_2 the sugar fraction was a mixture of trehalose and saccharose in a ratio of 3:1 (w/w). The amount of methionine was slightly increased to 3.5 g/l and addition excipients, e.g. a chelating agent EDTA and ascorbic acid were further supplied.

The ratio of amino acids to sugar was slightly reduced in composition 4_2 to 1:1 (w/w). In the original formulation, the antibody to excipient ratio was 1.6:1 (w/w), in composition 3, 1:1.1 (w/w); in composition 4_1, 1.76:1 (w/w) and in composition 4_2, 1.12:1 (w/w) The pH was adjusted to 5.5.

As a model protein, the commercially available freeze-dried Herceptin® (Roche; Basel; Switzerland) was used. Preparation of the samples was performed by reconstitution of the commercially available freeze-dried Herceptin® in a desired volume of water.

4.1.1 Sample Preparation

The resulting formulation was dialysed at 2-8° C. against the composition of the original liquid formulation (79.45 g/l trehalose; 3.13 g/l histidine buffer (20 mM); 1.49 g/l methionine; 0.4 g/l polysorbat 20; pH 5.5) and against the amino acid based compositions according to paragraph 6.1. Subsequent concentration of the resulting IgG formulations were done to obtain 135 mg/ml antibody in the original formulation, 145 mg/ml antibody in composition 3, 150 mg/ml antibody in composition 4_1 and 151 mg/ml antibody in composition 4_2. Subsequently, the formulations were sterile filtrated, aliquoted in sterile HPLC vials and stored at 5° C., 25° C., 30° C. and 40° C. The aggregation and fragmentation before storage, directly after sample preparation, and at indicated time points during storage were analyzed using SEC.

4.1.2 Size Exclusion Chromatography

SEC was performed according to paragraph 3.1.2.

4.2 Results

Liquid Storage

Already after the initial storage time of 8 days at 40° C. in the original formulation, the formation of aggregates and fragments was remarkably increased (0.77% aggregates and 0.75% fragments versus 0.35% aggregates and no fragments before liquid storage, respectively). In contrast, storage for 8 days at 40° C. in all amino acid based formulations tested clearly limited aggregation and fragmentation. In composition 3, aggregation was 0.39% and fragmentation was 0.51%. In composition 4_1, aggregation was 0.38% and interestingly, fragmentation was further reduced to 0.31%. In composition 4_2, a slightly further reduction of aggregation and fragmentation was detected (0.36% aggregates and 0.28% fragments) as depicted in FIG. 10 A.

This data confirmed the results of the previous experiment concerning the efficacy of composition 4 (composition 4_1 in this Example 4) to further reduce particularly the formation of fragments during liquid storage.

Comparable results were found after storage for 1 month at 30° C. Storage in the original formulation led to 0.53% aggregates and 0.50% fragments. The corresponding SEC analysis for composition 3 revealed 0.4% aggregates and 0.51% fragments. Liquid Storage for 1 month at 30° C. in composition 4_1 resulted in remarkably decreased aggregate formation (0.35%) and fragment formation (0.30%).

Comparable results were shown in composition 4_2 with an aggregate formation of 0.32% and fragment formation of 0.31% (FIG. 10 B).

After liquid storage for 6 months at 25° C., aggregation of the antibody in the original formulation was increased to 0.98% and fragmentation reached 1.00%. In composition 3, a smaller increase in aggregation to 0.71% and in fragmentation to 0.9% was shown. In both compositions, 4_1 and 4_2, only nearly the half of aggregation and fragmentation compared to the original formulation was found; composition 4_1: 0.58% aggregates and 0.53% fragments and composition 4_2: 0.58% aggregates and 0.56% fragments (FIG. 11 A).

Comparable results were found after liquid storage for 6 months at 2-8° C. with smaller changes in aggregation and fragmentation compared to the storage at 25° C. (FIG. 11 B).

Quantitative statistical analysis of the whole course of storage of highly concentrated antibody formulations (150 mg/mL) for 6 months at 25° C. in composition 4_1 and 4_2 compared to the original formulation revealed significantly reduced aggregates and fragments (p<0.01) and retained a stable monomer peak during storage for 6 months at 25° C. (FIG. 15 B).

The additional analysis of the chemical degradation profile of the highly concentrated antibody formulations during storage for six months at 25° C. in composition 4_1 and 4_2 compared to the original formulations using CEX HPLC underlined the previous SEC results and the results of the previous examples. After six months storage of 150 mg/mL trastuzumab at 25° C., lower amounts of basic species were observed for composition 4_1 and 4_2 (p<0.05, p<0.01) compared to the original formulation (FIG. 16 B). Interestingly, in conjunction with the limited increase of basic species, the same formulations, composition 4_1 and 4_2 also limited the increase of acidic species as compared with compositions 3 and 4 as shown in example 3. As a consequence, the main peak relative AUC was stabilized during storage of highly concentrated trastuzumab, especially by composition 4_2.

In summary, these results confirm that the balanced mixture of amino acids and sugar is necessary for the prevention of antibody aggregation and fragmentation during liquid storage and that the adjustment of the ratio of amino acids to sugar at least to amino acids in excess and more preferred amino acids and sugar in the ratio approx. 1:1 (w/w) resulted in a further increased stabilizing efficacy.

EXAMPLE 5

The analysis of the molecular integrity and viscosity of highly concentrated therapeutic antibody formulations during processing and liquid storage showed that specific amino acid and sugar compositions as well as amino acid to sugar ratios (w/w) as well as the adjustment of tryptophan and histidine concentrations and ratios (w/w) reduced the propensity for aggregation and particularly fragmentation of antibodies in a model for drug product stability.

5.1 Materials and Methods

Compositions 4_3, 4_4 and 4_5 were obtained by concentrating composition 4_2 from the previous example. Composition 4_3 is similar to composition 4_2 according to paragraph 4.1 in Example 4, but the sum of excipients was reduced from 135 g/l to 90 g/l in composition 4_3. The amino acid to sugar mixture ratio was preserved to 1:1 (w/w) and the antibody to excipient ratio was 2.22:1 (w/w). In composition 4_4 the similar mixture of amino acids and sugar mixture was used compared to composition 4_2 in paragraph 4.1 in Example 4 and to composition 4_3 in this Example 5, but the amino acids to sugar ratio was increased to 3.4:1 (w/w) and the antibody to excipient ratio was increased to 3.33:1 (w/w). In composition 4_5 also the same mixture of excipients was used, but the amino acid concentration of histidine was increased and the concentration of tryptophan was decreased. The ratio trehalose to saccharose was reduced to 2:1 (w/w) compared to 3:1 (w/w) in the previous experiments, and the amino acid to sugar ratio was reduced to 1.5:1 (w/w). The antibody to excipient ratio was comparable to composition 4_3 adjusted to 2.22:1 (w/w). The antibody to excipient ratio was 2.4:1 (w/w) in the case of the original liquid suppler formulation. The pH value was adjusted to 5.5.

As a model protein, the commercially available liquid therapeutic highly concentrated antibody Herceptin® (Roche; Basel; Switzerland) according to paragraph 5.1 in Example 5 was used.

5.1.1 Sample Preparation

In order to get higher concentrated trastuzumab preparations compared to the Examples 3 and 4, the antibody in the original liquid supplier formulation was concentrated to obtain 200 mg/ml and the antibody in compositions 4_3, 4_4 and 4_5 were concentrated after an additional dialysis step at 2-8° C. Highly concentrated formulations were prepared for the subsequent storage experiment by sterile filtration and subsequent aliquoting in sterile HPLC vials. The highly concentrated samples were stored at 5° C., 25° C., 30° C. and 40° C. The aggregation and fragmentation were analyzed before storage, directly after sample preparation, and at indicated time points during storage using SEC.

5.1.2 Size Exclusion Chromatography

SEC was performed according to paragraph 3.1.2.

5.1.3 Measurements of Viscosities of the Highly Concentrated Antibody Formulations The viscosities of the highly concentrated antibody formulations according to this example were measured using a falling ball viscosimeter according to paragraph 3.1.3 in example 3.

5.2 Results

Sample Preparation

The SEC profile of the untreated liquid trastuzumab formulation from the original container showed only a small aggregate peak with 0.19%, a monomer peak with 99.77% and 0.04% fragments (example 3; FIG. 6). In contrast, the corresponding SEC profile after concentration of this commercially available liquid therapeutic highly concentrated Herceptin® to an antibody concentration of about 200 mg/ml (0.04 mg/ml rHuPH20) led to a remarkably different SEC profile of the concentrated sample. The formation of aggregates was increased to a percent area of about 1.9% of the peaks corresponding to aggregates. The percentage area of the corresponding monomer peak was accordingly decreased to 98.07%. The fragmentation was not changed. Similar concentration of the antibody formulated in the amino acid based stabilizing compositions after an additional re-buffering step using dialysis resulted in SEC profiles comparable to the untreated original liquid trastuzumab formulation with aggregates between 0.16 and 0.19% and without changes in fragmentation. The percent area of the monomer peak was about 99.8%. Moreover, the corresponding SEC chromatograms showed a clear baseline separation between the peak at an elution time of 14 min corresponding to the aggregates (dimers) of the antibody and the main peak at an elution time of approx. 16.5 min corresponding to the structural intact antibody monomers (FIG. 7).

Liquid Storage

Interestingly, during the whole course of liquid storage of these particular highly concentrated formulations at different temperatures the fragmentation of the antibody was only a minor event in the original formulation as well as in the amino acids based compositions according to the invention. This effect might be a result of the increased antibody to excipient ratios and was already observed in a previous experiment with low concentrated trastuzumab formulations.

Liquid storage for 3 days at 40° C. resulted in increased aggregation in the original formulation to 2.11% aggregates and 0.1% fragments. In composition 4_3 this storage period resulted in an aggregation of about 0.22% and fragmentation of about 0.07%. Storage for 3 days at 40° C. in composition 4_4 resulted in a formation of aggregates to about 0.26% and fragment formation of about 0.06%. In composition 4_5, the aggregate content was only 0.18% and the fragmentation was analyzed to about 0.08% (FIG. 12 A).

Further liquid storage for 14 days at 40° C. resulted in an aggregate content of about 2.28% in the original formulation and 0.33% fragmentation. In the composition 4_3 the aggregation was only 0.43% and the fragmentation was similar to 0.33%.

Comparable results were obtained in composition 4_4 with aggregation of about 0.40% and fragmentation about 0.33%. Also in composition 4_5, comparable results were found for aggregate formation (0.27%) and fragment formation at 0.34% (FIG. 12 B).

After long term liquid storage for 1½ months at 30° C. in original formulation the aggregate formation was 1.84% and fragment formation 0.25%. In composition 4_3, the aggregation was only 0.28% and fragmentation 0.23% comparable to the original formulation. In composition 4_4, the aggregate formation was slightly increased to 0.38% and the fragment formation was about 0.22%. In composition 4_5, the aggregation after storage for 1½ months at 30° C. was only 0.22% and the fragmentation reached 0.25% (FIG. 13 A).

Real time liquid storage for 3 months at 25° C. resulted in an aggregate formation of about 1.89% in the original formulation and 0.25% fragmentation. In composition 4_3, the long term storage at 25° C. resulted in 0.35% aggregates and 0.22% fragments. The aggregation was slightly increased in composition 4_4 after 3 months storage at 25°

C. to 0.40% and the fragment formation was retained at 0.22%. In composition 4_5, the lowest aggregation was found with 0.27% and a comparable fragmentation with 0.25% was achieved (FIG. 13 B).

At all analytic time points during liquid storage of the antibody at different temperatures composition 4_5 showed the best stabilizing efficacy against aggregation. In composition 4_3 and composition 4_4, the aggregation propensity of the antibody during liquid storage at different temperatures was more or less comparable whereas in composition 4_5 the antibody showed the lowest aggregate formation at the indicated analytic time points. Between composition 4_3 and composition 4_4 the former showed slightly superior stabilizing efficacy.

Evaluation of the propensity of the antibody for aggregation and fragmentation and the associated loss of monomer peak during liquid storage of highly concentrated antibody formulations (200 mg/mL) in compositions 4_3, 4_4 and 4_5 compared to the original formulation for 3 months at 25° C. further confirmed the above detailed results.

Aggregate peaks (elution time≈14 minutes) corresponding to antibody dimers were significantly reduced in composition 4_5 ($p<0.01$; $p<0.0001$), and to a minor extent in composition 4_3 and composition 4_4 ($p<0.01$, $p<0.001$) compared to the original formulation (FIG. 15 C). In composition 4_4, (highest antibody:excipient ratio of 3.33:1) slightly stronger aggregation associated with an increase in formulation viscosity compared to composition 4_3 and particularly to composition 4_5 was found (FIG. 15 C). No relevant fragmentation was observed with 200 mg/mL (FIG. 15 C) which might be due to the increased antibody to excipient ratios as already observed with low concentrated formulations (see below and FIG. 14). The monomer peak in the amino acid based formulations was almost completely retained during liquid storage at 25° C. Composition 4_3 and 4_4 demonstrated the lowest increase in fragmentation compared to the original formulation and composition 4_5 ($p>0.05$; FIG. 15 C).

These results suggest that both changes in the composition, the concentration changes of histidine and tryptophan and the change of the ratio of trehalose to saccharose had a positive impact on the stabilizing efficacy particularly on the aggregation. Fragmentation was slightly more reduced in the amino acid based compositions containing higher concentrations of tryptophan and histidine in the buffer concentration (see previous examples and composition 4_3 and 4_4 compared to composition 4_5). The ratio amino acids:trehalose/saccharose mixture was slightly increased in composition 4_4 (1.5:1 (w/w)) compared to 1:1 (w/w) in composition 4_3 derived from composition 4_2 of the previous experiment.

Thus, the adjustment of the concentrations of tryptophan and histidine in line with the adjustment of the amino acid to sugar ratio is important for preventing aggregation and fragmentation in conjunction during liquid storage of an antibody. Furthermore, the strong increase of the antibody to excipient ratio to 3.3:1 (w/w) in composition 4_4 led to a slight increase in the aggregation propensity of the antibody during liquid storage. The parallel adjustment of the antibody to excipient ratio was shown to have an impact on the stabilizing efficacy of the amino acid based compositions according to the invention.

Similar observations were made by analyzing the chemical degradation of the antibody during liquid storage at elevated temperature. To this end, the samples were stored for 3 months at 25° C. and analyzed using CEX. Composition 4_4 and 4_5 resulted in a not significant increased formation of acidic charge variants (lowest degree in composition 4_5) but a reduced formation of basic charge variants particularly in the case of composition 4_3 and 4_4 ($p<0.05$) compared to the original formulation. The loss of the main peak area was partly prevented by composition 4_3 and 4_4 ($p>0.05$) and was comparable to the original formulation in composition 4_5 (FIG. 16 C). The w/w ratio between the two selected amino acids histidine and tryptophan was changed iteratively and resulted in modified formation of acidic and basic charge variants (FIG. 16 C).

Viscosity Measurements

For the analysis of the dynamic viscosities of higher concentrated antibody formulations compared to example 5 the concentrations of the formulations were adjusted to 200 mg/ml and 220 mg/ml according to the sample preparation method in paragraph 7.1.1 of this example (FIG. 14). The dynamic viscosity of the highly concentrated antibody formulation in the original liquid supplier formulation (220 mg/ml) was evaluated to 20.53 mPa*s. In the compositions according to the invention 4_3 and 4_5 containing an antibody concentration of 220 mg/ml the measured dynamic viscosities were remarkably reduced to 15.2 mPa*s in composition 4_3 and 17.6 mPa*s in composition 4_5. A slight increase in the viscosity was evaluated in the case of composition 4_4 with 22.4 mPa*s. This can be a result of the high antibody to excipient ratio of 3.7:1 in this composition compared to the compositions 4_3 and 4_5. The viscosity measurements of the corresponding formulations with antibody concentrations of 200 mg/ml also resulted in clearly reduced viscosities in composition 4_3, 11.2 mPa*s, in composition 4_4 15.4 mPa*s and in composition 4_5 11.6 mPa*s. In the case of the antibody concentration of 200 mg/ml the composition 4_4 showed also a slightly increased viscosity compared to the other formulations suggesting the same trend evaluated in composition 4_4 with the antibody concentration of 220 mg/ml. Together with the slightly decreased stabilizing efficacy of composition 4_4 during liquid storage of the highly concentrated antibody (200 mg/ml) these data further substantiate the finding that beside the balanced adjustment of the amino acid to sugar ratio also the balanced adjustment of the antibody to excipient ratio has a significant effect on both, the stabilizing efficacy and the formulation viscosity.

EXAMPLE 6

The analysis of both the molecular integrity as well as the chemical stability during processing and during subsequent liquid storage of highly concentrated antibody formulations showed that specific amino acid and sugar compositions that do not comprise proline were able to reduce the propensity for aggregation during processing as well as during subsequent liquid storage. In particular chemical changes were remarkably reduced compared to the original trastuzumab formulation of the freeze dried product comprising glycine and proline.

6.1 Materials and Methods

Composition 4_1 corresponds to the formulation applied in Example 3 and compositions 4_3 and 4_5 correspond to the formulations applied in Example 5. The stabilizing effect of these formulations was compared to the original liquid supplier formulation (79.45 g/l trehalose; 3.13 g/l histidine buffer 20 mM; 1.49 g/l methionine; 0.4 g/l polysorbat 20; pH 5.5). The pH was adjusted in these formulations to 5.5. In addition, the stabilizing effect of the inventive compositions was compared to the original supplier formulation of the freeze-dried product (20 g/l trehalose; 0.9 mg/ml histidine buffer approx. 5 mM; 0.1 g/l polysorbat 20; pH 6) with addition of the amino acids glycine and proline in accordance with the teaching of U.S. Pat. No. 9,364,542 B2 (Example 16; FIGS. 29 and 30).

As a model drug, commercially available freeze-dried Herceptin® (Roche; Basel; Switzerland), a therapeutic humanized IgG1 monoclonal antibody (trastuzumab), was used. Reconstitution of the freeze-dried drug in the desired volume of water resulted in an antibody concentration of 21 mg/mL in the original supplier formulation (20 g/l trehalose; 0.9 mg/ml histidine buffer approximately 5 mM; 0.1 g/l polysorbat 20; pH 6).

6.1.1 Sample Preparation

The resulting formulation was dialysed at 2-8° C. against the composition of the original liquid formulation (79.45 g/l trehalose; 3.13 g/l histidine buffer, approx. 20 mM; 1.49 g/l methionine; 0.4 g/l polysorbat 20; pH 5.5) and the original supplier formulation of the freeze-dried product (20 g/l trehalose; 0.9 mg/ml histidine buffer, approx. 5 mM; 0.1 g/l polysorbat 20; pH 6), wherein this formulation additionally contained the amino acids glycine and proline in the concentrations described in U.S. Pat. No. 9,364,542 B2 (Example 16).

In parallel, dialysis was performed against the amino acid based compositions of the present invention as detailed in paragraph 8.1 Subsequent concentration of the resulting IgG formulations was performed in order to obtain 200 mg/ml antibody. Subsequently, the formulations were sterile filtrated, aliquoted in sterile HPLC vials and either stored at 25° C. or 40° C., or, for short term storage, at 55° C., as described in U.S. Pat. No. 9,364,542 B2 (Example 16; FIGS. 29 and 30). The aggregation and fragmentation before storage, directly after sample preparation, and at the indicated time points during storage were analyzed using SE-HPLC. The chemical changes in the protein molecules upon liquid storage were analyzed using CEX-HPLC.

6.1.2 Size Exclusion Chromatography

SEC was performed as described in section 3.1.2 above.

6.1.3 Cation Exchange Chromatography

CEX-HPLC (UV-280 nm detector; UHPLC Ulti-Mate3000 Thermo Scientific, Germany) and a cation exchange column TSK-gel CM-STAT 4.5×100 nm (Tosoh Bioscience, Tokyo, Japan) was used at 45° C. and with a flow rate of 0.8 ml/min (injection volume 25 µl). Prior to the CEX-HPLC analysis, samples were diluted to 2.5 mg/mL IgG in running buffer A (10 mM sodium phosphate buffer pH 7.5). The immobilized trastuzumab molecules were eluted in a sodium chloride gradient using 0% to 30% buffer B (10 mM sodium phosphate buffer pH 7.5; 100 mM sodium chloride). Relative areas under the curves (% AUC) were determined with the Chromeleon 7 Chromatography Data Software (Thermo Scientific).

6.2 Results

Sample Preparation

During the course of sample preparation using dialysis and subsequent concentration in order to obtain an antibody concentration of 200 mg/mL, the previously obtained results of Examples 3 and 5 were confirmed. Specifically, when the preparation process was carried out in one of the inventive compositions (composition_4_1, composition_4_3 or composition_4_5), a retention of the amount of aggregates and monomers was obtained that is comparable to the trastuzumab standard (0.65-0.70% aggregates; 99.30-99.35% monomers). These results suggest that the retention of the structural integrity of the antibody prepared in the inventive compositions is comparable to the levels of structural intact antibodies before preparation (FIG. 17).

The process of preparing the highly concentrated antibody in the original liquid supplier formulation, on the other hand, led to an increase in the percent area of the peak corresponding to the antibody dimers (i.e. at a retention time of 14 min) to about 0.84% and a corresponding reduction of the monomer peak to about 99.16%. Moreover, the corresponding preparation process of the highly concentrated trastuzumab in the original supplier formulation of the freeze-dried product in combination with the additional amino acids glycine and proline also resulted in a strong increase in the formation of aggregates to about 0.79% and, consequently, in the reduction of the monomer peak to 99.21%.

Liquid Storage—SE-HPLC

Short term liquid storage of the antibody under extreme (i.e. physiologically and pharmaceutically irrelevant high) temperature conditions (24 h at 55° C.) as carried out in U.S. Pat. No. 9,364,542 B2 revealed an efficient stabilizing effect of the inventive compositions against aggregation and fragmentation compared to the original liquid supplier formulation as well as to the original supplier formulation of the freeze-dried product with glycine and proline as additives. The percent areas of the peaks corresponding to the formation of aggregates were nearly completely retained in the inventive compositions, particularly in composition_4_3 and composition 4_5, comparable to the trastuzumab standard stored at −80° C. (0.65-0.70% aggregates; 99.30-99.35% monomers).

In contrast, short term storage for 24 h hat 55° C. in the original supplier formulation with the additives glycine and proline and, more pronounced, in the original liquid supplier formulation, resulted in a remarkably increased aggregation with a more pronounced decrease in the percent area of the monomer peak (FIG. 18; Table 1; 2; t=0). As a result of the short term storage for 24 h at 55° C., fragmentation in the original liquid supplier formulation as well as in the original supplier formulation of the freeze-dried product with glycine and proline as additives was also slightly increased in comparison to the antibody formulated in the inventive compositions (Table 1).

Liquid storage for 7 days, 14 days, 28 and 42 days, respectively, at 40° C./75% RH revealed an increased propensity of the antibody for both aggregation as well as fragmentation in all formulations but to different extents. Most strikingly, formulation of the antibody in the inventive compositions (composition_4_1, composition_4_3 and composition_4_5) resulted in a remarkably reduced aggregation and fragmentation as compared to the original liquid supplier formulation as well as to the original supplier formulation in combination with the amino acids glycine and proline (FIGS. 18 C and D; Tables 1 and 2).

Moreover, liquid storage for 14 days and 28 days at 25° C. further substantiated the observation that the inventive solutions are able to prevent aggregation and fragmentation upon the course of storage at ambient and elevated temperatures and even at extreme temperature conditions such as 55° C. (Table 3, 4).

Liquid Storage—CEX-HPLC

In the U.S. Pat. No. 9,364,542 B2 only the formation of macroscopic insoluble aggregates of the antibody using turbidity measurements and, in some examples, the analysis of the formation of soluble aggregates using SE-HPLC during short term storage under physiologically and pharmaceutically irrelevant high temperature conditions such as 55° C. was analyzed. Here, the extent of chemical changes in the antibody molecule during short term storage at 55° C., as well as during long term storage at 40° C. and 25° C., was additionally analyzed. Already short term storage of trastuzumab for 24 h at 55° C. triggered chemical changes in all formulations to varying degrees.

In the original supplier formulation of the freeze-dried product with addition of the amino acids glycine and proline (Original+G/P), a significantly increased percentage of acidic charge variants of the antibody (>30%) was observed during short term storage at 55° C. This observation was associated, in consequence, with a remarkable decrease of the percent area of the main peak (53.23%) as shown in Table 5.

In contrast, short term storage of the antibody in the compositions according to the invention resulted in a remarkably reduced formation of acidic charge variants (e.g. <23% in composition_4_5). The increase of acidic charge variants provides evidence for protein deamidation or glycation and is an important criterion for negative selection of test formulations in industrial manufacturing standards. Therefore, different compositions according to the invention were tested in comparison with Original+G/P to study the modifications of acidic charge variants during three day storage at 55° C., up to 21 days at 40° C., and up to two months at 25° C. (FIG. 19). All tested compositions according to the present invention generally resulted in significantly lower acidic charge variants than Original+G/P at all analytic time points and all storage temperatures. As a consequence, the main peaks were accordingly higher in all formulations according to the present invention at all analytic time points and temperatures (Table 5).

EXAMPLE 7

The analysis of the molecular integrity after dialysis, concentration, and subsequent storage of high concentrated antibody formulations (200 mg/mL) by means of SE-HPLC shows the relevance of the at least three amino acid combinations alone or in combination with trehalose to limit the increase of aggregates in manufacturing relevant processing steps and subsequent storage.

7.1 Materials and Methods

Composition 5 contained the two base amino acids histidine and methionine and is similar to composition 8, which corresponds to the original supplier formulation (histidine, methionine, trehalose), except that it does not contain any sugar. Composition 6 comprises the three amino acids histidine, methionine, and glycine without sugar, whereas composition 9 is similar, but contains trehalose. Composition 7 comprises the five amino acids histidine, methionine, alanine, arginine and tryptophan, whereas composition 10 is similar, but contains trehalose.

As a model protein, the commercially available liquid therapeutic highly concentrated antibody Herceptin® (Roche; Basel; Switzerland) containing trastuzumab in a concentration of 120 mg/ml in the original supplier formulation (79.45 g/l trehalose; 3.13 g/l histidine buffer 20 mM; 1.49 g/l methionine; 0.4 g/l polysorbat 20; 0.024 g/l rHuPh20 (recombinant human hyaluronidase), pH 5.5) was used.

9.1.1 Sample Preparation

The liquid therapeutic highly concentrated antibody Herceptin® was dialysed at 2-8° C. against a 5 mM histidine buffer pH 5.5. After determination of the protein concentration and subsequent adjustment of the protein concentration to 100 mg/ml the antibody was formulated into the compositions according to paragraph 9.1 as well as the original liquid supplier formulation by 1 per 5 dilution of the dialyzed high concentrated antibody using 1.25 fold concentrated formulations to antibody concentrations of 20 mg/ml. For experiments with high concentrated antibody formulations selective compositions and the antibody formulated in the original liquid supplier formulation were concentrated up to 200 mg/ml. Subsequently, the formulations were sterile filtrated and aliquoted in sterile HPLC vials and stored at 45° C. for up to 14 days. The aggregation and fragmentation before storage, directly after dialysis, directly after the concentration step, and after storage at seven days and 14 days during liquid storage were analyzed using SE-HPLC.

7.1.2 Size Exclusion Chromatography

SEC was performed according to paragraph 3.1.2.

7.2 Results

Liquid Storage—SE-HPLC

As shown in Table 6, increased aggregation was observed after seven days storage at 45° C. subsequent to previous dialysis and concentration steps. It was surprisingly found that formulations with two amino acids and without sugar in general exhibited the highest values (e.g. 0.65% after seven days; 1.29% after 14 days) compared with compositions comprising three amino acids (0.53% after seven days; 1.11 after 14 days), and compared with compositions comprising five amino acids (0.4% after seven days; 0.88% after 14 days). The main peaks were stabilized accordingly (Table 6). This observation was confirmed when the same amino acid combinations were supplemented with trehalose. Specifically, formulations with two amino acids with trehalose (corresponding to the original formulation) in general exhibited the highest values (e.g. 0.57% after seven days; 1.07% after 14 days) compared with compositions comprising three amino acids (0.43% after seven days; 0.93 after 14 days), and compared with compositions comprising five amino acids (0.34% after seven days; 0.8% after 14 days). The main peaks were stabilized accordingly (Table 6).

Tables

TABLE 1

SE-HPLC analysis of highly concentrated trastuzumab directly after sample preparation (t = 0) and at the indicated time points during liquid storage at 55° C. and 40° C. formulated in the original liquid supplier formulation and in the original supplier formulation of the freeze dried product with addition of the amino acids glycine and proline - quantification of aggregates, monomers and fragments expressed in percent areas under the corresponding peaks in the SE-HPLC chromatograms.

| | original liquid supplier formulation | | | original supplier formulation of the freeze-dried product with amino acid additives glycine and proline | | |
|---|---|---|---|---|---|---|
| | aggregates | monomers | fragments | aggregates | monomers | fragments |
| t = 0 | 0.82 | 99.18 | | 0.78 | 99.23 | |
| 24 h 55° C. | 1.21 | 98.68 | 0.11 | 1.21 | 98.68 | 0.11 |

TABLE 1-continued

SE-HPLC analysis of highly concentrated trastuzumab directly after sample preparation (t = 0) and at the indicated time points during liquid storage at 55° C. and 40° C. formulated in the original liquid supplier formulation and in the original supplier formulation of the freeze dried product with addition of the amino acids glycine and proline - quantification of aggregates, monomers and fragments expressed in percent areas under the corresponding peaks in the SE-HPLC chromatograms.

| | original liquid supplier formulation | | | original supplier formulation of the freeze-dried product with amino acid additives glycine and proline | | |
|---|---|---|---|---|---|---|
| | aggregates | monomers | fragments | aggregates | monomers | fragments |
| 7 d 40° C. | 1.28 | 98.58 | 0.14 | 1.26 | 98.57 | 0.17 |
| 14 d 40° C. | 1.49 | 98.29 | 0.22 | 1.62 | 98.07 | 0.31 |
| 28 d 40° C. | 1.82 | 97.70 | 0.49 | 2.25 | 97.23 | 0.54 |
| 42 d 40° C. | 2.09 | 97.27 | 0.64 | 3.17 | 95.91 | 0.93 |

TABLE 2

SE-HPLC analysis of highly concentrated trastuzumab directly after sample preparation (t = 0) and at the indicated time points during liquid storage at 55° C. and 40° C. formulated in the compositions according to the invention - quantification of aggregates, monomers and fragments expressed in percent areas under the corresponding peaks in the SE-HPLC chromatograms.

| | composition_4_1 | | | composition_4_3 | | | composition_4_5 | | |
|---|---|---|---|---|---|---|---|---|---|
| | aggregates | monomers | fragments | aggregates | monomers | fragments | aggregates | monomers | fragments |
| t = 0 | 0.69 | 99.31 | | 0.70 | 99.31 | | 0.65 | 99.36 | |
| 24 h 55° C. | 0.81 | 99.13 | 0.06 | 0.81 | 99.14 | 0.06 | 0.77 | 99.16 | 0.07 |
| 7 d 40° C. | 0.90 | 99.00 | 0.12 | 0.85 | 99.04 | 0.12 | 0.85 | 98.97 | 0.18 |
| 14 d 40° C. | 1.04 | 98.63 | 0.33 | 0.98 | 98.71 | 0.32 | 0.99 | 98.71 | 0.31 |
| 28 d 40° C. | 1.32 | 98.06 | 0.62 | 1.24 | 98.38 | 0.39 | 1.24 | 98.13 | 0.63 |
| 42 d 40° C. | 1.77 | 97.27 | 0.97 | 1.36 | 97.83 | 0.78 | 1.53 | 97.58 | 0.89 |

TABLE 3

SE-HPLC analysis of highly concentrated trastuzumab directly after sample preparation (t = 0) and at the indicated time points during liquid storage at 25° C. formulated in the original liquid supplier formulation and in the original supplier formulation of the freeze dried product with addition of the amino acids glycine and proline - quantification of aggregates, monomers and fragments expressed in percent areas under the corresponding peaks in the SE-HPLC chromatograms.

| | original liquid supplier formulation | | | original supplier formulation of the freeze-dried product with amino acid additives glycine and proline | | |
|---|---|---|---|---|---|---|
| | aggregates | monomers | fragments | aggregates | monomers | fragments |
| t = 0 | 0.82 | 99.18 | | 0.78 | 99.23 | |
| 14 d 25° C. | 1.23 | 98.77 | 0.05 | 1.15 | 98.79 | 0.07 |
| 28 d 25° C. | 1.19 | 98.73 | 0.08 | 1.18 | 98.72 | 0.11 |
| 42 d 25° C. | 1.27 | 98.63 | 0.11 | 1.28 | 98.62 | 0.12 |
| 2 months 25° C. | 1.28 | 98.57 | 0.16 | 1.44 | 98.28 | 0.30 |

TABLE 4

SE-HPLC analysis of highly concentrated trastuzumab directly after sample preparation (t = 0) and at the indicated time points during liquid storage at 25° C. formulated in the compositions according to the invention - quantification of aggregates, monomers and fragments expressed in percent areas under the corresponding peaks in the SE-HPLC chromatograms.

| | composition_4_1 | | | composition_4_3 | | | composition_4_5 | | |
|---|---|---|---|---|---|---|---|---|---|
| | aggregates | monomers | fragments | aggregates | monomers | fragments | aggregates | monomers | fragments |
| t = 0 | 0.69 | 99.31 | | 0.695 | 99.305 | | 0.65 | 99.36 | |
| 14 d 25° C. | 0.79 | 99.22 | | 0.765 | 99.235 | 0.01 | 0.75 | 99.21 | 0.08 |

TABLE 4-continued

SE-HPLC analysis of highly concentrated trastuzumab directly after sample preparation (t = 0) and at the indicated time points during liquid storage at 25° C. formulated in the compositions according to the invention - quantification of aggregates, monomers and fragments expressed in percent areas under the corresponding peaks in the SE-HPLC chromatograms.

| | composition_4_1 | | | composition_4_3 | | | composition_4_5 | | |
|---|---|---|---|---|---|---|---|---|---|
| | aggregates | monomers | fragments | aggregates | monomers | fragments | aggregates | monomers | fragments |
| 28 d 25° C. | 0.87 | 99.01 | 0.13 | 0.835 | 99.025 | 0.14 | 0.79 | 99.08 | 0.14 |
| 42 d 25° C. | 0.96 | 99.04 | | 0.87 | 99.125 | | 0.85 | 99.20 | |
| 2 months 25° C. | 0.98 | 98.87 | 0.16 | 0.905 | 98.905 | 0.19 | 0.81 | 98.99 | 0.21 |

TABLE 5

Main peaks of CEX-HPLC chromatograms of highly concentrated trastuzumab directly after sample preparation (t = 0) and at the indicated time points during liquid storage at 55° C., 40° C., and 25° C. formulated in the original supplier formulation of the freeze dried product supplemented with the amino acids glycine and proline (original + G/P) and in compositions 4_1, 4_3 and 4_5 according to the present invention. Main peaks are expressed as percent areas under the corresponding chromatogram peaks.

| | original + G/P | composition_4_1 | composition_4_3 | composition_4_5 |
|---|---|---|---|---|
| t = 0 | 67.10 | 68.52 | 67.99 | 68.14 |
| 24 h 55° C. | 53.23 | 58.26 | 57.11 | 56.87 |
| 3 d 55° C. | 32.22 | 41.72 | 41.05 | 40.22 |
| 1.5 d 40° C. | 58.97 | 63.36 | 63.10 | 62.96 |
| 3 d 40° C. | 56.88 | 63.44 | 62.97 | 62.95 |
| 7 d 40° C. | 46.32 | 55.62 | 55.61 | 53.99 |
| 14 d 40° C. | 30.53 | 43.10 | 43.14 | 41.87 |
| 21 d 40° C. | 21.35 | 35.05 | 34.01 | 33.68 |
| 7 d 25° C. | 62.58 | 66.90 | 66.47 | 66.38 |
| 14 d 25° C. | 57.02 | 64.31 | 64.04 | 64.01 |
| 28 d 25° C. | 48.98 | 60.93 | 60.89 | 60.06 |
| 42 d 25° C. | 41.67 | 55.89 | 55.79 | 54.75 |
| 2 months 25° C. | 35.65 | 50.63 | 50.44 | 49.59 |

TABLE 6

SE-HPLC analysis of highly concentrated trastuzumab directly after sample preparation (t = 0) and at the indicated time points during liquid storage at 45° C. formulated in the compositions according to the invention - quantification of aggregates, monomers and fragments expressed in percent areas under the corresponding peaks in the SE-HPLC chromatograms.

| | t = 0 (after dialysis) | | | After concentration step | | | Liquid storage after concentration step 7 d 45° C. | | | Liquid storage after concentration step 14 d 45° C. | | |
|---|---|---|---|---|---|---|---|---|---|---|---|---|
| t = 0 | aggregates | monomers | fragments | aggregates | monomers | fragments | aggregates | monomers | fragments | aggregates | monomers | fragments |
| 2 amino acids w/o sugar | 0.19 | 99.78 | 0.03 | 0.21 | 99.76 | 0.03 | 0.65 | 98.89 | 0.46 | 1.29 | 98.12 | 0.59 |
| 3 amino acids w/o sugar | 0.24 | 99.73 | 0.04 | 0.19 | 99.79 | 0.03 | 0.53 | 99.02 | 0.46 | 1.11 | 98.29 | 0.61 |
| 5 amino acids w/o sugar | 0.19 | 99.79 | 0.03 | 0.18 | 99.80 | 0.03 | 0.40 | 99.09 | 0.52 | 0.88 | 98.44 | 0.68 |
| 2 amino acids with trehalose (original formulation) | 0.19 | 99.78 | 0.04 | 0.20 | 99.77 | 0.03 | 0.57 | 99.00 | 0.44 | 1.07 | 98.37 | 0.55 |
| 3 amino acids with trehalose | 0.19 | 99.78 | 0.03 | 0.18 | 99.80 | 0.03 | 0.43 | 99.06 | 0.52 | 0.93 | 98.44 | 0.63 |
| 5 amino acids with trehalose | 0.18 | 99.79 | 0.03 | 0.18 | 99.80 | 0.03 | 0.34 | 99.17 | 0.49 | 0.80 | 98.60 | 0.60 |

The invention claimed is:

1. A method of producing low viscous and highly concentrated biopharmaceutical drug products comprising an antibody, the method comprising:

(a) a first phase of preparing a drug substance comprising an antibody, said first phase comprising at least one processing step of concentration,
wherein said at least one processing step in this first phase is carried out in the presence of a composition comprising at least three amino acids, wherein the combination of said at least three amino acids provides at least one positively charged functional group, at least one anti-oxidative functional group, at least one osmolytic function, and at least one buffering function; and (b) a second phase of further processing the drug substance prepared in (a) to obtain a low viscous and highly concentrated biopharmaceutical drug product, said second phase comprising at least one processing step selected from (b1) re-buffering, and (b2) filling, wherein said at least one processing step in this second phase is carried out in the presence of a composition comprising (i) at least three amino acids, wherein the combination of said at least three amino acids provides at least one positively charged functional group, at least one anti-oxidative functional group, at least one osmolytic function, and at least one buffering function, and (ii) one or more sugar(s);

in an amino acid:sugar ratio between 10:1 to 1:100 (w/w);

and further comprising a step of storing the biopharmaceutical drug product at a concentration ranging from 100 to 500 mg/ml obtained in (b) in liquid formulation for at least 1.5 days.

2. The method of claim 1, wherein the low viscous and highly concentrated biopharmaceutical drug product obtained in (b) is further processed for administration as a liquid formulation.

3. The method of claim 2, wherein the liquid formulation comprises
   (i) at least three amino acids, wherein the combination of said at least three amino acids provides at least one positively charged functional group, at least one anti-oxidative functional group, at least one osmolytic function, and at least one buffering function, and
   (ii) one or more sugar(s);
   and wherein the ratio between the amino acids and the sugar is adjusted to be between 4:1 to 1:1 (w/w).

4. The method of claim 3, wherein the liquid formulation is further adjusted such that the ratio between the antibody and the at least three amino acids of (i) is between 3.5:1 to 1:2 (w/w).

5. The method of claim 1 wherein the composition in step (a) contains between 0.5 mg/ml and 10 mg/ml tryptophan and between 0.5 mg/ml and 30 mg/ml histidine.

6. The method of claim 1, wherein the antibody is a therapeutic antibody.

7. The method of claim 1, wherein the antibody is a diagnostic antibody.

8. The method of claim 1, wherein the antibody is an antibody for experimental purposes.

9. The method of claim 3, wherein the ratio between the amino acids and the sugar is adjusted to between 2.5:1 and 1:1.

10. The method of claim 5, wherein the ratio between the antibody and sum of excipients is adjusted to be between 1:1 and 1:500.

11. The method of claim 4, wherein the ratio between the amino acids and the sugar is adjusted to between 2.5:1 and 1:1.

12. The method of claim 5, wherein the ratio between the amino acids and the sugar is adjusted to between 4:1 and 1:1.

* * * * *